(12) United States Patent
Grasso et al.

(10) Patent No.: US 7,604,994 B2
(45) Date of Patent: *Oct. 20, 2009

(54) GENETICALLY ALTERED ANTIBODY-PRODUCING CELL LINES WITH IMPROVED ANTIBODY CHARACTERISTICS

(75) Inventors: Luigi Grasso, Bala Cynwyd, PA (US); Nicholas C. Nicolaides, Boothwyn, PA (US); Philip M. Sass, Audubon, PA (US)

(73) Assignee: Morphotek, Inc., Exton, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/933,034

(22) Filed: Sep. 2, 2004

(65) Prior Publication Data

US 2005/0048621 A1 Mar. 3, 2005

Related U.S. Application Data

(60) Provisional application No. 60/500,071, filed on Sep. 3, 2003.

(51) Int. Cl.
*C12N 15/00* (2006.01)
(52) U.S. Cl. .................................................... 435/455
(58) Field of Classification Search .................. 435/455
See application file for complete search history.

(56) References Cited

U.S. PATENT DOCUMENTS

| 4,376,110 | A | | 3/1983 | David et al. ................. 436/513 |
| 4,720,459 | A | | 1/1988 | Winkelhake ............. 435/240.2 |
| 5,530,101 | A | | 6/1996 | Queen et al. ............. 530/387.3 |
| 6,808,894 | B1 | * | 10/2004 | Nicolaides et al. ......... 435/69.1 |
| 2003/0170895 | A1 | | 9/2003 | Grasso et al. ............... 435/455 |

FOREIGN PATENT DOCUMENTS

| WO | WO 02/37967 A1 | | 5/2002 |
| WO | WO 02/054856 | * | 7/2002 |
| WO | WO 02/054856 A1 | | 7/2002 |
| WO | WO 02/0524856 | * | 7/2002 |
| WO | WO 03/061363 | * | 7/2003 |
| WO | WO 03/061363 A2 | * | 7/2003 |

OTHER PUBLICATIONS

Martin et al (Nature, Feb. 14, 2002, 415:802-806).*
Teng et al (Biochem. J., 1982, 203:471-476).*
Muto et al (Genomics, Aug. 15, 2000, 68:85-88).*
Gao et al (J. Immunol., Aug. 15, 2001, 167(4) 2011-2018).*
Zhang et al (International Immunology, Sep. 13, 2001, 13(9): 1175-1184).*
Kirikae et al (Int. J. Immunopharmac. (19)5:255-262), (1997).*
Burgess et al. (J. Cell Biol. 111:2129-2138, 1990).*
Lazar et al. (Mol. Cell Biol. 8:1247-1252, 1998).*
Borrebaeck et al (PNAS, Mar. 1988, 85: 3995-3999).*
Borrebaeck et al (PNAS, Mar. 1988, 85: 3995-3999).*
Gao et al (J. Immunol. Aug. 15, 2001, 167(4): 2011-2018).*
Sequence comparison, (2007).*

Drummond, J.T., et al., "Isolation of an hMSH2-p160 heterodimer that restores DNA mismatch repair to tumor cells," *Science*, 1995, 268, 1909-1912.
Drummond, J.T., et al., "Cisplatin and adriamycin resistance are associated with MutLα and mismatch repair deficiency in an ovarian tumor cell line," *J. Biol. Chem.*, 1996, 271, 19645-19648.
Emery, S.C., et al., "Strategies for humanizing antibodies," in Antibody Engineering, Borrebaeck, C.A.K. (Ed.), Oxford University Press, NY, 1995, 159-183.
Eshleman, J.R., et al., "Mismatch repair defects in human carcinogenesis," *Hum. Mol. Genet.*, 1996, 5, 1489-1494.
Fiedler, U., et al., "High-level production and long-term storage of engineered antibodies in transgenic tobacco seeds," *Bio/Technology*, 1995, 13, 1090-1093.
Frigerio, L., et al., "Assembly, secretion, and vacuolar delivery of a hybrid immunoglobulin in plants," *Plant Physiol.*, 2000, 123, 1483-1494.
Galfre, G., et al., "Antibodies to major histocompatibility antigens produced by hybrid cell lines," *Nature*, 1977, 266, 55052.
Gefter, M.L., et al., "A simple method for polyethylene glycol-promoted hybridization of mouse myeloma cells," *Somatic Cell Genet.*, 1977, 3(2), 231-236.
Galio, L., et al., "ATP hydrolysis-dependent formation of a dynamic ternary nucleoprotein complex with MutS and MutL," *Nucl. Acids Res.*, 1999, 27(11), 2325- 2331.
Glaser, V., "Can ReoPro repolish tarnished monoclonal therapeutics?," *Nat. Biotechnol.*, 1996, 14, 1216-1217.
Khazaeli, M.B., et al., "Human immune response to monoclonal antibodies," *J. Immunother.*, 1994, 15, 42-52.
Kitagawa, T., et al., "Enzyme coupled immunoassay of insulin using a novel coupling reagent," *J. Biochem*, 1976, 79, 233-236.
Köhler, G., et al., "Continuous cultures of fused cells secreting antibody of predefined specificity," *Nature*, 1975, 256, 495-497.
Kozbor, D., et al., "The production of monoclonal antibodies from human lymphocytes," *Immunology Today*, 1983, 4(3), 72-79.
Lerner, E.A., "How to make a hybridoma," *Yale J. of Biol. Med.*, 1981, 54, 387-402.
Liu, T., et al., "Microsatellite instability as a predictor of a mutation in a DNA mismatch repair gene in familial colorectal cancer," *Genes Chromosomes Cancer*, 2000, 27, 17-25.
Modrich, P., "Mismatch repair, genetic stability, and cancer," *Science*, 1994, 266, 1959-1960.
Muramatsu, M., et al., "Class switch recombination and hypermutation require activation-induced cytidine deaminase (AID), a potential RNA editing enzyme," *Cell*, 2000, 102, 553-563.

(Continued)

*Primary Examiner*—Sean E Aeder
(74) *Attorney, Agent, or Firm*—Woodcock Washburn LLP

(57) ABSTRACT

Dominant negative alleles of human mismatch repair genes can be used to generate hypermutable cells and organisms. Cells may be selected for expression of activation-induced cytidine deaminase (AID), stimulated to produce AID, or manipulated to express AID for further enhancement of hypermutability. These methods are useful for generating genetic diversity within immunoglobulin genes directed against an antigen of interest to produce altered antibodies with enhanced biochemical activity. Moreover, these methods are useful for generating antibody-producing cells with increased level of antibody production.

29 Claims, 8 Drawing Sheets

OTHER PUBLICATIONS

Muramatsu, M., et al., "Specific expression of activation-induced cytidine deaminase (AID), a novel member of the RNA-editing deaminase family in germinal center B cells," *J. of Biol. Chem.*, 1999, 274(26), 18470-18476.

Muto, T., et al., "Isolation, tissue distribution, and chromosomal localization of the human activation-induced cytidine deaminase (*Aid*) gene," *Genomics*, 2000, 68, 85-88.

Neuberger, M., et al., "Monoclonal antibodies. Mice perform a human repertoire," *Nature*, 1997, 386, 25-26.

Nicolaides, N.C., et al., "A naturally occurring *hPMS2* mutation can confer a dominant negative mutator phenotype," *Mol. Cell. Biol.*, 1998, 18(3), 1635-1641.

Nicolaides, N.C., et al., "Analysis of the 5' region of PMS2 reveals heterogeneous transcripts and a novel overlapping gene," *Genomics*, 1995, 29, 329-334.

Nicolaides, N.C., et al., "Genomic organization of the human PMS2 gene family," *Genomics*, 1995, 30, 195-206.

Nicolaides, N.C., et al., "The Jun family members, c-Jun and JunD, transactivate the human c-*myb* promoter via an Ap-1 like element," *J. Biol. Chem.*, 1992, 267, 19665-19672.

Okazaki, I.-M., et al., "The AID enzyme induces class switch recombination in fibroblasts," *Nature*, 2002, 416, 340-345.

Palombo, F., et al., "Mismatch repair and cancer," *Nature*, 1994, 36, p. 417.

Papadopoulos, N., et al., Mutation of a mutL homolog in hereditary colon cancer, *Science*, 1993, 1625-1629.

Parsons, R., et al., "Hypermutability and mismatch repair deficiency in RER+ tumor cells," 1993, 75, 1227-1236.

Perucho, M., "Cancer of the microsatellite mutator phenotype," *Biol. Chem.*, 1996, 377, 675-684.

Petersen, S., et al., "AID is required to initiate Nbs1/γ-H2AX focus formation and mutations at sites of class switching," *Nature*, 2001, 414, 660-665.

Petersen-Mahrt, S.K., et al., "AID mutates *E. coli* suggesting a DNA deamination mechanism for antibody diversification," *Nature*, 2002, 418, 99-103.

Prolla, T.A., et al., "MLH1, PMS1, and MSH2 interaction during the initiation of DNA mismatch repair in yeast," *Science*, 1994, 264, 1091-1093.

Reff, M.E., "High-level production of recombinant immunoglobulins in mammalian cells," *Curr. Opin. Biotechnol.*, 1993, 4, 573-576.

Revy, P., et al., "Activation-induced cytidine deaminase (AID) deficiency causes the autosomal recessive form of the hyper-IgM syndrome (HIGM2)," *Cell*, 2000, 102, 565-575.

Saez-Ilorens, X.E., et al., "Safety and pharmacokinetics of an intramuscular humanized monoclonal antibody to respiratory syncytial virus in premature infants and infants with bronchopulmonary dysplasia," *Pediat. Infect. Dis. J*, 1998, 17(9), 787-791.

Shield, C.F., et al., "A cost-effectiveness analysis of OKT3 induction therapy in cadaveric kidney transplantation," *Am. J. Kidney Dis.*, 1996, 27, 855-864.

Shields, R.L., et al., "Anti-IgE monoclonal antibodies that inhibit allergen-specific histamine release," *Int. Arch. Allergy Immunol.*, 1995, 107, 412-413.

Strand, M., et al., "Destabilization of tracts of simple repetitive DNA in yeast by mutations affecting DNA mismatch repair," *Nature*, 1993, 365, 274-276.

Su, S.S., et al., "Mispair specificity of methyl directed DNA mismatch corrections in vitro," *J. Biol. Chem.*, 1988, 263(14), 6829-6835.

Thorell, et al., Radioimmunoassay and Related Techniques: Methodology and Clinical Applications, *The C.V. Mosby Co.*, 1978, p. 288.

Weiner, L.M., "Monoclonal antibody therapy of cancer," *Semin. In Oncol.*, 1999, 26(5), 43-51.

Yeh, M.-Y., et al., "A cell-surface antigen which is present in the ganglioside fraction and shared by human melanomas," *Int. J. Cancer*, 1982, 29, 269-275.

Yeh, M.-Y., et al., "Cell surface antigens of human melanoma identified by monoclonal antibody," *Proc. Natl. Acad. Sci. USA*, 1979, 76(6), 2927-2931.

Yoshikawa, K., et al., "AID enzyme-induced hypermutation in an actively transcribed gene in fibroblasts," *Science*, 2002, 296, 2033-2036.

Martin, A. et al., "AID and mismatch repair in antibody diversification," *Nat. Rev. Immunology*, Aug. 2002, 2(8):605-614.

Nagumo, H. et al., "The different process of class switching and somatic hypermutation; a novel analysis by CD27 naïve cells," *Blood*, Jan. 2002, 99(2):567-575.

Martin, A. et al., "Activation-induced cytidine deaminase turns on somatic hypermutation in hybridomas," *Nature*, Feb. 14, 2002, 415(6873):802-806.

Risinger J. I. et al., "A hPMS2 mutant cell line is defective in strand-specific mismatch repair," *J Biol Chem*, Aug. 4, 1995, 270(31):18183-18186.

Winter, D. B. et al. "Altered spectra of hypermutation in antibodies from mice deficient for the DNA mismatch repair protein PMS2," *Proc Natl Acad Sci USA*, Jun. 1998, 95(12):6953-6958.

Neuberger, M. S. et al., "Immunity through DNA deamination," *Trends in Biochemical Sciences*, Jun. 2003, 28(6):305-312.

Diaz, M. et al., "A novel cytidine deaminase AIDs in the delivery of error-prone polymerases to immunoglobulin genes," *DNA Repair*, May 13, 2003, 2(5):623-627.

Zafiropoulos, A. et al., "In vitro induction of somatic mutations in human peripheral B lymphocytes," *International Journal of Molecular Medicine*, Oct. 2000, 6(4):1107-3756.

Razanajaona, D. et al., "In vitro triggering of somatic mutation in human naïve B cells," *Journal of Immunology*, Oct. 1, 1997, 159(7):3347-3353.

Irving, R.A. et al, "Affinity maturation of recombinant antibodies using *E. coli* mutator cells," Immunotechnology, 1996, 2, 127-143.

Accession No. NM_020661, 6 pages, (2004).

Baker, S.M., et al., "Male defective in the DNA mismatch repair gene PMS2 exhibit abnormal chromosome synapsis in meiosis," *Cell*, 1995, 82, 309-319.

Bignami, M., "Unmasking a killer: DNA O(6)-methylguanine and the cytotoxicity of methylating agents," *Mutat. Res.*, 2000, 462, 71-82.

Borrebaeck, C.A.K., "Human mAbs produced by primary in-vitro immunization," *Immunol. Today*, 1988, 9(11), 355-359.

Bronner, C.E., et al., "Mutation in the DNA mismatch repair gene homologue h*MLH1* associated with hereditary non-polyposis colon cancer," *Nature*, 1994, 368, 258-261.

Brown, J.P., et al., "Structural characterization of human melanoma-associated antigen p97 with monoclonal antibodies," *J. of Immunol.*, 1981, 127(2), 539-546.

Brown, J.P., et al., "Protein antigens of normal and malignant human cells identified by immunoprecipitation with monoclonal antibodies," *J. of Biol. Chem.*, 1980, 255(11), 4980-4983.

Cole, et al., Monoclonal Antibodies and Cancer Therapy, Alan R. Liss, Inc., 1985, 77-96.

Cote, R.J., et al., "Generation of human monoclonal antibodies reactive with cellular antigens," *Proc. Natl. Acad. Sci. USA*, 1983, 80, 2026-2030.

de Wind, N., et al., "Inactivation of the mouse Msh2 gene results in mismatch repair deficiency, methylation tolerance, hyperrecombination, and predisposition to cancer," *Cell*, 1995, 82, 321-330.

* cited by examiner

SEQUENCE LISTING

<160> NUMBER OF SEQ ID NOS: 55

<210> SEQ ID NO 1
<211> LENGTH: 3063
<212> TYPE: DNA
<213> ORGANISM: Homo sapiens

<400> SEQUENCE: 1

```
ggcacgagtg gctgcttgcg gctagtggat ggtaattgcc tgcctcgcgc tagcagcaag      60
ctgctctgtt aaaagcgaaa atgaaacaat tgcctgcggc aacagttcga ctcctttcaa     120
gttctcagat catcacttcg gtggtcagtg ttgtaaaaga gcttattgaa aactccttgg     180
atgctggtgc cacaagcgta gatgttaaac tggagaacta tggatttgat aaaattgagg     240
tgcgagataa cggggagggt atcaaggctg ttgatgcacc tgtaatggca atgaagtact     300
acacctcaaa aataaatagt catgaagatc ttgaaaattt gacaacttac ggttttcgtg     360
gagaagcctt ggggtcaatt tgttgtatag ctgaggtttt aattacaaca agaacggctg     420
ctgataattt tagcacccag tatgttttag atggcagtgg ccacatactt tctcagaaac     480
cttcacatct tggtcaaggt acaactgtaa ctgctttaag attatttaag aatctacctg     540
taagaaagca gttttactca actgcaaaaa aatgtaaaga tgaaataaaa aagatccaag     600
atctcctcat gagctttggt atccttaaac ctgacttaag gattgtcttt gtacataaca     660
aggcagttat ttggcagaaa agcagagtat cagatcacaa gatggctctc atgtcagttc     720
tggggactgc tgttatgaac aatatggaat cctttcagta ccactctgaa gaatctcaga     780
tttatctcag tggatttctt ccaaagtgtg atgcagacca ctctttcact agtctttcaa     840
caccagaaag aagtttcatc ttcataaaca gtcgaccagt acatcaaaaa gatatcttaa     900
agttaatccg acatcattac aatctgaaat gcctaaagga atctactcgt ttgtatcctg     960 ttttcttttct gaaaatcgat gttcctacag ctgatgttga tgtaaattta acaccagata    1020
aaagccaagt attattacaa aataaggaat ctgttttaat tgctcttgaa aatctgatga    1080
cgacttgtta tggaccatta cctagtacaa attcttatga aaataataaa acagatgttt    1140
ccgcagctga catcgttctt agtaaaacag cagaaacaga tgtgcttttt aataaagtgg    1200
aatcatctga aagaattat tcaaatgttg atacttcagt cattccattc caaaatgata    1260
tgcataatga tgaatctgga aaaaacactg atgattgttt aaatcaccag ataagtattg    1320
```

```
gtgactttgg ttatggtcat tgtagtagtg aaatttctaa cattgataaa aacactaaga    1380
atgcatttca ggacatttca atgagtaatg tatcatggga gaactctcag acggaatata    1440
gtaaaacttg ttttataagt tccgttaagc acacccagtc agaaaatggc aataaagacc    1500
atatagatga gagtggggaa aatgaggaag aagcaggtct tgaaaactct tcggaaattt    1560
ctgcagatga gtggagcagg ggaaatatac ttaaaaattc agtgggagag aatattgaac    1620
ctgtgaaaat tttagtgcct gaaaaagtt taccatgtaa agtaagtaat aataattatc    1680
caatccctga acaaatgaat cttaatgaag attcatgtaa caaaaaatca aatgtaatag    1740
ataataaatc tggaaaagtt acagcttatg atttacttag caatcgagta atcaagaaac    1800
ccatgtcagc aagtgctctt tttgttcaag atcatcgtcc tcagtttctc atagaaaatc    1860
ctaagactag tttagaggat gcaacactac aaattgaaga actgtggaag acattgagtg    1920
aagaggaaaa actgaaatat gaagagaagg ctactaaaga cttggaacga tacaatagtc    1980
aaatgaagag agccattgaa caggagtcac aaatgtcact aaaagatggc agaaaaaaga    2040
taaaacccac cagcgcatgg aatttggccc agaagcacaa gttaaaaacc tcattatcta    2100
atcaaccaaa acttgatgaa ctccttcagt cccaaattga aaaagaagg agtcaaaata    2160 ttaaaatggt acagatcccc ttttctatga aaaacttaaa aataaatttt aagaaacaaa    2220
acaaagttga cttagaagag aaggatgaac cttgcttgat ccacaatctc aggtttcctg    2280
atgcatggct aatgacatcc aaaacagagg taatgttatt aaatccatat agagtagaag    2340
aagccctgct atttaaaaga cttcttgaga atcataaact tcctgcagag ccactggaaa    2400
agccaattat gttaacagag agtctttta atggatctca ttatttagac gttttatata    2460
aaatgacagc agatgaccaa agatacagtg gatcaactta cctgtctgat cctcgtctta    2520
cagcgaatgg tttcaagata aaattgatac caggagtttc aattactgaa aattacttgg    2580
aaatagaagg aatggctaat tgtctcccat tctatggagt agcagattta aaagaaattc    2640
ttaatgctat attaaacaga aatgcaaagg aagtttatga atgtagacct cgcaaagtga    2700
taagttattt agagggagaa gcagtgcgtc tatccagaca attacccatg tacttatcaa    2760
aagaggacat ccaagacatt atctacagaa tgaagcacca gtttggaaat gaaattaaag    2820
agtgtgttca tggtcgccca tttttttcatc atttaaccta tcttccagaa actacatgat    2880
taaatatgtt taagaagatt agttaccatt gaaattggtt ctgtcataaa acagcatgag    2940
tctggtttta aattatcttt gtattatgtg tcacatggtt attttttaaa tgaggattca    3000
ctgacttgtt tttatattga aaaagttcc acgtattgta gaaaacgtaa ataaactaat    3060
aac                                                                  3063
```

<210> SEQ ID NO 2
<211> LENGTH: 932
<212> TYPE: PRT
<213> ORGANISM: Homo sapiens

<400> SEQUENCE: 2

```
Met Lys Gln Leu Pro Ala Ala Thr Val Arg Leu Leu Ser Ser Ser Gln
1               5                   10                  15

Ile Ile Thr Ser Val Val Ser Val Val Lys Glu Leu Ile Glu Asn Ser
            20                  25                  30

Leu Asp Ala Gly Ala Thr Ser Val Asp Val Lys Leu Glu Asn Tyr Gly
        35                  40                  45

Phe Asp Lys Ile Glu Val Arg Asp Asn Gly Glu Gly Ile Lys Ala Val
    50                  55                  60
```

-continued

```
Asp Ala Pro Val Met Ala Met Lys Tyr Tyr Thr Ser Lys Ile Asn Ser
 65                  70                  75                  80

His Glu Asp Leu Glu Asn Leu Thr Thr Tyr Gly Phe Arg Gly Glu Ala
             85                  90                  95

Leu Gly Ser Ile Cys Cys Ile Ala Glu Val Leu Ile Thr Thr Arg Thr
            100                 105                 110

Ala Ala Asp Asn Phe Ser Thr Gln Tyr Val Leu Asp Gly Ser Gly His
        115                 120                 125

Ile Leu Ser Gln Lys Pro Ser His Leu Gly Gln Gly Thr Thr Val Thr
130                 135                 140

Ala Leu Arg Leu Phe Lys Asn Leu Pro Val Arg Lys Gln Phe Tyr Ser
145                 150                 155                 160

Thr Ala Lys Lys Cys Lys Asp Glu Ile Lys Ile Gln Asp Leu Leu
                165                 170                 175

Met Ser Phe Gly Ile Leu Lys Pro Asp Leu Arg Ile Val Phe Val His
            180                 185                 190

Asn Lys Ala Val Ile Trp Gln Lys Ser Arg Val Ser Asp His Lys Met
        195                 200                 205

Ala Leu Met Ser Val Leu Gly Thr Ala Val Met Asn Asn Met Glu Ser
210                 215                 220

Phe Gln Tyr His Ser Glu Glu Ser Gln Ile Tyr Leu Ser Gly Phe Leu
225                 230                 235                 240

Pro Lys Cys Asp Ala Asp His Ser Phe Thr Ser Leu Ser Thr Pro Glu
                245                 250                 255

Arg Ser Phe Ile Phe Ile Asn Ser Arg Pro Val His Gln Lys Asp Ile
            260                 265                 270

Leu Lys Leu Ile Arg His His Tyr Asn Leu Lys Cys Leu Lys Glu Ser
        275                 280                 285

Thr Arg Leu Tyr Pro Val Phe Phe Leu Lys Ile Asp Val Pro Thr Ala
290                 295                 300

Asp Val Asp Val Asn Leu Thr Pro Asp Lys Ser Gln Val Leu Leu Gln
305                 310                 315                 320

Asn Lys Glu Ser Val Leu Ile Ala Leu Glu Asn Leu Met Thr Thr Cys
                325                 330                 335

Tyr Gly Pro Leu Pro Ser Thr Asn Ser Tyr Glu Asn Asn Lys Thr Asp
            340                 345                 350

Val Ser Ala Ala Asp Ile Val Leu Ser Lys Thr Ala Glu Thr Asp Val
        355                 360                 365

Leu Phe Asn Lys Val Glu Ser Ser Gly Lys Asn Tyr Ser Asn Val Asp
370                 375                 380

Thr Ser Val Ile Pro Phe Gln Asn Asp Met His Asn Asp Glu Ser Gly
385                 390                 395                 400

Lys Asn Thr Asp Asp Cys Leu Asn His Gln Ile Ser Ile Gly Asp Phe
                405                 410                 415

Gly Tyr Gly His Cys Ser Ser Glu Ile Ser Asn Ile Asp Lys Asn Thr
            420                 425                 430

Lys Asn Ala Phe Gln Asp Ile Ser Met Ser Asn Val Ser Trp Glu Asn
        435                 440                 445

Ser Gln Thr Glu Tyr Ser Lys Thr Cys Phe Ile Ser Ser Val Lys His
450                 455                 460

Thr Gln Ser Glu Asn Gly Asn Lys Asp His Ile Asp Glu Ser Gly Glu
465                 470                 475                 480
```

-continued

```
Asn Glu Glu Glu Ala Gly Leu Glu Asn Ser Ser Ile Ser Ala Asp
                485                 490                 495

Glu Trp Ser Arg Gly Asn Ile Leu Lys Asn Ser Val Gly Glu Asn Ile
            500                 505                 510

Glu Pro Val Lys Ile Leu Val Pro Glu Lys Ser Leu Pro Cys Lys Val
            515                 520                 525

Ser Asn Asn Asn Tyr Pro Ile Pro Glu Gln Met Asn Leu Asn Glu Asp
    530                 535                 540

Ser Cys Asn Lys Lys Ser Asn Val Ile Asp Asn Lys Ser Gly Lys Val
545                 550                 555                 560

Thr Ala Tyr Asp Leu Leu Ser Asn Arg Val Ile Lys Lys Pro Met Ser
                565                 570                 575

Ala Ser Ala Leu Phe Val Gln Asp His Arg Pro Gln Phe Leu Ile Glu
            580                 585                 590

Asn Pro Lys Thr Ser Leu Glu Asp Ala Thr Leu Gln Ile Glu Glu Leu
            595                 600                 605

Trp Lys Thr Leu Ser Glu Glu Lys Leu Lys Tyr Glu Glu Lys Ala
    610                 615                 620

Thr Lys Asp Leu Glu Arg Tyr Asn Ser Gln Met Lys Arg Ala Ile Glu
625                 630                 635                 640

Gln Glu Ser Gln Met Ser Leu Lys Asp Gly Arg Lys Ile Lys Pro
                645                 650                 655

Thr Ser Ala Trp Asn Leu Ala Gln Lys His Lys Leu Lys Thr Ser Leu
            660                 665                 670

Ser Asn Gln Pro Lys Leu Asp Glu Leu Leu Gln Ser Gln Ile Glu Lys
        675                 680                 685

Arg Arg Ser Gln Asn Ile Lys Met Val Gln Ile Pro Phe Ser Met Lys
    690                 695                 700

Asn Leu Lys Ile Asn Phe Lys Lys Gln Asn Lys Val Asp Leu Glu Glu
705                 710                 715                 720

Lys Asp Glu Pro Cys Leu Ile His Asn Leu Arg Phe Pro Asp Ala Trp
                725                 730                 735

Leu Met Thr Ser Lys Thr Glu Val Met Leu Leu Asn Pro Tyr Arg Val
            740                 745                 750

Glu Glu Ala Leu Leu Phe Lys Arg Leu Leu Glu Asn His Lys Leu Pro
            755                 760                 765

Ala Glu Pro Leu Glu Lys Pro Ile Met Leu Thr Glu Ser Leu Phe Asn
    770                 775                 780

Gly Ser His Tyr Leu Asp Val Leu Tyr Lys Met Thr Ala Asp Asp Gln
785                 790                 795                 800

Arg Tyr Ser Gly Ser Thr Tyr Leu Ser Asp Pro Arg Leu Thr Ala Asn
                805                 810                 815

Gly Phe Lys Ile Lys Leu Ile Pro Gly Val Ser Ile Thr Glu Asn Tyr
            820                 825                 830

Leu Glu Ile Glu Gly Met Ala Asn Cys Leu Pro Phe Tyr Gly Val Ala
        835                 840                 845

Asp Leu Lys Glu Ile Leu Asn Ala Ile Leu Asn Arg Asn Ala Lys Glu
    850                 855                 860

Val Tyr Glu Cys Arg Pro Arg Lys Val Ile Ser Tyr Leu Glu Gly Glu
865                 870                 875                 880

Ala Val Arg Leu Ser Arg Gln Leu Pro Met Tyr Leu Ser Lys Glu Asp
                885                 890                 895

Ile Gln Asp Ile Ile Tyr Arg Met Lys His Gln Phe Gly Asn Glu Ile
```

|  |  |  |  |  |  |  |  |  |  |
|---|---|---|---|---|---|---|---|---|---|
| Lys | Glu | Cys | Val | His | Gly | Arg | Pro | Phe | Phe | His | His | Leu | Thr | Tyr | Leu |
| 900 | | | | | 905 | | | | | 910 | | | | | |
| Lys Glu Cys Val His Gly Arg Pro Phe Phe His His Leu Thr Tyr Leu |
| 915 | 920 | 925 |

Pro Glu Thr Thr
930

<210> SEQ ID NO 3
<211> LENGTH: 2771
<212> TYPE: DNA
<213> ORGANISM: Homo sapiens

<400> SEQUENCE: 3

| cgaggcggat cgggtgttgc atccatggag cgagctgaga gctcgagtac agaacctgct | 60 |
| aaggccatca aacctattga tcggaagtca gtccatcaga tttgctctgg gcaggtggta | 120 |
| ctgagtctaa gcactgcggt aaaggagtta gtagaaaaca gtctggatgc tggtgccact | 180 |
| aatattgatc taaagcttaa ggactatgga gtggatctta ttgaagtttc agacaatgga | 240 |
| tgtggggtag aagaagaaaa cttcgaaggc ttaactctga acatcacac atctaagatt | 300 |
| caagagtttg ccgacctaac tcaggttgaa acttttggct tcggggggga agctctgagc | 360 |
| tcactttgtg cactgagcga tgtcaccatt tctacctgcc acgcatcggc gaaggttgga | 420 |
| actcgactga tgtttgatca caatgggaaa attatccaga aaaccccta cccccgcccc | 480 |
| agagggacca cagtcagcgt gcagcagtta ttttccacac tacctgtgcg ccataaggaa | 540 |
| tttcaaagga atattaagaa ggagtatgcc aaaatggtcc aggtcttaca tgcatactgt | 600 |
| atcatttcag caggcatccg tgtaagttgc accaatcagc ttggacaagg aaaacgacag | 660 |
| cctgtggtat gcacaggtgg aagccccagc ataaaggaaa atatcggctc tgtgtttggg | 720 |
| cagaagcagt tgcaaagcct cattcctttt gttcagctgc cccctagtga ctccgtgtgt | 780 |
| gaagagtacg gtttgagctg ttcggatgct ctgcataatc ttttttacat ctcaggtttc | 840 |
| atttcacaat gcacgcatgg agttggaagg agttcaacag acagacagtt tttctttatc | 900 |
| aaccggcggc cttgtgaccc agcaaaggtc tgcagactcg tgaatgaggt ctaccacatg | 960 |
| tataatcgac accagtatcc atttgttgtt cttaacattt ctgttgattc agaatgcgtt | 1020 |
| gatatcaatg ttactccaga taaaaggcaa attttgctac aagaggaaaa gcttttgttg | 1080 |
| gcagttttaa agacctcttt gataggaatg tttgatagtg atgtcaacaa gctaaatgtc | 1140 |
| agtcagcagc cactgctgga tgttgaaggt aacttaataa aaatgcatgc agcggatttg | 1200 |
| gaaaagccca tggtagaaaa gcaggatcaa tccccttcat taaggactgg agaagaaaaa | 1260 |
| aaagacgtgt ccattttccag actgcgagag gccttttctc ttcgtcacac aacagagaac | 1320 |
| aagcctcaca gcccaaagac tccagaacca agaaggagcc ctctaggaca gaaaggggt | 1380 |
| atgctgtctt ctagcacttc aggtgccatc tctgacaaag gcgtcctgag acctcagaaa | 1440 |
| gaggcagtga gttccagtca cggacccagt gaccctacgg acagagcgga ggtggagaag | 1500 |
| gactcggggc acggcagcac ttccgtggat tctgaggggt tcagcatccc agacacgggc | 1560 |
| agtcactgca gcagcgagta tgcggccagc tccccagggg acaggggctc gcaggaacat | 1620 |
| gtggactctc aggagaaagc gcctgaaact gacgactctt tttcagatgt ggactgccat | 1680 |
| tcaaaccagg aagataccgg atgtaaattt cgagttttgc ctcagccaac taatctcgca | 1740 |
| accccaaaca caaagcgttt taaaaagaa gaaattcttt ccagttctga catttgtcaa | 1800 |
| aagttagtaa atactcagga catgtcagcc tctcaggttg atgtagctgt gaaaattaat | 1860 |
| aagaaagttg tgcccctgga cttttctatg agttctttag ctaaacgaat aaagcagtta | 1920 |

-continued

```
catcatgaag cacagcaaag tgaaggggaa cagaattaca ggaagtttag ggcaaagatt    1980
tgtcctggag aaatcaagc agccgaagat gaactaagaa aagagataag taaaacgatg    2040
tttgcagaaa tggaaatcat tggtcagttt aacctgggat ttataataac caaactgaat    2100
gaggatatct tcatagtgga ccagcatgcc acggacgaga agtataactt cgagatgctg    2160
cagcagcaca ccgtgctcca ggggcagagg ctcatagcac ctcagactct caacttaact    2220
gctgttaatg aagctgttct gatagaaaat ctggaaatat ttagaaagaa tggctttgat    2280
tttgttatcg atgaaaatgc tccagtcact gaaagggcta aactgatttc cttgccaact    2340
agtaaaaact ggaccttcgg accccaggac gtcgatgaac tgatcttcat gctgagcgac    2400
agccctgggg tcatgtgccg gccttcccga gtcaagcaga tgtttgcctc cagagcctgc    2460
cggaagtcgg tgatgattgg gactgctctt aacacaagcg agatgaagaa actgatcacc    2520 cacatgggg agatggacca cccctggaac tgtccccatg gaaggccaac catgagacac    2580
atcgccaacc tgggtgtcat ttctcagaac tgaccgtagt cactgtatgg aataattggt    2640
tttatcgcag atttttatgt tttgaaagac agagtcttca ctaacctttt ttgttttaaa    2700
atgaaacctg ctactaaaaa aaaatacaca tcacacccat ttaaaagtga tcttgagaac    2760
cttttcaaac c                                                        2771
```

<210> SEQ ID NO 4
<211> LENGTH: 862
<212> TYPE: PRT
<213> ORGANISM: Homo sapiens

<400> SEQUENCE: 4

```
Met Glu Arg Ala Glu Ser Ser Ser Thr Glu Pro Ala Lys Ala Ile Lys
1               5                  10                  15

Pro Ile Asp Arg Lys Ser Val His Gln Ile Cys Ser Gly Gln Val Val
            20                  25                  30

Leu Ser Leu Ser Thr Ala Val Lys Glu Leu Val Glu Asn Ser Leu Asp
        35                  40                  45

Ala Gly Ala Thr Asn Ile Asp Leu Lys Leu Lys Asp Tyr Gly Val Asp
    50                  55                  60

Leu Ile Glu Val Ser Asp Asn Gly Cys Gly Val Glu Glu Glu Asn Phe
65                  70                  75                  80

Glu Gly Leu Thr Leu Lys His His Thr Ser Lys Ile Gln Glu Phe Ala
                85                  90                  95

Asp Leu Thr Gln Val Glu Thr Phe Gly Phe Arg Gly Glu Ala Leu Ser
            100                 105                 110

Ser Leu Cys Ala Leu Ser Asp Val Thr Ile Ser Thr Cys His Ala Ser
        115                 120                 125

Ala Lys Val Gly Thr Arg Leu Met Phe Asp His Asn Gly Lys Ile Ile
    130                 135                 140

Gln Lys Thr Pro Tyr Pro Arg Pro Arg Gly Thr Thr Val Ser Val Gln
145                 150                 155                 160

Gln Leu Phe Ser Thr Leu Pro Val Arg His Lys Glu Phe Gln Arg Asn
                165                 170                 175

Ile Lys Lys Glu Tyr Ala Lys Met Val Gln Val Leu His Ala Tyr Cys
            180                 185                 190

Ile Ile Ser Ala Gly Ile Arg Val Ser Cys Thr Asn Gln Leu Gly Gln
        195                 200                 205

Gly Lys Arg Gln Pro Val Val Cys Thr Gly Gly Ser Pro Ser Ile Lys
```

-continued

```
                210                 215                 220
Glu Asn Ile Gly Ser Val Phe Gly Gln Lys Gln Leu Gln Ser Leu Ile
225                 230                 235                 240

Pro Phe Val Gln Leu Pro Pro Ser Asp Ser Val Cys Glu Glu Tyr Gly
                245                 250                 255

Leu Ser Cys Ser Asp Ala Leu His Asn Leu Phe Tyr Ile Ser Gly Phe
                260                 265                 270

Ile Ser Gln Cys Thr His Gly Val Gly Arg Ser Ser Thr Asp Arg Gln
                275                 280                 285

Phe Phe Phe Ile Asn Arg Arg Pro Cys Asp Pro Ala Lys Val Cys Arg
290                 295                 300

Leu Val Asn Glu Val Tyr His Met Tyr Asn Arg His Gln Tyr Pro Phe
305                 310                 315                 320

Val Val Leu Asn Ile Ser Val Asp Ser Glu Cys Val Asp Ile Asn Val
                325                 330                 335

Thr Pro Asp Lys Arg Gln Ile Leu Leu Gln Glu Lys Leu Leu Leu
                340                 345                 350

Ala Val Leu Lys Thr Ser Leu Ile Gly Met Phe Asp Ser Asp Val Asn
                355                 360                 365

Lys Leu Asn Val Ser Gln Gln Pro Leu Leu Asp Val Glu Gly Asn Leu
                370                 375                 380

Ile Lys Met His Ala Ala Asp Leu Glu Lys Pro Met Val Glu Lys Gln
385                 390                 395                 400

Asp Gln Ser Pro Ser Leu Arg Thr Gly Glu Glu Lys Lys Asp Val Ser
                405                 410                 415

Ile Ser Arg Leu Arg Glu Ala Phe Ser Leu Arg His Thr Thr Glu Asn
                420                 425                 430

Lys Pro His Ser Pro Lys Thr Pro Glu Pro Arg Arg Ser Pro Leu Gly
                435                 440                 445

Gln Lys Arg Gly Met Leu Ser Ser Thr Ser Gly Ala Ile Ser Asp
                450                 455                 460

Lys Gly Val Leu Arg Pro Gln Lys Glu Ala Val Ser Ser Ser His Gly
465                 470                 475                 480

Pro Ser Asp Pro Thr Asp Arg Ala Glu Val Glu Lys Asp Ser Gly His
                485                 490                 495

Gly Ser Thr Ser Val Asp Ser Glu Gly Phe Ser Ile Pro Asp Thr Gly
                500                 505                 510

Ser His Cys Ser Ser Glu Tyr Ala Ala Ser Ser Pro Gly Asp Arg Gly
                515                 520                 525

Ser Gln Glu His Val Asp Ser Gln Glu Lys Ala Pro Glu Thr Asp Asp
530                 535                 540

Ser Phe Ser Asp Val Asp Cys His Ser Asn Gln Glu Asp Thr Gly Cys
545                 550                 555                 560

Lys Phe Arg Val Leu Pro Gln Pro Thr Asn Leu Ala Thr Pro Asn Thr
                565                 570                 575

Lys Arg Phe Lys Lys Glu Glu Ile Leu Ser Ser Ser Asp Ile Cys Gln
                580                 585                 590

Lys Leu Val Asn Thr Gln Asp Met Ser Ala Ser Gln Val Asp Val Ala
                595                 600                 605

Val Lys Ile Asn Lys Lys Val Val Pro Leu Asp Phe Ser Met Ser Ser
                610                 615                 620

Leu Ala Lys Arg Ile Lys Gln Leu His His Glu Ala Gln Gln Ser Glu
625                 630                 635                 640
```

Gly Glu Gln Asn Tyr Arg Lys Phe Arg Ala Lys Ile Cys Pro Gly Glu
            645                 650                 655

Asn Gln Ala Ala Glu Asp Glu Leu Arg Lys Glu Ile Ser Lys Thr Met
        660                 665                 670

Phe Ala Glu Met Glu Ile Ile Gly Gln Phe Asn Leu Gly Phe Ile Ile
    675                 680                 685

Thr Lys Leu Asn Glu Asp Ile Phe Ile Val Asp Gln His Ala Thr Asp
690                 695                 700

Glu Lys Tyr Asn Phe Glu Met Leu Gln Gln His Thr Val Leu Gln Gly
705                 710                 715                 720

Gln Arg Leu Ile Ala Pro Gln Thr Leu Asn Leu Thr Ala Val Asn Glu
            725                 730                 735

Ala Val Leu Ile Glu Asn Leu Glu Ile Phe Arg Lys Asn Gly Phe Asp
        740                 745                 750

Phe Val Ile Asp Glu Asn Ala Pro Val Thr Glu Arg Ala Lys Leu Ile
    755                 760                 765

Ser Leu Pro Thr Ser Lys Asn Trp Thr Phe Gly Pro Gln Asp Val Asp
770                 775                 780

Glu Leu Ile Phe Met Leu Ser Asp Ser Pro Gly Val Met Cys Arg Pro
785                 790                 795                 800

Ser Arg Val Lys Gln Met Phe Ala Ser Arg Ala Cys Arg Lys Ser Val
            805                 810                 815

Met Ile Gly Thr Ala Leu Asn Thr Ser Glu Met Lys Lys Leu Ile Thr
        820                 825                 830

His Met Gly Glu Met Asp His Pro Trp Asn Cys Pro His Gly Arg Pro
    835                 840                 845

Thr Met Arg His Ile Ala Asn Leu Gly Val Ile Ser Gln Asn
    850                 855                 860

<210> SEQ ID NO 5
<211> LENGTH: 426
<212> TYPE: DNA
<213> ORGANISM: Homo sapiens

<400> SEQUENCE: 5
cgaggcggat cgggtgttgc atccatggag cgagctgaga gctcgagtac agaacctgct      60
aaggccatca aacctattga tcggaagtca gtccatcaga tttgctctgg caggtggta     120 ctgagtctaa gcactgcggt aaaggagtta gtagaaaaca gtctggatgc tggtgccact     180
aatattgatc taaagcttaa ggactatgga gtggatctta ttgaagtttc agacaatgga     240
tgtggggtag aagaagaaaa cttcgaaggc ttaactctga acatcacac atctaagatt     300 caagagtttg ccgacctaac tcaggttgaa acttttggct ttcgggggga agctctgagc     360
tcactttgtg cactgagcga tgtcaccatt tctacctgcc acgcatcggc gaaggttgga     420
acttga                                                                426

<210> SEQ ID NO 6
<211> LENGTH: 133
<212> TYPE: PRT
<213> ORGANISM: Homo sapiens

<400> SEQUENCE: 6

Met Glu Arg Ala Glu Ser Ser Ser Thr Glu Pro Ala Lys Ala Ile Lys
1               5                   10                  15

Pro Ile Asp Arg Lys Ser Val His Gln Ile Cys Ser Gly Gln Val Val

```
                 20                  25                  30
Leu Ser Leu Ser Thr Ala Val Lys Glu Leu Val Glu Asn Ser Leu Asp
         35                  40                  45

Ala Gly Ala Thr Asn Ile Asp Leu Lys Leu Lys Asp Tyr Gly Val Asp
 50                  55                  60

Leu Ile Glu Val Ser Asp Asn Gly Cys Gly Val Glu Glu Asn Phe
65                  70                  75                  80

Glu Gly Leu Thr Leu Lys His His Thr Ser Lys Ile Gln Glu Phe Ala
                 85                  90                  95

Asp Leu Thr Gln Val Glu Thr Phe Gly Phe Arg Gly Glu Ala Leu Ser
            100                 105                 110

Ser Leu Cys Ala Leu Ser Asp Val Thr Ile Ser Thr Cys His Ala Ser
            115                 120                 125

Ala Lys Val Gly Thr
            130

<210> SEQ ID NO 7
<211> LENGTH: 1408
<212> TYPE: DNA
<213> ORGANISM: Homo sapiens

<400> SEQUENCE: 7
ggcgctccta cctgcaagtg gctagtgcca agtgctgggc cgccgctcct gccgtgcatg      60
ttggggagcc agtacatgca ggtgggctcc acacggagag gggcgcagac ccggtgacag     120
ggctttacct ggtacatcgg catggcgcaa ccaaagcaag agagggtggc gcgtgccaga     180
caccaacggt cggaaaccgc cagacaccaa cggtcggaaa ccgccaagac accaacgctc     240
ggaaaccgcc agacaccaac gctcggaaac cgccagacac caaggctcgg aatccacgcc     300
aggccacgac ggagggcgac tacctcccct ctgaccctgc tgctggcgtt cggaaaaaac     360
gcagtccggt gtgctctgat tggtccaggc tctttgacgt cacggactcg acctttgaca     420
gagccactag gcgaaaagga gagacgggaa gtatttttc cgccccgccc ggaaagggtg     480
gagcacaacg tcgaaagcag ccgttgggag cccaggaggc ggggcgcctg tgggagccgt     540
ggagggaact tcccagtcc ccgaggcgga tccggtgttg catccttgga gcgagctgag      600
aactcgagta cagaacctgc taaggccatc aaacctattg atcggaagtc agtccatcag     660
atttgctctg ggccggtggt accgagtcta aggccgaatg cggtgaagga gttagtagaa     720
aacagtctgg atgctggtgc cactaatgtt gatctaaagc ttaaggacta tggagtggat     780
ctcattgaag tttcaggcaa tggatgtggg gtagaagaag aaaacttcga aggctttact     840
ctgaaacatc acacatgtaa gattcaagag tttgccgacc taactcaggt ggaaactttt     900
ggctttcggg gggaagctct gagctcactt tgtgcactga gtgatgtcac catttctacc     960
tgccgtgtat cagcgaaggt tgggactcga ctggtgtttg atcactatgg gaaaatcatc    1020
cagaaaaccc cctaccccg cccagagggg atgacagtca gcgtgaagca gttatttct    1080 acgctacctg tgcaccataa gaatttcaa aggaatatta agaagaacg tgcctgcttc    1140 cccttcgcct tctgccgtga ttgtcagttt cctgaggcct cccagccat gcttcctgta    1200 cagcctgtag aactgactcc tagaagtacc cacccccacc cctgctcctt ggaggacaac    1260
gtgatcactg tattcagctc tgtcaagaat ggtccaggtt cttctagatg atctgcacaa    1320
atggttcctc tcctccttcc tgatgtctgc cattagcatt ggaataaagt tcctgctgaa    1380
aatccaaaaa aaaaaaaaaa aaaaaaaa                                      1408
```

<210> SEQ ID NO 8
<211> LENGTH: 389
<212> TYPE: PRT
<213> ORGANISM: Homo sapiens

<400> SEQUENCE: 8

Met Ala Gln Pro Lys Gln Glu Arg Val Ala Arg Ala Arg His Gln Arg
1               5                   10                  15

Ser Glu Thr Ala Arg His Gln Arg Ser Glu Thr Ala Lys Thr Pro Thr
            20                  25                  30

Leu Gly Asn Arg Gln Thr Pro Thr Leu Gly Asn Arg Gln Thr Pro Arg
        35                  40                  45

Leu Gly Ile His Ala Arg Pro Arg Arg Arg Ala Thr Thr Ser Leu Leu
    50                  55                  60

Thr Leu Leu Leu Ala Phe Gly Lys Asn Ala Val Arg Cys Ala Leu Ile
65                  70                  75                  80

Gly Pro Gly Ser Leu Thr Ser Arg Thr Arg Pro Leu Thr Glu Pro Leu
                85                  90                  95

Gly Glu Lys Glu Arg Arg Glu Val Phe Phe Pro Pro Arg Pro Glu Arg
            100                 105                 110

Val Glu His Asn Val Glu Ser Arg Trp Glu Pro Arg Arg Gly
        115                 120                 125

Ala Cys Gly Ser Arg Gly Gly Asn Phe Pro Ser Pro Arg Gly Gly Ser
    130                 135                 140

Gly Val Ala Ser Leu Glu Arg Ala Glu Asn Ser Ser Thr Glu Pro Ala
145                 150                 155                 160

Lys Ala Ile Lys Pro Ile Asp Arg Lys Ser Val His Gln Ile Cys Ser
                165                 170                 175

Gly Pro Val Val Pro Ser Leu Arg Pro Asn Ala Val Lys Glu Leu Val
            180                 185                 190

Glu Asn Ser Leu Asp Ala Gly Ala Thr Asn Val Asp Leu Lys Leu Lys
        195                 200                 205

Asp Tyr Gly Val Asp Leu Ile Glu Val Ser Gly Asn Gly Cys Gly Val
    210                 215                 220

Glu Glu Glu Asn Phe Glu Gly Phe Thr Leu Lys His His Thr Cys Lys
225                 230                 235                 240

Ile Gln Glu Phe Ala Asp Leu Thr Gln Val Glu Thr Phe Gly Phe Arg
                245                 250                 255

Gly Glu Ala Leu Ser Ser Leu Cys Ala Leu Ser Asp Val Thr Ile Ser
            260                 265                 270

Thr Cys Arg Val Ser Ala Lys Val Gly Thr Arg Leu Val Phe Asp His
        275                 280                 285

Tyr Gly Lys Ile Ile Gln Lys Thr Pro Tyr Pro Arg Pro Arg Gly Met
    290                 295                 300

Thr Val Ser Val Lys Gln Leu Phe Ser Thr Leu Pro Val His His Lys
305                 310                 315                 320

Glu Phe Gln Arg Asn Ile Lys Lys Lys Arg Ala Cys Phe Pro Phe Ala
                325                 330                 335

Phe Cys Arg Asp Cys Gln Phe Pro Glu Ala Ser Pro Ala Met Leu Pro
            340                 345                 350

Val Gln Pro Val Glu Leu Thr Pro Arg Ser Thr Pro His Pro Cys
        355                 360                 365

Ser Leu Glu Asp Asn Val Ile Thr Val Phe Ser Ser Val Lys Asn Gly
    370                 375                 380

Pro Gly Ser Ser Arg
385

<210> SEQ ID NO 9
<211> LENGTH: 1785
<212> TYPE: DNA
<213> ORGANISM: Homo sapiens

<400> SEQUENCE: 9

| | | | | | |
|---|---|---|---|---|---:|
| tttttagaaa | ctgatgttta | ttttccatca | accatttttc | catgctgctt | aagagaatat | 60 |
| gcaagaacag | cttaagacca | gtcagtggtt | gctcctaccc | attcagtggc | ctgagcagtg | 120 |
| gggagctgca | gaccagtctt | ccgtggcagg | ctgagcgctc | cagtcttcag | tagggaattg | 180 |
| ctgaataggc | acagagggca | cctgtacacc | ttcagaccag | tctgcaacct | caggctgagt | 240 |
| agcagtgaac | tcaggagcgg | gagcagtcca | ttcaccctga | aattcctcct | tggtcactgc | 300 |
| cttctcagca | gcagcctgct | cttcttttc | aatctcttca | ggatctctgt | agaagtacag | 360 |
| atcaggcatg | acctcccatg | ggtgttcacg | ggaaatggtg | ccacgcatgc | gcagaacttc | 420 |
| ccgagccagc | atccaccaca | ttaaacccac | tgagtgagct | cccttgttgt | tgcatgggat | 480 |
| ggcaatgtcc | acatagcgca | gaggagaatc | tgtgttacac | agcgcaatgg | taggtaggtt | 540 |
| aacataagat | gcctccgtga | gaggcgaagg | ggcggcggga | cccgggcctg | gcccgtatgt | 600 |
| gtccttggcg | gcctagacta | ggccgtcgct | gtatggtgag | ccccagggag | gcggatctgg | 660 |
| gcccccagaa | ggacacccgc | ctggatttgc | cccgtagccc | ggcccgggcc | ctcgggagc | 720 |
| agaacagcct | tggtgaggtg | gacaggaggg | gacctcgcga | gcagacgcgc | gcgccagcga | 780 |
| cagcagcccc | gccccggcct | ctcgggagcc | gggggcaga | ggctgcggag | ccccaggagg | 840 |
| gtctatcagc | cacagtctct | gcatgtttcc | aagagcaaca | ggaaatgaac | acattgcagg | 900 |
| ggccagtgtc | attcaaagat | gtggctgtgg | atttcaccca | ggaggagtgg | cggcaactgg | 960 |
| accctgatga | gaagatagca | tacggggatg | tgatgttgga | gaactacagc | catctagttt | 1020 |
| ctgtggggta | tgattatcac | caagccaaac | atcatcatgg | agtggaggtg | aaggaagtgg | 1080 |
| agcagggaga | ggagccgtgg | ataatggaag | gtgaatttcc | atgtcaacat | agtccagaac | 1140 |
| ctgctaaggc | catcaaacct | attgatcgga | agtcagtcca | tcagatttgc | tctgggccag | 1200 |
| tggtactgag | tctaagcact | gcagtgaagg | agttagtaga | aaacagtctg | gatgctggtg | 1260 |
| ccactaatat | tgatctaaag | cttaaggact | atggagtgga | tctcattgaa | gtttcagaca | 1320 |
| atggatgtgg | ggtagaagaa | gaaaactttg | aaggcttaat | ctctttcagc | tctgaaacat | 1380 |
| cacacatgta | agattcaaga | gtttgccgac | ctaactgaag | ttgaaacttt | cggttttcag | 1440 |
| ggggaagctc | tgagctcact | gtgtgcactg | agcgatgtca | ccatttctac | ctgccacgcg | 1500 |
| ttggtgaagg | ttgggactcg | actggtgttt | gatcacgatg | ggaaaatcat | ccaggaaacc | 1560 |
| ccctaccccc | accccagagg | gaccacagtc | agcgtgaagc | agttatttc | tacgctacct | 1620 |
| gtgcgccata | aggaatttca | aaggaatatt | aagaagacgt | gcctgcttcc | ccttcgcctt | 1680 |
| ctgccgtgat | tgtcagtttc | ctgaggcctc | cccagccatg | cttcctgtac | agcctgcaga | 1740 |
| actgtgagtc | aattaaacct | cttttcttca | taaattaaaa | aaaaa | | 1785 |

<210> SEQ ID NO 10
<211> LENGTH: 264
<212> TYPE: PRT
<213> ORGANISM: Homo sapiens

<400> SEQUENCE: 10

-continued

```
Met Cys Pro Trp Arg Pro Arg Leu Gly Arg Arg Cys Met Val Ser Pro
1               5                   10                  15

Arg Glu Ala Asp Leu Gly Pro Gln Lys Asp Thr Arg Leu Asp Leu Pro
            20                  25                  30

Arg Ser Pro Ala Arg Ala Pro Arg Glu Gln Asn Ser Leu Gly Glu Val
        35                  40                  45

Asp Arg Arg Gly Pro Arg Glu Gln Thr Arg Ala Pro Ala Thr Ala Ala
    50                  55                  60

Pro Pro Arg Pro Leu Gly Ser Arg Gly Ala Glu Ala Ala Glu Pro Gln
65                  70                  75                  80

Glu Gly Leu Ser Ala Thr Val Ser Ala Cys Phe Gln Glu Gln Gln Glu
                85                  90                  95

Met Asn Thr Leu Gln Gly Pro Val Ser Phe Lys Asp Val Ala Val Asp
            100                 105                 110

Phe Thr Gln Glu Glu Trp Arg Gln Leu Asp Pro Asp Glu Lys Ile Ala
        115                 120                 125

Tyr Gly Asp Val Met Leu Glu Asn Tyr Ser His Leu Val Ser Val Gly
    130                 135                 140

Tyr Asp Tyr His Gln Ala Lys His His His Gly Val Glu Val Lys Glu
145                 150                 155                 160

Val Glu Gln Gly Glu Pro Trp Ile Met Glu Gly Glu Phe Pro Cys
                165                 170                 175

Gln His Ser Pro Glu Pro Ala Lys Ala Ile Lys Pro Ile Asp Arg Lys
            180                 185                 190

Ser Val His Gln Ile Cys Ser Gly Pro Val Val Leu Ser Leu Ser Thr
        195                 200                 205

Ala Val Lys Glu Leu Val Glu Asn Ser Leu Asp Ala Gly Ala Thr Asn
    210                 215                 220

Ile Asp Leu Lys Leu Lys Asp Tyr Gly Val Asp Leu Ile Glu Val Ser
225                 230                 235                 240

Asp Asn Gly Cys Gly Val Glu Glu Glu Asn Phe Glu Gly Leu Ile Ser
                245                 250                 255

Phe Ser Ser Glu Thr Ser His Met
            260
```

<210> SEQ ID NO 11
<211> LENGTH: 2271
<212> TYPE: DNA
<213> ORGANISM: Homo sapiens

<400> SEQUENCE: 11

```
atgtcgttcg tggcaggggt tattcggcgg ctggacgaga cagtggtgaa ccgcatcgcg    60 gcggggggaag ttatccagcg gccagctaat gctatcaaag agatgattga aactgtttta   120
gatgcaaaat ccacaagtat tcaagtgatt gttaaagagg gaggcctgaa gttgattcag   180
atccaagaca tggcaccggg gatcaggaaa gaagatctgg atattgtatg tgaaaggttc   240
actactagta aactgcagtc ctttgaggat ttagccagta tttctaccta tggctttcga   300
ggtgaggctt ggccagcat aagccatgtg gctcatgtta ctattacaac gaaaacagct   360
gatggaaagt gtgcatacag agcaagttac tcagatggaa aactgaaagc ccctcctaaa   420
ccatgtgctg gcaatcaagg gacccagatc acggtggagg accttttttta caacatagcc   480 acgaggagaa aagctttaaa aaatccaagt gaagaatatg ggaaaatttt ggaagttgtt   540
ggcaggtatt cagtacacaa tgcaggcatt agtttctcag ttaaaaaaca aggagagaca   600
```

-continued

```
gtagctgatg ttaggacact acccaatgcc tcaaccgtgg acaatattcg ctccatcttt      660
ggaaatgctg ttagtcgaga actgatagaa attggatgtg aggataaaac cctagccttc      720
aaaatgaatg gttacatatc caatgcaaac tactcagtga agaagtgcat cttcttactc      780
ttcatcaacc atcgtctggt agaatcaact tccttgagaa aagccataga aacagtgtat      840
gcagcctatt tgcccaaaaa cacacaccca ttcctgtacc tcagtttaga aatcagtccc      900
cagaatgtgg atgttaatgt gcaccccaca aagcatgaag ttcacttcct gcacgaggag      960
agcatcctgg agcgggtgca gcagcacatc gagagcaagc tcctgggctc caattcctcc     1020
aggatgtact tcacccagac tttgctacca ggacttgctg gcccctctgg ggagatggtt     1080
aaatccacaa caagtctgac ctcgtcttct acttctggaa gtagtgataa ggtctatgcc     1140
caccagatgg ttcgtacaga ttcccgggaa cagaagcttg atgcatttct gcagcctctg     1200
agcaaacccc tgtccagtca gccccaggcc attgtcacag aggataagac agatatttct     1260
agtggcaggg ctaggcagca agatgaggag atgcttgaac tcccagcccc tgctgaagtg     1320
gctgccaaaa atcagagctt ggaggggat acaacaaagg ggacttcaga aatgtcagag      1380
aagagaggac ctacttccag caaccccaga aagagacatc gggaagattc tgatgtggaa     1440
atggtggaag atgattcccg aaaggaaatg actgcagctt gtaccccccg gagaaggatc     1500
attaacctca ctagtgtttt gagtctccag gaagaaatta atgagcaggg acatgaggtt     1560
ctccgggaga tgttgcataa ccactccttc gtgggctgtg tgaatcctca gtgggccttg     1620
gcacagcatc aaaccaagtt ataccttctc aacaccacca agcttagtga agaactgttc     1680
taccagatac tcatttatga ttttgccaat tttggtgttc tcaggttatc ggagccagca     1740
ccgctctttg accttgccat gcttgcctta gatagtccag agagtggctg gacagaggaa     1800
gatggtccca agaaggact tgctgaatac attgttgagt ttctgaagaa gaaggctgag      1860
atgcttgcag actatttctc tttggaaatt gatgaggaag gaacctgat tggattaccc      1920 cttctgattg acaactatgt gcccccttg gagggactgc ctatcttcat tcttcgacta      1980
gccactgagg tgaattggga cgaagaaaag gaatgttttg aaagcctcag taagaatgc      2040 gctatgttct attccatccg gaagcagtac atatctgagg agtcgaccct ctcaggccag     2100
cagagtgaag tgcctggctc cattccaaac tcctggaagt ggactgtgga acacattgtc     2160
tataaagcct tgcgctcaca cattctgcct cctaaacatt tcacagaaga tggaaatatc     2220
ctgcagcttg ctaacctgcc tgatctatac aaagtctttg agaggtgtta a              2271
```

<210> SEQ ID NO 12
<211> LENGTH: 756
<212> TYPE: PRT
<213> ORGANISM: Homo sapiens

<400> SEQUENCE: 12

```
Met Ser Phe Val Ala Gly Val Ile Arg Arg Leu Asp Glu Thr Val Val
1               5                   10                  15

Asn Arg Ile Ala Ala Gly Glu Val Ile Gln Arg Pro Ala Asn Ala Ile
            20                  25                  30

Lys Glu Met Ile Glu Asn Cys Leu Asp Ala Lys Ser Thr Ser Ile Gln
        35                  40                  45

Val Ile Val Lys Glu Gly Gly Leu Lys Leu Ile Gln Ile Gln Asp Asn
    50                  55                  60

Gly Thr Gly Ile Arg Lys Glu Asp Leu Asp Ile Val Cys Glu Arg Phe
65                  70                  75                  80
```

-continued

```
Thr Thr Ser Lys Leu Gln Ser Phe Glu Asp Leu Ala Ser Ile Ser Thr
            85                  90                  95

Tyr Gly Phe Arg Gly Glu Ala Leu Ala Ser Ile Ser His Val Ala His
            100                 105                 110

Val Thr Ile Thr Thr Lys Thr Ala Asp Gly Lys Cys Ala Tyr Arg Ala
            115                 120                 125

Ser Tyr Ser Asp Gly Lys Leu Lys Ala Pro Pro Lys Pro Cys Ala Gly
    130                 135                 140

Asn Gln Gly Thr Gln Ile Thr Val Glu Asp Leu Phe Tyr Asn Ile Ala
145                 150                 155                 160

Thr Arg Arg Lys Ala Leu Lys Asn Pro Ser Glu Glu Tyr Gly Lys Ile
                165                 170                 175

Leu Glu Val Val Gly Arg Tyr Ser Val His Asn Ala Gly Ile Ser Phe
            180                 185                 190

Ser Val Lys Lys Gln Gly Glu Thr Val Ala Asp Val Arg Thr Leu Pro
    195                 200                 205

Asn Ala Ser Thr Val Asp Asn Ile Arg Ser Ile Phe Gly Asn Ala Val
    210                 215                 220

Ser Arg Glu Leu Ile Glu Ile Gly Cys Glu Asp Lys Thr Leu Ala Phe
225                 230                 235                 240

Lys Met Asn Gly Tyr Ile Ser Asn Ala Asn Tyr Ser Val Lys Lys Cys
                245                 250                 255

Ile Phe Leu Leu Phe Ile Asn His Arg Leu Val Glu Ser Thr Ser Leu
            260                 265                 270

Arg Lys Ala Ile Glu Thr Val Tyr Ala Ala Tyr Leu Pro Lys Asn Thr
    275                 280                 285

His Pro Phe Leu Tyr Leu Ser Leu Glu Ile Ser Pro Gln Asn Val Asp
    290                 295                 300

Val Asn Val His Pro Thr Lys His Glu Val His Phe Leu His Glu Glu
305                 310                 315                 320

Ser Ile Leu Glu Arg Val Gln Gln His Ile Glu Ser Lys Leu Leu Gly
                325                 330                 335

Ser Asn Ser Ser Arg Met Tyr Phe Thr Gln Thr Leu Leu Pro Gly Leu
            340                 345                 350

Ala Gly Pro Ser Gly Glu Met Val Lys Ser Thr Thr Ser Leu Thr Ser
    355                 360                 365

Ser Ser Thr Ser Gly Ser Ser Asp Lys Val Tyr Ala His Gln Met Val
    370                 375                 380

Arg Thr Asp Ser Arg Glu Gln Lys Leu Asp Ala Phe Leu Gln Pro Leu
385                 390                 395                 400

Ser Lys Pro Leu Ser Ser Gln Pro Gln Ala Ile Val Thr Glu Asp Lys
                405                 410                 415

Thr Asp Ile Ser Ser Gly Arg Ala Arg Gln Gln Asp Glu Glu Met Leu
            420                 425                 430

Glu Leu Pro Ala Pro Ala Glu Val Ala Ala Lys Asn Gln Ser Leu Glu
    435                 440                 445

Gly Asp Thr Thr Lys Gly Thr Ser Glu Met Ser Glu Lys Arg Gly Pro
    450                 455                 460

Thr Ser Ser Asn Pro Arg Lys Arg His Arg Glu Asp Ser Asp Val Glu
465                 470                 475                 480

Met Val Glu Asp Asp Ser Arg Lys Glu Met Thr Ala Ala Cys Thr Pro
                485                 490                 495
```

```
Arg Arg Arg Ile Ile Asn Leu Thr Ser Val Leu Ser Leu Gln Glu Glu
            500                 505                 510
Ile Asn Glu Gln Gly His Glu Val Leu Arg Glu Met Leu His Asn His
            515                 520                 525
Ser Phe Val Gly Cys Val Asn Pro Gln Trp Ala Leu Ala Gln His Gln
            530                 535                 540
Thr Lys Leu Tyr Leu Leu Asn Thr Thr Lys Leu Ser Glu Glu Leu Phe
545                 550                 555                 560
Tyr Gln Ile Leu Ile Tyr Asp Phe Ala Asn Phe Gly Val Leu Arg Leu
                565                 570                 575
Ser Glu Pro Ala Pro Leu Phe Asp Leu Ala Met Leu Ala Leu Asp Ser
            580                 585                 590
Pro Glu Ser Gly Trp Thr Glu Glu Asp Gly Pro Lys Glu Gly Leu Ala
            595                 600                 605
Glu Tyr Ile Val Glu Phe Leu Lys Lys Lys Ala Glu Met Leu Ala Asp
            610                 615                 620
Tyr Phe Ser Leu Glu Ile Asp Glu Glu Gly Asn Leu Ile Gly Leu Pro
625                 630                 635                 640
Leu Leu Ile Asp Asn Tyr Val Pro Pro Leu Glu Gly Leu Pro Ile Phe
                645                 650                 655
Ile Leu Arg Leu Ala Thr Glu Val Asn Trp Asp Glu Glu Lys Glu Cys
            660                 665                 670
Phe Glu Ser Leu Ser Lys Glu Cys Ala Met Phe Tyr Ser Ile Arg Lys
            675                 680                 685
Gln Tyr Ile Ser Glu Glu Ser Thr Leu Ser Gly Gln Gln Ser Glu Val
            690                 695                 700
Pro Gly Ser Ile Pro Asn Ser Trp Lys Trp Thr Val Glu His Ile Val
705                 710                 715                 720
Tyr Lys Ala Leu Arg Ser His Ile Leu Pro Pro Lys His Phe Thr Glu
                725                 730                 735
Asp Gly Asn Ile Leu Gln Leu Ala Asn Leu Pro Asp Leu Tyr Lys Val
            740                 745                 750
Phe Glu Arg Cys
            755

<210> SEQ ID NO 13
<211> LENGTH: 4895
<212> TYPE: DNA
<213> ORGANISM: Homo sapiens

<400> SEQUENCE: 13
gtcggcgtcc gaggcggttg gtgtcggaga atttgttaag cgggactcca ggcaattatt      60
tccagtcaga gaaggaaacc agtgcctggc attctcacca tctttctacc taccatgatc     120
aagtgcttgt cagttgaagt acaagccaaa ttgcgttctg gtttggccat aagctccttg     180
ggccaatgtg ttgaggaact tgccctcaac agtattgatg ctgaagcaaa atgtgtggct     240
gtcagggtga atatggaaac cttccaagtt caagtgatag acaatggatt tgggatgggg     300
agtgatgatg tagagaaagt gggaaatcgt tatttcacca gtaaatgcca ctcggtacag     360
gacttggaga atccaaggtt ttatggtttc cgaggagagg ccttggcaaa tattgctgac     420
atggccagtg ctgtggaaat ttcgtccaag aaaaacagga caatgaaaac ttttgtgaaa     480
ctgtttcaga gtgaaaaagc cctgaaagct tgtgaagctg atgtgactag agcaagcgct     540
gggactactg taacagtgta taacctattt taccagcttc ctgtaaggag gaaatgcatg     600
```

```
gaccctagac tggagtttga gaaggttagg cagagaatag aagctctctc actcatgcac    660
ccttccattt cttctctttt gagaaatgat gtttctggtt ccatggttct tcagctccct    720
aaaaccaaag acgtatgttc ccgattttgt caaatttatg gattgggaaa gtcccaaaag    780
ctaagagaaa taagttttaa atataaagag tttgagctta gtggctatat cagctctgaa    840
gcacattaca acaagaatat gcagtttttg tttgtgaaca aaagactagt tttaaggaca    900
aagctacata aactcattga ctttttatta aggaaagaaa gtattatatg caagccaaag    960
aatggtccca ccagtaggca aatgaattca agtcttcggc accggtctac cccagaactc   1020
tatggcatat atgtaattaa tgtgcagtgc caattctgtg agtatgatgt gtgcatggag   1080
ccagccaaaa ctctgattga atttcagaac tgggacactc tcttgttttg cattcaggaa   1140
ggagtgaaaa tgttttttaaa gcaagaaaaa ttatttgtgg aattatcagg tgaggatatt   1200
aaggaattta gtgaagataa tggttttagt ttatttgatg ctactcttca gaagcgtgtg   1260
acttccgatg agaggagcaa tttccaggaa gcatgtaata atattttaga ttcctatgag   1320
atgtttaatt tgcagtcaaa agctgtgaaa agaaaaacta ctgcagaaaa cgtaaacaca   1380
cagagttcta gggattcaga agctaccaga aaaaatacaa atgatgcatt tttgtacatt   1440
tatgaatcag gtggtccagg ccatagcaaa atgacagagc catctttaca aaacaaagac   1500
agctcttgct cagaatcaaa gatgttagaa caagagacaa ttgtagcatc agaagctggt   1560
gaaaatgaga acataaaaa atctttcctg gaacgtagct ctttagaaaa tccgtgtgga   1620
accagtttag aaatgttttt aagccctttt cagacaccat gtcactttga ggagagtggg   1680
caggatctag aaatatggaa agaaagtact actgttaatg gcatggctgc caacatcttg   1740
aaaaataata gaattcagaa tcaaccaaag agatttaaag atgctactga agtgggatgc   1800
cagcctctgc cttttgcaac aacattatgg ggagtacata gtgctcagac agagaaagag   1860
aaaaaaaaag aatctagcaa ttgtggaaga agaaatgttt ttagttatgg gcgagttaaa   1920
ttatgttcca ctggctttat aactcatgta gtacaaaatg aaaaaactaa atcaactgaa   1980
acagaacatt catttaaaaa ttatgttaga cctggtccca cacgtgccca agaaacattt   2040
ggaaatagaa cacgtcattc agttgaaact ccagacatca aagatttagc cagcacttta   2100
agtaaagaat ctggtcaatt gcccaacaaa aaaaattgca gaacgaatat aagttatggg   2160
ctagagaatg aacctacagc aacttataca atgttttctg cttttcagga aggtagcaaa   2220
aaatcacaaa cagattgcat attatctgat acatcccccct ctttccctg gtatagacac   2280 gtttccaatg atagtaggaa aacagataaa ttaattggtt tctccaaacc aatcgtccgt   2340
aagaagctaa gcttgagttc acagctagga tctttagaga agtttaagag gcaatatggg   2400
aaggttgaaa atcctctgga tacagaagta gaggaaagta atggagtcac taccaatctc   2460
agtcttcaag ttgaacctga cattctgctg aaggacaaga accgcttaga gaactctgat   2520
gtttgtaaaa tcactactat ggagcatagt gattcagata gtagttgtca accagcaagc   2580
cacatccttg actcagagaa gtttccattc tccaaggatg aagattgttt agaacaacag   2640
atgcctagtt tgagagaaag tcctatgacc ctgaaggagt tatctctctt taatagaaaa   2700
cctttggacc ttgagaagtc atctgaatca ctagcctcta aattatccag actgaagggt   2760
tccgaaagag aaactcaaac aatggggatg atgagtcgtt ttaatgaact tccaaattca   2820
gattccagta ggaaagacag caagttgtgc agtgtgttaa cacaagattt tgtatgttta   2880
tttaacaaca agcatgaaaa aacagagaat ggtgtcatcc caacatcaga ttctgccaca   2940
caggataatt cctttaataa aaatagtaaa acacattcta acagcaatac aacagagaac   3000
```

```
tgtgtgatat cagaaactcc tttggtattg ccctataata attctaaagt taccggtaaa    3060
gattcagatg ttcttatcag agcctcagaa caacagatag gaagtcttga ctctcccagt    3120
ggaatgttaa tgaatccggt agaagatgcc acaggtgacc aaaatggaat tgttttcag     3180 agtgaggaat ctaaagcaag agcttgttct gaaactgaag agtcaaacac gtgttgttca    3240
gattggcagc ggcatttcga tgtagccctg gaagaatgg tttatgtcaa caaaatgact    3300
ggactcagca cattcattgc cccaactgag gacattcagg ctgcttgtac taaagacctg    3360
acaactgtgg ctgtggatgt tgtacttgag aatgggtctc agtacaggtg tcaaccttt     3420 agaagcgacc ttgttcttcc tttccttccg agagctcgag cagagaggac tgtgatgaga    3480
caggataaca gagatactgt ggatgatact gttagtagcg aatcgcttca gtctttgttc    3540
tcagaatggg acaatccagt atttgcccgt tatccagagg ttgctgttga tgtaagcagt    3600
ggccaggctg agagcttagc agttaaaatt cacaacatct tgtatcccta tcgtttcacc    3660
aaaggaatga ttcattcaat gcaggttctc cagcaagtag ataacaagtt tattgcctgt    3720
ttgatgagca ctaagactga agagaatggc gaggcagatt cctacagaa gcaacaggca    3780 caaggctctg gtcggaaaaa attactgtct tctactctaa ttcctccgct agagataaca    3840
gtgacagagg aacaaaggag actcttatgg tgttaccaca aaaatctgga agatctgggc    3900
cttgaatttg tatttccaga cactagtgat tctctggtcc ttgtgggaaa agtaccacta    3960
tgttttgtgg aaagagaagc caatgaactt cggagaggaa gatctactgt gaccaagagt    4020
attgtggagg aatttatccg agaacaactg gagctactcc agaccaccgg aggcatccaa    4080
gggacattgc cactgactgt ccagaaggtg ttggcatccc aagcctgcca tggggccatt    4140
aagtttaatg atggcctgag cttacaggaa agttgccgcc ttattgaagc tctgtcctca    4200
tgccagctgc cattccagtg tgctcacggg agaccttcta tgctgccgtt agctgacata    4260
gaccacttgg aacaggaaaa acagattaaa cccaacctca ctaaacttcg caaaatggcc    4320
caggcctggc gtctctttgg aaaagcagag tgtgatacaa ggcagagcct gcagcagtcc    4380
atgcctccct gtgagccacc atgagaacag aatcactggt ctaaaaggaa caagggatg    4440 ttcactgtat gcctctgagc agagagcagc agcagcaggt accagcacgg ccctgactga    4500
atcagcccag tgtccctgag cagcttagac agcagggctc tctgtatcag tctttcttga    4560
gcagatgatt cccctagttg agtagccaga tgaaattcaa gcctaaagac aattcattca    4620
tttgcatcca tgggcacaga aggttgctat atagtatcta ccttttgcta cttatttaat    4680
gataaaattt aatgacagtt taaaaaaaaa aaaaaaaaa attatttgaa ggggtgggtg     4740 attttttgttt ttgtacagtt ttttttcaag cttcacattt gcgtgtatct aattcagctg    4800
atgctcaagt ccaaggggta gtctgccttc ccaggctgcc cccagggttt ctgcactggt    4860
cccctctttt cccttcagtc ttcttcactt ccctt                                4895
```

<210> SEQ ID NO 14
<211> LENGTH: 1429
<212> TYPE: PRT
<213> ORGANISM: Homo sapiens

<400> SEQUENCE: 14

```
Met Ile Lys Cys Leu Ser Val Glu Val Gln Ala Lys Leu Arg Ser Gly
1               5                   10                  15

Leu Ala Ile Ser Ser Leu Gly Gln Cys Val Glu Glu Leu Ala Leu Asn
            20                  25                  30
```

-continued

```
Ser Ile Asp Ala Glu Ala Lys Cys Val Ala Val Arg Val Asn Met Glu
        35                  40                  45
Thr Phe Gln Val Gln Val Ile Asp Asn Gly Phe Gly Met Gly Ser Asp
    50                  55                  60
Asp Val Glu Lys Val Gly Asn Arg Tyr Phe Thr Ser Lys Cys His Ser
65                  70                  75                  80
Val Gln Asp Leu Glu Asn Pro Arg Phe Tyr Gly Phe Arg Gly Glu Ala
                85                  90                  95
Leu Ala Asn Ile Ala Asp Met Ala Ser Ala Val Glu Ile Ser Ser Lys
            100                 105                 110
Lys Asn Arg Thr Met Lys Thr Phe Val Lys Leu Phe Gln Ser Gly Lys
        115                 120                 125
Ala Leu Lys Ala Cys Glu Ala Asp Val Thr Arg Ala Ser Ala Gly Thr
    130                 135                 140
Thr Val Thr Val Tyr Asn Leu Phe Tyr Gln Leu Pro Val Arg Arg Lys
145                 150                 155                 160
Cys Met Asp Pro Arg Leu Glu Phe Glu Lys Val Arg Gln Arg Ile Glu
                165                 170                 175
Ala Leu Ser Leu Met His Pro Ser Ile Ser Phe Ser Leu Arg Asn Asp
            180                 185                 190
Val Ser Gly Ser Met Val Leu Gln Leu Pro Lys Thr Lys Asp Val Cys
        195                 200                 205
Ser Arg Phe Cys Gln Ile Tyr Gly Leu Gly Lys Ser Gln Lys Leu Arg
    210                 215                 220
Glu Ile Ser Phe Lys Tyr Lys Glu Phe Glu Leu Ser Gly Tyr Ile Ser
225                 230                 235                 240
Ser Glu Ala His Tyr Asn Lys Asn Met Gln Phe Leu Phe Val Asn Lys
                245                 250                 255
Arg Leu Val Leu Arg Thr Lys Leu His Lys Leu Ile Asp Phe Leu Leu
            260                 265                 270
Arg Lys Glu Ser Ile Ile Cys Lys Pro Lys Asn Gly Pro Thr Ser Arg
        275                 280                 285
Gln Met Asn Ser Ser Leu Arg His Arg Ser Thr Pro Glu Leu Tyr Gly
    290                 295                 300
Ile Tyr Val Ile Asn Val Gln Cys Gln Phe Cys Glu Tyr Asp Val Cys
305                 310                 315                 320
Met Glu Pro Ala Lys Thr Leu Ile Glu Phe Gln Asn Trp Asp Thr Leu
                325                 330                 335
Leu Phe Cys Ile Gln Glu Gly Val Lys Met Phe Leu Lys Gln Glu Lys
            340                 345                 350
Leu Phe Val Glu Leu Ser Gly Glu Asp Ile Lys Glu Phe Ser Glu Asp
        355                 360                 365
Asn Gly Phe Ser Leu Phe Asp Ala Thr Leu Gln Lys Arg Val Thr Ser
    370                 375                 380
Asp Glu Arg Ser Asn Phe Gln Glu Ala Cys Asn Asn Ile Leu Asp Ser
385                 390                 395                 400
Tyr Glu Met Phe Asn Leu Gln Ser Lys Ala Val Lys Arg Lys Thr Thr
                405                 410                 415
Ala Glu Asn Val Asn Thr Gln Ser Ser Arg Asp Ser Glu Ala Thr Arg
            420                 425                 430
Lys Asn Thr Asn Asp Ala Phe Leu Tyr Ile Tyr Glu Ser Gly Gly Pro
        435                 440                 445
Gly His Ser Lys Met Thr Glu Pro Ser Leu Gln Asn Lys Asp Ser Ser
```

-continued

```
        450                 455                 460
Cys Ser Glu Ser Lys Met Leu Glu Gln Glu Thr Ile Val Ala Ser Glu
465                 470                 475                 480

Ala Gly Glu Asn Glu Lys His Lys Lys Ser Phe Leu Glu Arg Ser Ser
                485                 490                 495

Leu Glu Asn Pro Cys Gly Thr Ser Leu Glu Met Phe Leu Ser Pro Phe
            500                 505                 510

Gln Thr Pro Cys His Phe Glu Glu Ser Gly Gln Asp Leu Glu Ile Trp
        515                 520                 525

Lys Glu Ser Thr Thr Val Asn Gly Met Ala Ala Asn Ile Leu Lys Asn
530                 535                 540

Asn Arg Ile Gln Asn Gln Pro Lys Arg Phe Lys Asp Ala Thr Glu Val
545                 550                 555                 560

Gly Cys Gln Pro Leu Pro Phe Ala Thr Thr Leu Trp Gly Val His Ser
                565                 570                 575

Ala Gln Thr Glu Lys Glu Lys Lys Glu Ser Ser Asn Cys Gly Arg
                580                 585                 590

Arg Asn Val Phe Ser Tyr Gly Arg Val Lys Leu Cys Ser Thr Gly Phe
                595                 600                 605

Ile Thr His Val Val Gln Asn Glu Lys Thr Lys Ser Thr Glu Thr Glu
            610                 615                 620

His Ser Phe Lys Asn Tyr Val Arg Pro Gly Pro Thr Arg Ala Gln Glu
625                 630                 635                 640

Thr Phe Gly Asn Arg Thr Arg His Ser Val Glu Thr Pro Asp Ile Lys
                645                 650                 655

Asp Leu Ala Ser Thr Leu Ser Lys Glu Ser Gly Gln Leu Pro Asn Lys
            660                 665                 670

Lys Asn Cys Arg Thr Asn Ile Ser Tyr Gly Leu Glu Asn Glu Pro Thr
        675                 680                 685

Ala Thr Tyr Thr Met Phe Ser Ala Phe Gln Glu Gly Ser Lys Lys Ser
            690                 695                 700

Gln Thr Asp Cys Ile Leu Ser Asp Thr Ser Pro Ser Phe Pro Trp Tyr
705                 710                 715                 720

Arg His Val Ser Asn Asp Ser Arg Lys Thr Asp Lys Leu Ile Gly Phe
                725                 730                 735

Ser Lys Pro Ile Val Arg Lys Lys Leu Ser Leu Ser Ser Gln Leu Gly
            740                 745                 750

Ser Leu Glu Lys Phe Lys Arg Gln Tyr Gly Lys Val Glu Asn Pro Leu
        755                 760                 765

Asp Thr Glu Val Glu Glu Ser Asn Gly Val Thr Thr Asn Leu Ser Leu
770                 775                 780

Gln Val Glu Pro Asp Ile Leu Leu Lys Asp Lys Asn Arg Leu Glu Asn
785                 790                 795                 800

Ser Asp Val Cys Lys Ile Thr Thr Met Glu His Ser Asp Ser Asp Ser
                805                 810                 815

Ser Cys Gln Pro Ala Ser His Ile Leu Asp Ser Glu Lys Phe Pro Phe
            820                 825                 830

Ser Lys Asp Glu Asp Cys Leu Glu Gln Gln Met Pro Ser Leu Arg Glu
        835                 840                 845

Ser Pro Met Thr Leu Lys Glu Leu Ser Leu Phe Asn Arg Lys Pro Leu
        850                 855                 860

Asp Leu Glu Lys Ser Ser Glu Ser Leu Ala Ser Lys Leu Ser Arg Leu
865                 870                 875                 880
```

```
Lys Gly Ser Glu Arg Glu Thr Gln Thr Met Gly Met Met Ser Arg Phe
            885                 890                 895
Asn Glu Leu Pro Asn Ser Asp Ser Ser Arg Lys Asp Ser Lys Leu Cys
            900                 905                 910
Ser Val Leu Thr Gln Asp Phe Cys Met Leu Phe Asn Asn Lys His Glu
            915                 920                 925
Lys Thr Glu Asn Gly Val Ile Pro Thr Asp Ser Ala Thr Gln Asp
    930                 935                 940
Asn Ser Phe Asn Lys Asn Ser Lys Thr His Ser Asn Ser Asn Thr Thr
945                 950                 955                 960
Glu Asn Cys Val Ile Ser Glu Thr Pro Leu Val Leu Pro Tyr Asn Asn
                965                 970                 975
Ser Lys Val Thr Gly Lys Asp Ser Asp Val Leu Ile Arg Ala Ser Glu
            980                 985                 990
Gln Gln Ile Gly Ser Leu Asp Ser Pro Ser Gly Met Leu Met Asn Pro
            995                 1000                1005
Val Glu Asp Ala Thr Gly Asp Gln Asn Gly Ile Cys Phe Gln Ser
    1010                1015                1020
Glu Glu Ser Lys Ala Arg Ala Cys Ser Glu Thr Glu Glu Ser Asn
    1025                1030                1035
Thr Cys Cys Ser Asp Trp Gln Arg His Phe Asp Val Ala Leu Gly
    1040                1045                1050
Arg Met Val Tyr Val Asn Lys Met Thr Gly Leu Ser Thr Phe Ile
    1055                1060                1065
Ala Pro Thr Glu Asp Ile Gln Ala Ala Cys Thr Lys Asp Leu Thr
    1070                1075                1080
Thr Val Ala Val Asp Val Val Leu Glu Asn Gly Ser Gln Tyr Arg
    1085                1090                1095
Cys Gln Pro Phe Arg Ser Asp Leu Val Leu Pro Phe Leu Pro Arg
    1100                1105                1110
Ala Arg Ala Glu Arg Thr Val Met Arg Gln Asp Asn Arg Asp Thr
    1115                1120                1125
Val Asp Asp Thr Val Ser Ser Glu Ser Leu Gln Ser Leu Phe Ser
    1130                1135                1140
Glu Trp Asp Asn Pro Val Phe Ala Arg Tyr Pro Glu Val Ala Val
    1145                1150                1155
Asp Val Ser Ser Gly Gln Ala Glu Ser Leu Ala Val Lys Ile His
    1160                1165                1170
Asn Ile Leu Tyr Pro Tyr Arg Phe Thr Lys Gly Met Ile His Ser
    1175                1180                1185
Met Gln Val Leu Gln Gln Val Asp Asn Lys Phe Ile Ala Cys Leu
    1190                1195                1200
Met Ser Thr Lys Thr Glu Glu Asn Gly Glu Ala Asp Ser Tyr Glu
    1205                1210                1215
Lys Gln Gln Ala Gln Gly Ser Gly Arg Lys Lys Leu Leu Ser Ser
    1220                1225                1230
Thr Leu Ile Pro Pro Leu Glu Ile Thr Val Thr Glu Glu Gln Arg
    1235                1240                1245
Arg Leu Leu Trp Cys Tyr His Lys Asn Leu Glu Asp Leu Gly Leu
    1250                1255                1260
Glu Phe Val Phe Pro Asp Thr Ser Asp Ser Leu Val Leu Val Gly
    1265                1270                1275
```

-continued

```
Lys Val Pro Leu Cys Phe Val Glu Arg Glu Ala Asn Glu Leu Arg
    1280            1285                1290

Arg Gly Arg Ser Thr Val Thr Lys Ser Ile Val Glu Glu Phe Ile
    1295            1300                1305

Arg Glu Gln Leu Glu Leu Leu Gln Thr Thr Gly Gly Ile Gln Gly
    1310            1315                1320

Thr Leu Pro Leu Thr Val Gln Lys Val Leu Ala Ser Gln Ala Cys
    1325            1330                1335

His Gly Ala Ile Lys Phe Asn Asp Gly Leu Ser Leu Gln Glu Ser
    1340            1345                1350

Cys Arg Leu Ile Glu Ala Leu Ser Ser Cys Gln Leu Pro Phe Gln
    1355            1360                1365

Cys Ala His Gly Arg Pro Ser Met Leu Pro Leu Ala Asp Ile Asp
    1370            1375                1380

His Leu Glu Gln Glu Lys Gln Ile Lys Pro Asn Leu Thr Lys Leu
    1385            1390                1395

Arg Lys Met Ala Gln Ala Trp Arg Leu Phe Gly Lys Ala Glu Cys
    1400            1405                1410

Asp Thr Arg Gln Ser Leu Gln Gln Ser Met Pro Pro Cys Glu Pro
    1415            1420                1425

Pro
```

<210> SEQ ID NO 15
<211> LENGTH: 3145
<212> TYPE: DNA
<213> ORGANISM: Homo sapiens

<400> SEQUENCE: 15

```
ggcgggaaac agcttagtgg gtgtgggggtc gcgcattttc ttcaaccagg aggtgaggag      60
gtttcgacat ggcggtgcag ccgaaggaga cgctgcagtt ggagagcgcg gccgaggtcg     120
gcttcgtgcg cttctttcag gcatgccgg agaagccgac caccacagtg cgccttttcg     180
accggggcga cttctatacg cgcacggcg aggacgcgct gctggccgcc cgggaggtgt     240
tcaagaccca gggggtgatc aagtacatgg ggccggcagg agcaaagaat ctgcagagtg     300
ttgtgcttag taaatgaat tttgaatctt ttgtaaaaga tcttcttctg gttcgtcagt     360
atagagttga agtttataag aatagagctg aaataaggc atccaaggag aatgattggt     420
atttggcata taaggcttct cctggcaatc tctctcagtt tgaagacatt ctctttggta     480
acaatgatat gtcagcttcc attggtgttg tgggtgttaa aatgtccgca gttgatggcc     540
agagacaggt tggagttggg tatgtggatt ccatacagag gaaactagga ctgtgtgaat     600
tccctgataa tgatcagttc tccaatcttg aggctctcct catccagatt ggaccaaagg     660
aatgtgtttt acccggagga gagactgctg agacatggg gaaactgaga cagataattc     720
aaagaggagg aattctgatc acagaaagaa aaaagctga cttttccaca aaagacattt     780
atcaggacct caaccggttg ttgaaaggca aaagggaga gcagatgaat agtgctgtat     840
tgccagaaat ggagaatcag gttgcagttt catcactgtc tgcggtaatc aagttttttag     900
aactcttatc agatgattcc aactttggac agtttgaact gactactttt gacttcagcc     960
agtatatgaa attggatatt gcagcagtca gagccctta cctttttcag ggttctgttg    1020
aagataccac tggctctcag tctctggctg ccttgctgaa taagtgtaaa acccctcaag    1080
gacaaagact tgttaaccag tggattaagc agctctcat ggataagaac agaatagagg    1140
agagattgaa tttagtggaa gcttttgtag aagatgcaga attgaggcag actttacaag    1200
```

-continued

```
aagatttact tcgtcgattc ccagatctta accgacttgc caagaagttt caaagacaag    1260
cagcaaactt acaagattgt taccgactct atcagggtat aaatcaacta cctaatgtta    1320
tacaggctct ggaaaaacat gaaggaaaac accagaaatt attgttggca gttttttgtga   1380 ctcctcttac tgatcttcgt tctgacttct ccaagtttca ggaaatgata gaaacaactt    1440
tagatatgga tcaggtggaa aaccatgaat tccttgtaaa accttcattt gatcctaatc    1500
tcagtgaatt aagagaaata atgaatgact tggaaaagaa gatgcagtca acattaataa    1560
gtgcagccag atcttggc ttggaccctg caaactgat taaactggat tccagtgcac       1620
agtttggata ttactttcgt gtaacctgta aggaagaaaa agtccttcgt aacaataaaa    1680
actttagtac tgtagatatc cagaagaatg gtgttaaatt taccaacagc aaattgactt    1740
ctttaaatga agagtatacc aaaaataaaa cagaatatga agaagcccag gatgccattg    1800
ttaaagaaat tgtcaatatt tcttcaggct atgtagaacc aatgcagaca ctcaatgatg    1860
tgttagctca gctagatgct gttgtcagct tgctcacgt gtcaaatgga gcacctgttc     1920
catatgtacg accagccatt ttggagaaag gacaaggaag aatttatatta aaagcatcca   1980 ggcatgcttg tgttgaagtt caagatgaaa ttgcatttat tcctaatgac gtatactttg    2040
aaaaagataa acagatgttc cacatcatta ctggccccaa tatgggaggt aaatcaacat    2100
atattcgaca aactggggtg atagtactca tggcccaaat tgggtgtttt gtgccatgtg    2160
agtcagcaga agtgtccatt gtggactgca tcttagcccg agtaggggct ggtgacagtc    2220
aattgaaagg agtctccacg ttcatggctg aaatgttgga aactgcttct atcctcaggt    2280
ctgcaaccaa agattcatta ataatcatag atgaattggg aagaggaact tctacctacg    2340
atggatttgg gttagcatgg gctatatcag aatacattgc aacaaagatt ggtgcttttt    2400
gcatgtttgc aacccatttt catgaactta ctgccttggc caatcagata ccaactgtta    2460
ataatctaca tgtcacagca ctcaccactg aagagacctt aactatgctt tatcaggtga    2520
agaaaggtgt ctgtgatcaa agttttggga ttcatgttgc agagcttgct aatttcccta    2580
agcatgtaat agagtgtgct aaacagaaag ccctggaact tgaggagttt cagtatattg    2640
gagaatcgca aggatatgat atcatggaac cagcagcaaa gaagtgctat ctggaaagag    2700
agcaaggtga aaaattatt caggagttcc tgtccaaggt gaaacaaatg ccctttactg      2760
aaatgtcaga agaaaacatc acaataaagt taaaacagct aaaagctgaa gtaatagcaa    2820
agaataatag ctttgtaaat gaaatcattt cacgaataaa agttactacg tgaaaaatcc    2880
cagtaatgga atgaaggtaa tattgataag ctattgtctg taatagttt atattgtttt     2940 atattaaccc ttttccata gtgttaactg tcagtgccca tgggctatca acttaataag     3000
atatttagta atattttact ttgaggacat tttcaaagat ttttattttg aaaaatgaga    3060
gctgtaactg aggactgttt gcaattgaca taggcaataa taagtgatgt gctgaatttt    3120
ataaataaaa tcatgtagtt tgtgg                                          3145
```

<210> SEQ ID NO 16
<211> LENGTH: 934
<212> TYPE: PRT
<213> ORGANISM: Homo sapiens

<400> SEQUENCE: 16

```
Met Ala Val Gln Pro Lys Glu Thr Leu Gln Leu Glu Ser Ala Ala Glu
 1               5                  10                  15

Val Gly Phe Val Arg Phe Phe Gln Gly Met Pro Glu Lys Pro Thr Thr
```

-continued

```
                20                  25                  30
Thr Val Arg Leu Phe Asp Arg Gly Asp Phe Tyr Thr Ala His Gly Glu
                35                  40                  45
Asp Ala Leu Leu Ala Ala Arg Glu Val Phe Lys Thr Gln Gly Val Ile
 50                  55                  60
Lys Tyr Met Gly Pro Ala Gly Ala Lys Asn Leu Gln Ser Val Val Leu
 65                  70                  75                  80
Ser Lys Met Asn Phe Glu Ser Phe Val Lys Asp Leu Leu Leu Val Arg
                 85                  90                  95
Gln Tyr Arg Val Glu Val Tyr Lys Asn Arg Ala Gly Asn Lys Ala Ser
                100                 105                 110
Lys Glu Asn Asp Trp Tyr Leu Ala Tyr Lys Ala Ser Pro Gly Asn Leu
                115                 120                 125
Ser Gln Phe Glu Asp Ile Leu Phe Gly Asn Asn Asp Met Ser Ala Ser
                130                 135                 140
Ile Gly Val Val Gly Val Lys Met Ser Ala Val Asp Gly Gln Arg Gln
145                 150                 155                 160
Val Gly Val Gly Tyr Val Asp Ser Ile Gln Arg Lys Leu Gly Leu Cys
                165                 170                 175
Glu Phe Pro Asp Asn Asp Gln Phe Ser Asn Leu Glu Ala Leu Leu Ile
                180                 185                 190
Gln Ile Gly Pro Lys Glu Cys Val Leu Pro Gly Gly Glu Thr Ala Gly
                195                 200                 205
Asp Met Gly Lys Leu Arg Gln Ile Ile Gln Arg Gly Gly Ile Leu Ile
                210                 215                 220
Thr Glu Arg Lys Lys Ala Asp Phe Ser Thr Lys Asp Ile Tyr Gln Asp
225                 230                 235                 240
Leu Asn Arg Leu Leu Lys Gly Lys Lys Gly Glu Gln Met Asn Ser Ala
                245                 250                 255
Val Leu Pro Glu Met Glu Asn Gln Val Ala Val Ser Ser Leu Ser Ala
                260                 265                 270
Val Ile Lys Phe Leu Glu Leu Leu Ser Asp Asp Ser Asn Phe Gly Gln
                275                 280                 285
Phe Glu Leu Thr Thr Phe Asp Phe Ser Gln Tyr Met Lys Leu Asp Ile
                290                 295                 300
Ala Ala Val Arg Ala Leu Asn Leu Phe Gln Gly Ser Val Glu Asp Thr
305                 310                 315                 320
Thr Gly Ser Gln Ser Leu Ala Ala Leu Leu Asn Lys Cys Lys Thr Pro
                325                 330                 335
Gln Gly Gln Arg Leu Val Asn Gln Trp Ile Lys Gln Pro Leu Met Asp
                340                 345                 350
Lys Asn Arg Ile Glu Glu Arg Leu Asn Leu Val Glu Ala Phe Val Glu
                355                 360                 365
Asp Ala Glu Leu Arg Gln Thr Leu Gln Glu Asp Leu Leu Arg Arg Phe
                370                 375                 380
Pro Asp Leu Asn Arg Leu Ala Lys Lys Phe Gln Arg Gln Ala Ala Asn
385                 390                 395                 400
Leu Gln Asp Cys Tyr Arg Leu Tyr Gln Gly Ile Asn Gln Leu Pro Asn
                405                 410                 415
Val Ile Gln Ala Leu Glu Lys His Glu Gly Lys His Gln Lys Leu Leu
                420                 425                 430
Leu Ala Val Phe Val Thr Pro Leu Thr Asp Leu Arg Ser Asp Phe Ser
                435                 440                 445
```

```
Lys Phe Gln Glu Met Ile Glu Thr Thr Leu Asp Met Asp Gln Val Glu
            450                 455                 460

Asn His Glu Phe Leu Val Lys Pro Ser Phe Asp Pro Asn Leu Ser Glu
465                 470                 475                 480

Leu Arg Glu Ile Met Asn Asp Leu Glu Lys Lys Met Gln Ser Thr Leu
                485                 490                 495

Ile Ser Ala Ala Arg Asp Leu Gly Leu Asp Pro Gly Lys Gln Ile Lys
            500                 505                 510

Leu Asp Ser Ser Ala Gln Phe Gly Tyr Tyr Phe Arg Val Thr Cys Lys
            515                 520                 525

Glu Glu Lys Val Leu Arg Asn Asn Lys Asn Phe Ser Thr Val Asp Ile
            530                 535                 540

Gln Lys Asn Gly Val Lys Phe Thr Asn Ser Lys Leu Thr Ser Leu Asn
545                 550                 555                 560

Glu Glu Tyr Thr Lys Asn Lys Thr Glu Tyr Glu Glu Ala Gln Asp Ala
                565                 570                 575

Ile Val Lys Glu Ile Val Asn Ile Ser Ser Gly Tyr Val Glu Pro Met
            580                 585                 590

Gln Thr Leu Asn Asp Val Leu Ala Gln Leu Asp Ala Val Val Ser Phe
            595                 600                 605

Ala His Val Ser Asn Gly Ala Pro Val Pro Tyr Val Arg Pro Ala Ile
            610                 615                 620

Leu Glu Lys Gly Gln Gly Arg Ile Ile Leu Lys Ala Ser Arg His Ala
625                 630                 635                 640

Cys Val Glu Val Gln Asp Glu Ile Ala Phe Ile Pro Asn Asp Val Tyr
                645                 650                 655

Phe Glu Lys Asp Lys Gln Met Phe His Ile Ile Thr Gly Pro Asn Met
                660                 665                 670

Gly Gly Lys Ser Thr Tyr Ile Arg Gln Thr Gly Val Ile Val Leu Met
            675                 680                 685

Ala Gln Ile Gly Cys Phe Val Pro Cys Glu Ser Ala Glu Val Ser Ile
            690                 695                 700

Val Asp Cys Ile Leu Ala Arg Val Gly Ala Gly Asp Ser Gln Leu Lys
705                 710                 715                 720

Gly Val Ser Thr Phe Met Ala Glu Met Leu Glu Thr Ala Ser Ile Leu
                725                 730                 735

Arg Ser Ala Thr Lys Asp Ser Leu Ile Ile Asp Glu Leu Gly Arg
                740                 745                 750

Gly Thr Ser Thr Tyr Asp Gly Phe Gly Leu Ala Trp Ala Ile Ser Glu
            755                 760                 765

Tyr Ile Ala Thr Lys Ile Gly Ala Phe Cys Met Phe Ala Thr His Phe
            770                 775                 780

His Glu Leu Thr Ala Leu Ala Asn Gln Ile Pro Thr Val Asn Asn Leu
785                 790                 795                 800

His Val Thr Ala Leu Thr Thr Glu Glu Thr Leu Thr Met Leu Tyr Gln
                805                 810                 815

Val Lys Lys Gly Val Cys Asp Gln Ser Phe Gly Ile His Val Ala Glu
            820                 825                 830

Leu Ala Asn Phe Pro Lys His Val Ile Glu Cys Ala Lys Gln Lys Ala
            835                 840                 845

Leu Glu Leu Glu Glu Phe Gln Tyr Ile Gly Glu Ser Gln Gly Tyr Asp
850                 855                 860
```

```
Ile Met Glu Pro Ala Ala Lys Lys Cys Tyr Leu Arg Glu Gln Gly
865                 870                 875                 880

Glu Lys Ile Ile Gln Glu Phe Leu Ser Lys Val Lys Gln Met Pro Phe
            885                 890                 895

Thr Glu Met Ser Glu Glu Asn Ile Thr Ile Lys Leu Lys Gln Leu Lys
                900                 905                 910

Ala Glu Val Ile Ala Lys Asn Asn Ser Phe Val Asn Glu Ile Ile Ser
            915                 920                 925

Arg Ile Lys Val Thr Thr
        930

<210> SEQ ID NO 17
<211> LENGTH: 4374
<212> TYPE: DNA
<213> ORGANISM: Homo sapiens

<400> SEQUENCE: 17
gggcacgagc cctgccatgt ctcgccggaa gcctgcgtcg ggcggcctcg ctgcctccag     60
ctcagcccct gcgaggcaag cggttttgag ccgattcttc cagtctacgg gaagcctgaa    120
atccacctcc tcctccacag gtgcagccga ccaggtggac cctggcgctg cagcggccgc    180
agcgccccca gcgcccgcct tcccgcccca gctgccgccg cacgtagcta cagaaattga    240
cagaagaaag aagagaccat tggaaaatga tgggcctgtt aaaaagaaag taagaaagt     300 ccaacaaaag gaaggaggaa gtgatctggg aatgtctggc aactctgagc aaagaaatg     360 tctgaggacc aggaatgttt caaagtctct ggaaaaattg aaagaattct gctgcgattc    420
tgcccttcct caaagtagag tccagacaga atctctgcag gagagatttg cagttctgcc    480
aaaatgtact gattttgatg atatcagtct tctacacgca aagaatgcag tttcttctga    540
agattcgaaa cgtcaaatta tcaaaaggga cacaacactt tttgatctca gtcagtttgg    600
atcatcaaat acaagtcatg aaaatttaca gaaaactgct tccaaatcag ctaacaaacg    660
gtccaaaagc atctatacgc cgctagaatt acaatacata gaaatgaagc agcagcacaa    720
agatgcagtt ttgtgtgtgg aatgtggata taagtataga ttctttgggg aagatgcaga    780
gattgcagcc cgagagctca atatttattg ccatttagat cacaacttta tgacagcaag    840
tatacctact cacagactgt tgttcatgt acgccgcctg gtggcaaaag gatataaggt     900
gggagttgtg aagcaaactg aaactgcagc attaaaggcc attggagaca cagaagttc     960 actcttttcc cggaaattga ctgcccttta tacaaaatct acacttattg agaagatgt    1020 gaatccccta atcaagctgg atgatgctgt aaatgttgat gagataatga ctgatacttc    1080
taccagctat cttctgtgca tctctgaaaa taaggaaat gttagggaca aaaaaaaggg    1140
caacattttt attggcattg tgggagtgca gcctgccaca ggcgaggttg tgtttgatag    1200
tttccaggac tctgcttctc gttcagagct agaaacccgg atgtcaagcc tgcagccagt    1260
agagctgctg cttccttcgg ccttgtccga gcaaacagag gcgctcatcc acagagccac    1320
atctgttagt gtgcaggatg acagaattcg agtcgaaagg atggataaca tttattttga    1380
atacagccat gctttccagg cagttacaga gtttttatgca aaagatacag ttgacatcaa    1440
aggttctcaa attatttctg gcattgttaa cttagagaag cctgtgattt gctctttggc    1500
tgccatcata aaatacctca agaattcaa cttggaaaag atgctctcca aacctgagaa    1560
ttttaaacag ctatcaagta aaatggaatt tatgacaatt aatggaacaa cattaaggaa    1620
tctggaaatc ctacagaatc agactgatat gaaaaccaaa ggaagtttgc tgtgggtttt    1680
```

```
agaccacact aaaacttcat ttgggagacg gaagttaaag aagtgggtga cccagccact    1740
ccttaaatta agggaaataa atgcccggct tgatgctgta tcggaagttc tccattcaga    1800
atctagtgtg tttggtcaga tagaaaatca tctacgtaaa ttgcccgaca tagagagggg    1860
actctgtagc atttatcaca aaaaatgttc tacccaagag ttcttcttga ttgtcaaaac    1920
tttatatcac ctaaagtcag aatttcaagc aataatacct gctgttaatt cccacattca    1980
gtcagacttg ctccggaccg ttattttaga aattcctgaa ctcctcagtc cagtggagca    2040
ttacttaaag atactcaatg aacaagctgc caaagttggg gataaaactg aattatttaa    2100
agaccttcct gacttccctt taataaaaaa gaggaaggat gaaattcaag gtgttattga    2160
cgagatccga atgcatttgc aagaaatacg aaaaatacta aaaatccttt ctgcacaata    2220
tgtgacagta tcaggacagg agtttatgat agaaataaag aactctgctg tatcttgtat    2280
accaactgat tgggtaaagg ttggaagcac aaaagctgtg agccgctttc actctccttt    2340
tattgtagaa aattacagac atctgaatca gctccgggag cagctagtcc ttgactgcag    2400
tgctgaatgg cttgattttc tagagaaatt cagtgaacat tatcactcct tgtgtaaagc    2460
agtgcatcac ctagcaactg ttgactgcat tttctccctg gccaaggtcg ctaagcaagg    2520
agattactgc agaccaactg tacaagaaga agaaaaaatt gtaataaaaa atggaaggca    2580
ccctgtgatt gatgtgttgc tgggagaaca ggatcaatat gtcccaaata atacagattt    2640
atcagaggac tcagagagag taatgataat taccggacca aacatgggtg aaagagctc     2700
ctacataaaa caagttgcat tgattaccat catggctcag attggctcct atgttcctgc    2760
agaagaagcg acaattggga ttgtggatgg catttccaca aggatgggtg ctgcagacaa    2820
tatatataaa ggacggagta catttatgga agaactgact gacacagcag aaataatcag    2880
aaaagcaaca tcacagtcct tggttatctt ggatgaacta ggaagaggga cgagcactca    2940
tgatggaatt gccattgcct atgctacact tgagtatttc atcagagatg tgaaatcctt    3000
aaccctgttt gtcacccatt atccgccagt ttgtgaacta gaaaaaaatt actcacacca    3060
ggtggggaat taccacatgg gattcttggt cagtgaggat gaaagcaaac tggatccagg    3120
cgcagcagaa caagtccctg attttgtcac cttcctttac caaataacta gaggaattgc    3180
agcaaggagt tatggattaa atgtggctaa actagcagat gttcctggag aaatttttgaa   3240
gaaagcagct cacaagtcaa aagagctgga aggattaata aatacgaaaa gaaagagact    3300
caagtatttt gcaaagttat ggacgatgca taatgcacaa gacctgcaga gtggacaga    3360
ggagttcaac atgaagaaa cacagacttc tcttcttcat taaaatgaag actacatttg    3420
tgaacaaaaa atggagaatt aaaaatacca actgtacaaa ataactctcc agtaacagcc    3480
tatctttgtg tgacatgtga gcataaaatt atgaccatgg tatattccta ttggaaacag    3540
agaggttttt ctgaagacag tcttttcaa gtttctgtct tcctaacttt tctacgtata     3600
aacactcttg aatagacttc cactttgtaa ttagaaaatt ttatgacag taagtccagt     3660
aaagccttaa gtggcagaat ataattccca agcttttgga gggtgatata aaaatttact    3720
tgatatttt atttgtttca gttcagataa ttggcaactg ggtgaatctg caggaatct      3780
atccattgaa ctaaaataat tttattatgc aaccagttta tccaccaaga acataagaat    3840
tttttataag tagaaagaat tggccaggca tgtggctca tgcctgtaat cccagcactt    3900
tgggaggcca aggtaggcag atcacctgag gtcaggagtt caagaccagc ctggccaaca    3960
tggcaaaacc ccatctttac taaaaatata aagtacatct ctactaaaaa tacgaaaaaa    4020
ttagctgggc atggtggcgc acacctgtag tcccagctac tccggaggct gaggcaggag    4080
```

-continued

```
aatctcttga acctgggagg cggaggttgc aatgagccga gatcacgtca ctgcactcca    4140
gcttgggcaa cagagcaaga ctccatctca aaaagaaaa aagaaagaa atagaattat      4200 caagctttta aaaactagag cacagaagga ataaggtcat gaaatttaaa aggttaaata    4260
ttgtcatagg attaagcagt ttaaagattg ttggatgaaa ttatttgtca ttcattcaag    4320
taataaatat ttaatgaata cttgctataa aaaaaaaaaa aaaaaaaaaa aaaa          4374
```

<210> SEQ ID NO 18
<211> LENGTH: 1128
<212> TYPE: PRT
<213> ORGANISM: Homo sapiens

<400> SEQUENCE: 18

```
Met Ser Arg Arg Lys Pro Ala Ser Gly Gly Leu Ala Ala Ser Ser Ser
1               5                   10                  15

Ala Pro Ala Arg Gln Ala Val Leu Ser Arg Phe Phe Gln Ser Thr Gly
            20                  25                  30

Ser Leu Lys Ser Thr Ser Ser Thr Gly Ala Ala Asp Gln Val Asp
        35                  40                  45

Pro Gly Ala Ala Ala Ala Ala Pro Pro Ala Pro Ala Phe Pro Pro
    50                  55                  60

Gln Leu Pro Pro His Val Ala Thr Glu Ile Asp Arg Arg Lys Lys Arg
65                  70                  75                  80

Pro Leu Glu Asn Asp Gly Pro Val Lys Lys Val Lys Lys Val Gln
                85                  90                  95

Gln Lys Glu Gly Gly Ser Asp Leu Gly Met Ser Gly Asn Ser Glu Pro
            100                 105                 110

Lys Lys Cys Leu Arg Thr Arg Asn Val Ser Lys Ser Leu Glu Lys Leu
        115                 120                 125

Lys Glu Phe Cys Cys Asp Ser Ala Leu Pro Gln Ser Arg Val Gln Thr
    130                 135                 140

Glu Ser Leu Gln Glu Arg Phe Ala Val Leu Pro Lys Cys Thr Asp Phe
145                 150                 155                 160

Asp Asp Ile Ser Leu Leu His Ala Lys Asn Ala Val Ser Ser Glu Asp
                165                 170                 175

Ser Lys Arg Gln Ile Asn Gln Lys Asp Thr Thr Leu Phe Asp Leu Ser
            180                 185                 190

Gln Phe Gly Ser Ser Asn Thr Ser His Glu Asn Leu Gln Lys Thr Ala
        195                 200                 205

Ser Lys Ser Ala Asn Lys Arg Ser Lys Ser Ile Tyr Thr Pro Leu Glu
    210                 215                 220

Leu Gln Tyr Ile Glu Met Lys Gln Gln His Lys Asp Ala Val Leu Cys
225                 230                 235                 240

Val Glu Cys Gly Tyr Lys Tyr Arg Phe Phe Gly Glu Asp Ala Glu Ile
                245                 250                 255

Ala Ala Arg Glu Leu Asn Ile Tyr Cys His Leu Asp His Asn Phe Met
            260                 265                 270

Thr Ala Ser Ile Pro Thr His Arg Leu Phe Val His Val Arg Arg Leu
        275                 280                 285

Val Ala Lys Gly Tyr Lys Val Gly Val Val Lys Gln Thr Glu Thr Ala
    290                 295                 300

Ala Leu Lys Ala Ile Gly Asp Asn Arg Ser Ser Leu Phe Ser Arg Lys
305                 310                 315                 320
```

```
Leu Thr Ala Leu Tyr Thr Lys Ser Thr Leu Ile Gly Glu Asp Val Asn
                325                 330                 335

Pro Leu Ile Lys Leu Asp Asp Ala Val Asn Val Asp Glu Ile Met Thr
                340                 345                 350

Asp Thr Ser Thr Ser Tyr Leu Leu Cys Ile Ser Glu Asn Lys Glu Asn
                355                 360                 365

Val Arg Asp Lys Lys Lys Gly Asn Ile Phe Ile Gly Ile Val Gly Val
            370                 375                 380

Gln Pro Ala Thr Gly Glu Val Val Phe Asp Ser Phe Gln Asp Ser Ala
385                 390                 395                 400

Ser Arg Ser Glu Leu Glu Thr Arg Met Ser Ser Leu Gln Pro Val Glu
                405                 410                 415

Leu Leu Leu Pro Ser Ala Leu Ser Glu Gln Thr Glu Ala Leu Ile His
                420                 425                 430

Arg Ala Thr Ser Val Ser Val Gln Asp Asp Arg Ile Arg Val Glu Arg
            435                 440                 445

Met Asp Asn Ile Tyr Phe Glu Tyr Ser His Ala Phe Gln Ala Val Thr
        450                 455                 460

Glu Phe Tyr Ala Lys Asp Thr Val Asp Ile Lys Gly Ser Gln Ile Ile
465                 470                 475                 480

Ser Gly Ile Val Asn Leu Glu Lys Pro Val Ile Cys Ser Leu Ala Ala
                485                 490                 495

Ile Ile Lys Tyr Leu Lys Glu Phe Asn Leu Glu Lys Met Leu Ser Lys
                500                 505                 510

Pro Glu Asn Phe Lys Gln Leu Ser Ser Lys Met Glu Phe Met Thr Ile
            515                 520                 525

Asn Gly Thr Thr Leu Arg Asn Leu Glu Ile Leu Gln Asn Gln Thr Asp
        530                 535                 540

Met Lys Thr Lys Gly Ser Leu Leu Trp Val Leu Asp His Thr Lys Thr
545                 550                 555                 560

Ser Phe Gly Arg Arg Lys Leu Lys Lys Trp Val Thr Gln Pro Leu Leu
                565                 570                 575

Lys Leu Arg Glu Ile Asn Ala Arg Leu Asp Ala Val Ser Glu Val Leu
            580                 585                 590

His Ser Glu Ser Ser Val Phe Gly Gln Ile Glu Asn His Leu Arg Lys
        595                 600                 605

Leu Pro Asp Ile Glu Arg Gly Leu Cys Ser Ile Tyr His Lys Lys Cys
        610                 615                 620

Ser Thr Gln Glu Phe Phe Leu Ile Val Lys Thr Leu Tyr His Leu Lys
625                 630                 635                 640

Ser Glu Phe Gln Ala Ile Ile Pro Ala Val Asn Ser His Ile Gln Ser
                645                 650                 655

Asp Leu Leu Arg Thr Val Ile Leu Glu Ile Pro Glu Leu Leu Ser Pro
            660                 665                 670

Val Glu His Tyr Leu Lys Ile Leu Asn Glu Gln Ala Ala Lys Val Gly
        675                 680                 685

Asp Lys Thr Glu Leu Phe Lys Asp Leu Ser Asp Phe Pro Leu Ile Lys
        690                 695                 700

Lys Arg Lys Asp Glu Ile Gln Gly Val Ile Asp Glu Ile Arg Met His
705                 710                 715                 720

Leu Gln Glu Ile Arg Lys Ile Leu Lys Asn Pro Ser Ala Gln Tyr Val
                725                 730                 735

Thr Val Ser Gly Gln Glu Phe Met Ile Glu Ile Lys Asn Ser Ala Val
```

```
                    740                 745                 750
Ser Cys Ile Pro Thr Asp Trp Val Lys Val Gly Ser Thr Lys Ala Val
            755                 760                 765
Ser Arg Phe His Ser Pro Phe Ile Val Glu Asn Tyr Arg His Leu Asn
        770                 775                 780
Gln Leu Arg Glu Gln Leu Val Leu Asp Cys Ser Ala Glu Trp Leu Asp
785                 790                 795                 800
Phe Leu Glu Lys Phe Ser Glu His Tyr His Ser Leu Cys Lys Ala Val
                805                 810                 815
His His Leu Ala Thr Val Asp Cys Ile Phe Ser Leu Ala Lys Val Ala
            820                 825                 830
Lys Gln Gly Asp Tyr Cys Arg Pro Thr Val Gln Glu Glu Arg Lys Ile
        835                 840                 845
Val Ile Lys Asn Gly Arg His Pro Val Ile Asp Val Leu Leu Gly Glu
850                 855                 860
Gln Asp Gln Tyr Val Pro Asn Asn Thr Asp Leu Ser Glu Asp Ser Glu
865                 870                 875                 880
Arg Val Met Ile Ile Thr Gly Pro Asn Met Gly Gly Lys Ser Ser Tyr
                885                 890                 895
Ile Lys Gln Val Ala Leu Ile Thr Ile Met Ala Gln Ile Gly Ser Tyr
            900                 905                 910
Val Pro Ala Glu Glu Ala Thr Ile Gly Ile Val Asp Gly Ile Phe Thr
        915                 920                 925
Arg Met Gly Ala Ala Asp Asn Ile Tyr Lys Gly Arg Ser Thr Phe Met
930                 935                 940
Glu Glu Leu Thr Asp Thr Ala Glu Ile Ile Arg Lys Ala Thr Ser Gln
945                 950                 955                 960
Ser Leu Val Ile Leu Asp Glu Leu Gly Arg Gly Thr Ser Thr His Asp
                965                 970                 975
Gly Ile Ala Ile Ala Tyr Ala Thr Leu Glu Tyr Phe Ile Arg Asp Val
            980                 985                 990
Lys Ser Leu Thr Leu Phe Val Thr His Tyr Pro Pro Val Cys Glu Leu
        995                 1000                1005
Glu Lys Asn Tyr Ser His Gln Val Gly Asn Tyr His Met Gly Phe
        1010                1015                1020
Leu Val Ser Glu Asp Glu Ser Lys Leu Asp Pro Gly Ala Ala Glu
        1025                1030                1035
Gln Val Pro Asp Phe Val Thr Phe Leu Tyr Gln Ile Thr Arg Gly
        1040                1045                1050
Ile Ala Ala Arg Ser Tyr Gly Leu Asn Val Ala Lys Leu Ala Asp
        1055                1060                1065
Val Pro Gly Glu Ile Leu Lys Lys Ala Ala His Lys Ser Lys Glu
        1070                1075                1080
Leu Glu Gly Leu Ile Asn Thr Lys Arg Lys Arg Leu Lys Tyr Phe
        1085                1090                1095
Ala Lys Leu Trp Thr Met His Asn Ala Gln Asp Leu Gln Lys Trp
        1100                1105                1110
Thr Glu Glu Phe Asn Met Glu Glu Thr Gln Thr Ser Leu Leu His
        1115                1120                1125

<210> SEQ ID NO 19
<211> LENGTH: 3095
<212> TYPE: DNA
<213> ORGANISM: Homo sapiens
```

<400> SEQUENCE: 19

```
cagaaacctc atacttctcg ggtcagggaa ggtttgggag gatgctgagg cctgagatct      60
catcaacctc gccttctgcc ccggcggttt cccccgtcgt cggagaaacc cgctcacctc     120
agggtccccg ctacaatttc ggactccagg agactccaca gagccgccct tcggtccagg     180
tggtctctgc atccacctgt cctggcacgt caggagctgc gggcgaccgg agcagcagca     240
gcagcagcct tccctgcccc gcgccaaact cccggccagc tcaaggttca tactttggaa     300
acaaaagagc ttatgcagaa aacacagttg catcaaattt tacttttggt gcaagctcat     360
cttctgcacg agatactaat tatcctcaaa cacttaaaac tccattgtct actggaaatc     420
ctcagagatc aggttataag agctggacac cacaagtggg atattcagct tcatcctcat     480
ctgcgatttc tgcacactcc ccatcagtta ttgtagctgt tgtagaaggg agaggacttg     540
ccagaggtga ataggaatg caagtattg atttaaaaaa ccccaaatt atactatccc       600
agtttgcaga caacacaaca tatgcaaagg tgatcactaa acttaaaatt ttatcacctt     660
tggaaataat aatgtcaaat actgcttgtg ctgtggggaa ttccaccaag ttgttcactc     720
tgatcacaga aaatttcaag aatgttaatt tcactactat ccaaaggaaa tacttcaatg     780
aaacaaaagg attagagtac attgaacagt tatgcatagc agaattcagc actgtcctaa     840
tggaggttca gtccaagtat tactgccttg cagctgttgc agctttgtta aaatatgttg     900
aatttattca aaattcagtt tatgcaccaa atcactgaa gatttgtttc cagggtagtg     960
aacagacagc catgatagat tcatcatcag cccaaaacct tgaattgtta attaataatc    1020
aagactatag gaataatcac actctctttg gtgttctaaa ttatactaag actcctggag    1080
ggagtagacg acttcgttct aatatattag agcctctagt tgatattgaa accattaaca    1140
tgcgcttaga ttgtgttcaa gaactacttc aagatgagga actattttt ggacttcaat    1200
cagttatatc aagatttctt gatacagagc agcttctttc tgttttagtc caaattccag    1260
agcaagacac ggtcaatgct gctgaatcaa agataacaaa tttaatatac ttaaaacata    1320
ccttggaact tgtggatcct ttaaagattg ctatgaagaa ctgtaacaca cctttattaa    1380
gagcttacta tggttccttg aagacaaga ggtttggaat catacttgaa aagattaaaa    1440
cagtaattaa tgatgatgca agatacatga aaggatgcct aaacatgagg actcagaagt    1500
gctatgcagt gaggtctaac ataaatgaat tcttgacat agcaagaaga acatacacag    1560
agattgtaga tgacatagca ggaatgtat cacaacttgg agaaaaatat agtctacctt    1620
taaggacaag tcttagctct gttcgaggat ttttcatcca gatgactaca gattgtatag    1680
ccctacctag tgatcaactt ccttcagaat ttattaagat ttctaaagtg aaaaattctt    1740
acagctttac atcagcagat ttaattaaaa tgaatgaaag atgccaagaa tctttgagag    1800
aaatctatca catgacttat atgatagtgt gcaaactgct tagtgagatt tatgaacata    1860
ttcattgctt atataaacta tctgacactg tgtcaatgct ggatatgcta ctgtcatttg    1920
ctcatgcctg cactctttct gactatgttc gaccagaatt tactgatact ttagcaatca    1980
aacagggatg gcatcctatt cttgaaaaaa tatctgcgga aaaacctatt gccaacaata    2040
cctatgttac agaagggagt aattttttga tcataactgg accaaacatg agtggaaaat    2100
ccacatattt aaaacagatt gctctttgtc agattatggc ccagattgga tcatatgttc    2160
cagcagaata ttcttccttt agaattgcta acagattttt acaagaatt agtactgatg    2220
atgatatcga aacaaattca tcaacatttta tgaaagaaat gaaagagata gcatatattc    2280
```

```
tacataatgc taatgacaaa tcgctcatat taattgatga acttggcaga ggtactaata   2340
cggaagaagg tattggcatt tgttatgctg tttgtgaata tctactgagc ttaaaggcat   2400
ttacactgtt tgctacacat ttcctggaac tatgccatat tgatgccctg tatcctaatg   2460
tagaaaacat gcattttgaa gttcaacatg taaagaatac ctcaagaaat aaagaagcaa   2520
ttttgtatac ctacaaactt tctaaggcac tcacagaaga gaaaaattat ggattaaaag   2580
ctgcagaggt gtcatcactt ccaccatcaa ttgtcttgga tgccaaggaa atcacaactc   2640
aaattacgag acaaattttg caaaaccaaa ggagtacccc tgagatggaa agacagagag   2700
ctgtgtacca tctagccact aggcttgttc aaactgctcg aaactctcaa ttggatccag   2760
acagtttacg aatatattta agtaacctca agaagaagta caagaagat tttcccagga    2820 ccgaacaagt tccagaaaag actgaagaat aatcacaatt ctaatgtaat aatatatctt   2880
aattcaagga acctagaatt tattttctc cttagagata aggaaaataa catttgccaa    2940
atttcatatt ttaattgaaa attacattat attaacatca caattgtcat ctatatattc   3000
tatatgaaaa atatttatta taacttaaca aatgagaact acttaaagga atggttttta   3060
tgttaggaga aaatacaata caccacaaaa aaaaa                              3095
```

<210> SEQ ID NO 20
<211> LENGTH: 936
<212> TYPE: PRT
<213> ORGANISM: Homo sapiens

<400> SEQUENCE: 20

```
Met Leu Arg Pro Glu Ile Ser Ser Thr Ser Pro Ser Ala Pro Ala Val
1               5                   10                  15

Ser Pro Val Val Gly Glu Thr Arg Ser Pro Gln Gly Pro Arg Tyr Asn
            20                  25                  30

Phe Gly Leu Gln Glu Thr Pro Gln Ser Arg Pro Ser Val Gln Val Val
        35                  40                  45

Ser Ala Ser Thr Cys Pro Gly Thr Ser Gly Ala Ala Gly Asp Arg Ser
    50                  55                  60

Ser Ser Ser Ser Ser Leu Pro Cys Pro Ala Pro Asn Ser Arg Pro Ala
65                  70                  75                  80

Gln Gly Ser Tyr Phe Gly Asn Lys Arg Ala Tyr Ala Glu Asn Thr Val
                85                  90                  95

Ala Ser Asn Phe Thr Phe Gly Ala Ser Ser Ser Ala Arg Asp Thr
            100                 105                 110

Asn Tyr Pro Gln Thr Leu Lys Thr Pro Leu Ser Thr Gly Asn Pro Gln
        115                 120                 125

Arg Ser Gly Tyr Lys Ser Trp Thr Pro Gln Val Gly Tyr Ser Ala Ser
    130                 135                 140

Ser Ser Ser Ala Ile Ser Ala His Ser Pro Ser Val Ile Val Ala Val
145                 150                 155                 160

Val Glu Gly Arg Gly Leu Ala Arg Gly Glu Ile Gly Met Ala Ser Ile
                165                 170                 175

Asp Leu Lys Asn Pro Gln Ile Ile Leu Ser Gln Phe Ala Asp Asn Thr
            180                 185                 190

Thr Tyr Ala Lys Val Ile Thr Lys Leu Lys Ile Leu Ser Pro Leu Glu
        195                 200                 205

Ile Ile Met Ser Asn Thr Ala Cys Ala Val Gly Asn Ser Thr Lys Leu
    210                 215                 220

Phe Thr Leu Ile Thr Glu Asn Phe Lys Asn Val Asn Phe Thr Thr Ile
```

```
            225                 230                 235                 240
Gln Arg Lys Tyr Phe Asn Glu Thr Lys Gly Leu Glu Tyr Ile Glu Gln
                245                 250                 255
Leu Cys Ile Ala Glu Phe Ser Thr Val Leu Met Glu Val Gln Ser Lys
            260                 265                 270
Tyr Tyr Cys Leu Ala Ala Val Ala Ala Leu Leu Lys Tyr Val Glu Phe
        275                 280                 285
Ile Gln Asn Ser Val Tyr Ala Pro Lys Ser Leu Lys Ile Cys Phe Gln
    290                 295                 300
Gly Ser Glu Gln Thr Ala Met Ile Asp Ser Ser Ala Gln Asn Leu
305                 310                 315                 320
Glu Leu Leu Ile Asn Asn Gln Asp Tyr Arg Asn Asn His Thr Leu Phe
                325                 330                 335
Gly Val Leu Asn Tyr Thr Lys Thr Pro Gly Gly Ser Arg Arg Leu Arg
            340                 345                 350
Ser Asn Ile Leu Glu Pro Leu Val Asp Ile Glu Thr Ile Asn Met Arg
        355                 360                 365
Leu Asp Cys Val Gln Glu Leu Leu Gln Asp Glu Glu Leu Phe Phe Gly
    370                 375                 380
Leu Gln Ser Val Ile Ser Arg Phe Leu Asp Thr Glu Gln Leu Leu Ser
385                 390                 395                 400
Val Leu Val Gln Ile Pro Glu Gln Asp Thr Val Asn Ala Ala Glu Ser
                405                 410                 415
Lys Ile Thr Asn Leu Ile Tyr Leu Lys His Thr Leu Glu Leu Val Asp
            420                 425                 430
Pro Leu Lys Ile Ala Met Lys Asn Cys Asn Thr Pro Leu Leu Arg Ala
        435                 440                 445
Tyr Tyr Gly Ser Leu Glu Asp Lys Arg Phe Gly Ile Ile Leu Glu Lys
    450                 455                 460
Ile Lys Thr Val Ile Asn Asp Asp Ala Arg Tyr Met Lys Gly Cys Leu
465                 470                 475                 480
Asn Met Arg Thr Gln Lys Cys Tyr Ala Val Arg Ser Asn Ile Asn Glu
                485                 490                 495
Phe Leu Asp Ile Ala Arg Arg Thr Tyr Thr Glu Ile Val Asp Asp Ile
            500                 505                 510
Ala Gly Met Ile Ser Gln Leu Gly Glu Lys Tyr Ser Leu Pro Leu Arg
        515                 520                 525
Thr Ser Leu Ser Ser Val Arg Gly Phe Phe Ile Gln Met Thr Thr Asp
    530                 535                 540
Cys Ile Ala Leu Pro Ser Asp Gln Leu Pro Ser Glu Phe Ile Lys Ile
545                 550                 555                 560
Ser Lys Val Lys Asn Ser Tyr Ser Phe Thr Ser Ala Asp Leu Ile Lys
                565                 570                 575
Met Asn Glu Arg Cys Gln Glu Ser Leu Arg Glu Ile Tyr His Met Thr
            580                 585                 590
Tyr Met Ile Val Cys Lys Leu Leu Ser Glu Ile Tyr Glu His Ile His
        595                 600                 605
Cys Leu Tyr Lys Leu Ser Asp Thr Val Ser Met Leu Asp Met Leu Leu
    610                 615                 620
Ser Phe Ala His Ala Cys Thr Leu Ser Asp Tyr Val Arg Pro Glu Phe
625                 630                 635                 640
Thr Asp Thr Leu Ala Ile Lys Gln Gly Trp His Pro Ile Leu Glu Lys
                645                 650                 655
```

```
Ile Ser Ala Glu Lys Pro Ile Ala Asn Asn Thr Tyr Val Thr Glu Gly
        660                 665                 670

Ser Asn Phe Leu Ile Ile Thr Gly Pro Asn Met Ser Gly Lys Ser Thr
        675                 680                 685

Tyr Leu Lys Gln Ile Ala Leu Cys Gln Ile Met Ala Gln Ile Gly Ser
        690                 695                 700

Tyr Val Pro Ala Glu Tyr Ser Ser Phe Arg Ile Ala Lys Gln Ile Phe
705                 710                 715                 720

Thr Arg Ile Ser Thr Asp Asp Ile Glu Thr Asn Ser Ser Thr Phe
            725                 730                 735

Met Lys Glu Met Lys Glu Ile Ala Tyr Ile Leu His Asn Ala Asn Asp
        740                 745                 750

Lys Ser Leu Ile Leu Ile Asp Glu Leu Gly Arg Gly Thr Asn Thr Glu
        755                 760                 765

Glu Gly Ile Gly Ile Cys Tyr Ala Val Cys Glu Tyr Leu Leu Ser Leu
        770                 775                 780

Lys Ala Phe Thr Leu Phe Ala Thr His Phe Leu Glu Leu Cys His Ile
785                 790                 795                 800

Asp Ala Leu Tyr Pro Asn Val Glu Asn Met His Phe Glu Val Gln His
                805                 810                 815

Val Lys Asn Thr Ser Arg Asn Lys Glu Ala Ile Leu Tyr Thr Tyr Lys
        820                 825                 830

Leu Ser Lys Gly Leu Thr Glu Glu Lys Asn Tyr Gly Leu Lys Ala Ala
        835                 840                 845

Glu Val Ser Ser Leu Pro Pro Ser Ile Val Leu Asp Ala Lys Glu Ile
850                 855                 860

Thr Thr Gln Ile Thr Arg Gln Ile Leu Gln Asn Gln Arg Ser Thr Pro
865                 870                 875                 880

Glu Met Glu Arg Gln Arg Ala Val Tyr His Leu Ala Thr Arg Leu Val
                885                 890                 895

Gln Thr Ala Arg Asn Ser Gln Leu Asp Pro Asp Ser Leu Arg Ile Tyr
        900                 905                 910

Leu Ser Asn Leu Lys Lys Lys Tyr Lys Glu Asp Phe Pro Arg Thr Glu
        915                 920                 925

Gln Val Pro Glu Lys Thr Glu Glu
        930                 935

<210> SEQ ID NO 21
<211> LENGTH: 2726
<212> TYPE: DNA
<213> ORGANISM: Homo sapiens

<400> SEQUENCE: 21
gcggtcggtc agcggggcgt tctcccacct gtagcgactc agagcctcca agctcatggc      60
ctccttagga gcgaacccaa ggaggacacc gcagggaccg agacctgggg cggcctcctc     120
cggcttcccc agcccggccc cagtgccggg ccccagggag gccgaggagg aggaagtcga     180
ggaggaggag gagctggccg agatccatct gtgtgtgctg tggaattcag gatacttggg     240
cattgcctac tatgatacta gtgactccac tatccacttc atgccagatg ccccagacca     300
cgagagcctc aagcttctcc agagagttct ggatgagatc aatccccagt ctgttgttac     360
gagtgccaaa caggatgaga atatgactcg atttctggga aagcttgcct cccaggagca     420
cagagagcct aaaagacctg aaatcatatt tttgccaagt gtggattttg gtctggagat     480
```

```
aagcaaacaa cgcctccttt ctggaaacta ctccttcatc ccagacgcca tgactgccac    540
tgagaaaatc ctcttcctct cttccattat tcccttttgac tgcctcctca cagttcgagc    600
acttggaggg ctgctgaagt tcctgggtcg aagaagaatc ggggttgaac tggaagacta    660
taatgtcagc gtccccatcc tgggctttaa gaaatttatg ttgactcatc tggtgaacat    720
agatcaagac acttacagtg ttctacagat ttttaagagt gagtctcacc cctcagtgta    780
caaagtggcc agtggactga aggaggggct cagcctcttt ggaatcctca acagatgcca    840
ctgtaagtgg ggagagaagc tgctcaggct atggttcaca cgtccgactc atgacctggg    900
ggagctcagt tctcgtctgg acgtcattca gttttttctg ctgccccaga atctggacat    960
ggctcagatg ctgcatcggc tcctgggtca catcaagaac gtgcctctga ttctgaaacg   1020
catgaagttg tcccacacca aggtcagcga ctggcaggtt ctctacaaga ctgtgtacag   1080
tgccctgggc tgagggatg cctgccgctc cctgccgcag tccatccagc tctttcggga   1140
cattgcccaa gagttctctg atgacctgca ccatatcgcc agcctcattg ggaaagtagt   1200
ggactttgag ggcagccttg ctgaaaatcg cttcacagtc ctccccaaca tagatcctga   1260
aattgatgag aaaaagcgaa gactgatggg acttcccagt ttccttactg aggttgcccg   1320
caaggagctg gagaatctgg actcccgtat tccttcatgc agtgtcatct acatccctct   1380
gattggcttc cttctttcta ttccccgcct gccttccatg gtagaggcca gtgactttga   1440
gattaatgga ctggacttca tgtttctctc agaggagaag ctgcactatc gtagtgcccg   1500
aaccaaggag ctggatgcat tgctggggga cctgcactgc gagatccggg accaggagac   1560
gctgctgatg taccagctac agtgccaggt gctggcacga gcagctgtct taacccgagt   1620
attggacctt gcctcccgcc tggacgtcct gctggctctt gccagtgctg cccgggacta   1680
tggctactca aggccgcgtt actccccaca agtccttggg gtacgaatcc agaatggcag   1740
acatcctctg atggaactct gtgcccgaac ctttgtgccc aactccacag aatgtggtgg   1800
ggacaaaggg agggtcaaag tcatcactgg acccaactca tcaggaagga gcatatacct   1860
caaacaggta ggcttgatca cattcatggc cctggtaggc agctttgtgc cagcagagga   1920
ggccgaaatt ggggcagtag acgccatctt cacacgaatt catagctgcg aatccatctc   1980
ccttggcctc tccaccttca tgatcgacct caaccagcag gtggcgaaag cagtgaacaa   2040
tgccactgca cagtcgctgg tccttattga tgaatttgga aagggaacca acacggtgga   2100
tgggctcgcg cttctggccg ctgtgctccg acactggctg gcacgtggac ccacatgccc   2160
ccacatcttt gtgccaccaa acttttctgag ccttgttcag ctacaactgc tgccacaagg   2220
gcccctggtg cagtatttga ccatggagac ctgtgaggat ggcaacgatc ttgtcttctt   2280
ctatcaggtt tgcgaaggtg ttgcgaaggc cagccatgcc tcccacacag ctgcccaggc   2340
tgggcttcct gacaagcttg tggctcgtgg caaggaggtc tcagacttga tccgcagtgg   2400
aaaacccatc aagcctgtca aggatttgct aaagaagaac caaatggaaa attgccagac   2460
attagtggat aagtttatga aactggattt ggaagatcct aacctggact tgaacgtttt   2520
catgagccag gaagtgctgc ctgctgccac cagcatcctc tgagagtcct tccagtgtcc   2580
tccccagcct cctgagactc cggtgggctg ccatgccctc tttgtttcct tatctccctc   2640
agacgcagag tttttagttt ctctagaaat tttgtttcat attaggaata aagtttattt   2700
tgaagaaaaa aaaaaaaaaa aaaaaa                                         2726

<210> SEQ ID NO 22
<211> LENGTH: 835
```

```
<212> TYPE: PRT
<213> ORGANISM: Homo sapiens

<400> SEQUENCE: 22

Met Ala Ser Leu Gly Ala Asn Pro Arg Arg Thr Pro Gln Gly Pro Arg
1               5                   10                  15

Pro Gly Ala Ala Ser Ser Gly Phe Pro Ser Pro Ala Pro Val Pro Gly
            20                  25                  30

Pro Arg Glu Ala Glu Glu Glu Val Glu Glu Glu Glu Glu Leu Ala
        35                  40                  45

Glu Ile His Leu Cys Val Leu Trp Asn Ser Gly Tyr Leu Gly Ile Ala
50                  55                  60

Tyr Tyr Asp Thr Ser Asp Ser Thr Ile His Phe Met Pro Asp Ala Pro
65                  70                  75                  80

Asp His Glu Ser Leu Lys Leu Leu Gln Arg Val Leu Asp Glu Ile Asn
                85                  90                  95

Pro Gln Ser Val Val Thr Ser Ala Lys Gln Asp Glu Asn Met Thr Arg
            100                 105                 110

Phe Leu Gly Lys Leu Ala Ser Gln Glu His Arg Glu Pro Lys Arg Pro
            115                 120                 125

Glu Ile Ile Phe Leu Pro Ser Val Asp Phe Gly Leu Glu Ile Ser Lys
130                 135                 140

Gln Arg Leu Leu Ser Gly Asn Tyr Ser Phe Ile Pro Asp Ala Met Thr
145                 150                 155                 160

Ala Thr Glu Lys Ile Leu Phe Leu Ser Ser Ile Ile Pro Phe Asp Cys
                165                 170                 175

Leu Leu Thr Val Arg Ala Leu Gly Gly Leu Leu Lys Phe Leu Gly Arg
            180                 185                 190

Arg Arg Ile Gly Val Glu Leu Glu Asp Tyr Asn Val Ser Val Pro Ile
            195                 200                 205

Leu Gly Phe Lys Lys Phe Met Leu Thr His Leu Val Asn Ile Asp Gln
210                 215                 220

Asp Thr Tyr Ser Val Leu Gln Ile Phe Lys Ser Glu Ser His Pro Ser
225                 230                 235                 240

Val Tyr Lys Val Ala Ser Gly Leu Lys Glu Gly Leu Ser Leu Phe Gly
                245                 250                 255

Ile Leu Asn Arg Cys His Cys Lys Trp Gly Glu Lys Leu Leu Arg Leu
            260                 265                 270

Trp Phe Thr Arg Pro Thr His Asp Leu Gly Glu Leu Ser Ser Arg Leu
            275                 280                 285

Asp Val Ile Gln Phe Phe Leu Leu Pro Gln Asn Leu Asp Met Ala Gln
            290                 295                 300

Met Leu His Arg Leu Leu Gly His Ile Lys Asn Val Pro Leu Ile Leu
305                 310                 315                 320

Lys Arg Met Lys Leu Ser His Thr Lys Val Ser Asp Trp Gln Val Leu
                325                 330                 335

Tyr Lys Thr Val Tyr Ser Ala Leu Gly Leu Arg Asp Ala Cys Arg Ser
            340                 345                 350

Leu Pro Gln Ser Ile Gln Leu Phe Arg Asp Ile Ala Gln Glu Phe Ser
            355                 360                 365

Asp Asp Leu His His Ile Ala Ser Leu Ile Gly Lys Val Val Asp Phe
370                 375                 380

Glu Gly Ser Leu Ala Glu Asn Arg Phe Thr Val Leu Pro Asn Ile Asp
385                 390                 395                 400
```

-continued

```
Pro Glu Ile Asp Glu Lys Lys Arg Arg Leu Met Gly Leu Pro Ser Phe
            405                 410                 415
Leu Thr Glu Val Ala Arg Lys Glu Leu Glu Asn Leu Asp Ser Arg Ile
            420                 425                 430
Pro Ser Cys Ser Val Ile Tyr Ile Pro Leu Ile Gly Phe Leu Leu Ser
            435                 440                 445
Ile Pro Arg Leu Pro Ser Met Val Glu Ala Ser Asp Phe Glu Ile Asn
450                 455                 460
Gly Leu Asp Phe Met Phe Leu Ser Glu Lys Leu His Tyr Arg Ser
465                 470                 475                 480
Ala Arg Thr Lys Glu Leu Asp Ala Leu Leu Gly Asp Leu His Cys Glu
            485                 490                 495
Ile Arg Asp Gln Glu Thr Leu Leu Met Tyr Gln Leu Gln Cys Gln Val
            500                 505                 510
Leu Ala Arg Ala Ala Val Leu Thr Arg Val Leu Asp Leu Ala Ser Arg
            515                 520                 525
Leu Asp Val Leu Leu Ala Leu Ala Ser Ala Ala Arg Asp Tyr Gly Tyr
530                 535                 540
Ser Arg Pro Arg Tyr Ser Pro Gln Val Leu Gly Val Arg Ile Gln Asn
545                 550                 555                 560
Gly Arg His Pro Leu Met Glu Leu Cys Ala Arg Thr Phe Val Pro Asn
            565                 570                 575
Ser Thr Glu Cys Gly Asp Lys Gly Arg Val Lys Val Ile Thr Gly
            580                 585                 590
Pro Asn Ser Ser Gly Lys Ser Ile Tyr Leu Lys Gln Val Gly Leu Ile
            595                 600                 605
Thr Phe Met Ala Leu Val Gly Ser Phe Val Pro Ala Glu Glu Ala Glu
            610                 615                 620
Ile Gly Ala Val Asp Ala Ile Phe Thr Arg Ile His Ser Cys Glu Ser
625                 630                 635                 640
Ile Ser Leu Gly Leu Ser Thr Phe Met Ile Asp Leu Asn Gln Gln Val
            645                 650                 655
Ala Lys Ala Val Asn Asn Ala Thr Ala Gln Ser Leu Val Leu Ile Asp
            660                 665                 670
Glu Phe Gly Lys Gly Thr Asn Thr Val Asp Gly Leu Ala Leu Leu Ala
            675                 680                 685
Ala Val Leu Arg His Trp Leu Ala Arg Gly Pro Thr Cys Pro His Ile
            690                 695                 700
Phe Val Ala Thr Asn Phe Leu Ser Leu Val Gln Leu Gln Leu Leu Pro
705                 710                 715                 720
Gln Gly Pro Leu Val Gln Tyr Leu Thr Met Glu Thr Cys Glu Asp Gly
            725                 730                 735
Asn Asp Leu Val Phe Phe Tyr Gln Val Cys Glu Gly Val Ala Lys Ala
            740                 745                 750
Ser His Ala Ser His Thr Ala Ala Gln Ala Gly Leu Pro Asp Lys Leu
            755                 760                 765
Val Ala Arg Gly Lys Glu Val Ser Asp Leu Ile Arg Ser Gly Lys Pro
            770                 775                 780
Ile Lys Pro Val Lys Asp Leu Leu Lys Asn Gln Met Glu Asn Cys
785                 790                 795                 800
Gln Thr Leu Val Asp Lys Phe Met Lys Leu Asp Leu Glu Asp Pro Asn
            805                 810                 815
```

Leu Asp Leu Asn Val Phe Met Ser Gln Glu Val Leu Pro Ala Ala Thr
            820                 825                 830
Ser Ile Leu
        835

<210> SEQ ID NO 23
<211> LENGTH: 4264
<212> TYPE: DNA
<213> ORGANISM: Homo sapiens

<400> SEQUENCE: 23

| | | | | |
|---|---|---|---|---|
| atttcccgcc | agcaggagcc | gcgcggtaga | tgcggtgctt | ttaggagctc cgtccgacag | 60 |
| aacggttggg | ccttgccggc | tgtcggtatg | tcgcgacaga | gcaccctgta cagcttcttc | 120 |
| cccaagtctc | cggcgctgag | tgatgccaac | aaggcctcgg | ccagggcctc acgcgaaggc | 180 |
| ggccgtgccg | ccgctgcccc | cggggcctct | ccttccccag | gcgggatgc ggcctggagc | 240 |
| gaggctgggc | ctgggcccag | gcccttggcg | cgatccgcgt | caccgcccaa ggcgaagaac | 300 |
| ctcaacggag | ggctgcggag | atcggtagcg | cctgctgccc | ccaccagttg tgacttctca | 360 |
| ccaggagatt | tggtttgggc | caagatggag | ggttacccct | ggtggccttg tctggtttac | 420 |
| aaccacccct | tgatggaac | attcatccgc | gagaaaggga | aatcagtccg tgttcatgta | 480 |
| cagtttttg | atgacagccc | aacaaggggc | tgggttagca | aaaggctttt aaagccatat | 540 |
| acaggttcaa | aatcaaagga | agcccagaag | ggaggtcatt | tttacagtgc aaagcctgaa | 600 |
| atactgagag | caatgcaacg | tgcagatgaa | gccttaaata | agacaagat taagaggctt | 660 |
| gaattggcag | tttgtgatga | gccctcagag | ccagaagagg | aagaagagat ggaggtaggc | 720 |
| acaacttacg | taacagataa | gagtgaagaa | gataatgaaa | ttgagagtga agaggaagta | 780 |
| cagcctaaga | cacaaggatc | taggcgaagt | agccgccaaa | taaaaaacg aagggtcata | 840 |
| tcagattctg | agagtgacat | tggtggctct | gatgtggaat | ttaagccaga cactaaggag | 900 |
| gaaggaagca | gtgatgaaat | aagcagtgga | gtgggggata | gtgagagtga aggcctgaac | 960 |
| agccctgtca | aagttgctcg | aaagcggaag | agaatggtga | ctggaaatgg ctctcttaaa | 1020 |
| aggaaaagct | ctaggaagga | aacgccctca | gccaccaaac | aagcaactag catttcatca | 1080 |
| gaaaccaaga | atactttgag | agctttctct | gcccctcaaa | attctgaatc ccaagcccac | 1140 |
| gttagtggag | gtggtgatga | cagtagtcgc | cctactgttt | ggtatcatga aactttagaa | 1200 |
| tggcttaagg | aggaaaagag | aagagatgag | cacaggagga | ggcctgatca ccccgatttt | 1260 |
| gatgcatcta | cactctatgt | gcctgaggat | ttcctcaatt | cttgtactcc tgggatgagg | 1320 |
| aagtggtggc | agattaagtc | tcagaacttt | gatcttgtca | tctgttacaa ggtggggaaa | 1380 |
| ttttatgagc | tgtaccacat | ggatgctctt | attggagtca | gtgaactggg gctggtattc | 1440 |
| atgaaaggca | actgggccca | ttctggcttt | cctgaaattg | catttggccg ttattcagat | 1500 |
| tccctggtgc | agaagggcta | taagtagca | cgagtggaac | agactgagac tccagaaatg | 1560 |
| atggaggcac | gatgtagaaa | gatggcacat | atatccaagt | atgatagagt ggtgaggagg | 1620 |
| gagatctgta | ggatcattac | caagggtaca | cagacttaca | gtgtgctgga aggtgatccc | 1680 |
| tctgagaact | acagtaagta | tcttcttagc | ctcaaagaaa | aagaggaaga ttcttctggc | 1740 |
| catactcgtg | catatggtgt | gtgctttgtt | gatacttcac | tgggaaagtt tttcataggt | 1800 |
| cagttttcag | atgatcgcca | ttgttcgaga | tttaggactc | tagtggcaca ctatccccca | 1860 |
| gtacaagttt | tatttgaaaa | aggaaatctc | tcaaaggaaa | ctaaaacaat tctaaagagt | 1920 |
| tcattgtcct | gttctcttca | ggaaggtctg | atacccggct | cccagttttg ggatgcatcc | 1980 |

```
aaaactttga gaactctcct tgaggaagaa tattttaggg aaaagctaag tgatggcatt    2040
ggggtgatgt taccccaggt gcttaaaggt atgacttcag agtctgattc cattgggttg    2100
acaccaggag agaaaagtga attggccctc tctgctctag gtggttgtgt cttctacctc    2160
aaaaaatgcc ttattgatca ggagcttttta tcaatggcta attttgaaga atatattccc   2220
ttggattctg acacagtcag cactacaaga tctggtgcta tcttcaccaa agcctatcaa    2280
cgaatggtgc tagatgcagt gacattaaac aacttggaga ttttttctgaa tggaacaaat   2340 ggttctactg aaggaaccct actagagagg gttgatactt gccatactcc ttttggtaag    2400
cggctcctaa agcaatggct ttgtgcccca ctctgtaacc attatgctat taatgatcgt    2460
ctagatgcca tagaagacct catggttgtg cctgacaaaa tctccgaagt tgtagagctt    2520
ctaaagaagc ttccagatct tgagaggcta ctcagtaaaa ttcataatgt tgggtctccc    2580
ctgaagagtc agaaccaccc agacagcagg gctataatgt atgaagaaac tacatacagc    2640
aagaagaaga ttattgattt tctttctgct ctggaaggat tcaaagtaat gtgtaaaatt    2700
atagggatca tggaagaagt tgctgatggt ttaagtcta aaatccttaa gcaggtcatc     2760
tctctgcaga caaaaaatcc tgaaggtcgt tttcctgatt tgactgtaga attgaaccga    2820
tgggatacag cctttgacca tgaaaaggct cgaaagactg gacttattac tcccaaagca    2880
ggctttgact ctgattatga ccaagctctt gctgacataa gagaaaatga acagagcctc    2940
ctggaatacc tagagaaaca gcgcaacaga attggctgta ggaccatagt ctattggggg    3000
attggtagga accgttacca gctggaaatt cctgagaatt tcaccactcg caatttgcca    3060
gaagaatacg agttgaaatc taccaagaag ggctgtaaac gatactggac caaaactatt    3120
gaaaagaagt tggctaatct cataaatgct gaagaacgga gggatgtatc attgaaggac    3180
tgcatgcggc gactgttcta taactttgat aaaaattaca aggactggca gtctgctgta    3240
gagtgtatcg cagtgttgga tgttttactg tgcctggcta actatagtcg aggggtgat    3300 ggtcctatgt gtcgcccagt aattctgttg ccggaagata cccccccctt cttagagctt    3360
aaaggatcac gccatccttg cattacgaag acttttttg gagatgattt tattcctaat    3420
gacattctaa taggctgtga ggaagaggag caggaaaatg gcaaagccta ttgtgtgctt    3480
gttactggac aaatatgggg ggcaagtct acgcttatga gacaggctgg cttattagct    3540
gtaatggccc agatggggttg ttacgtccct gctgaagtgt gcaggctcac accaattgat    3600
agagtgttta ctagacttgg tgcctcagac agaataatgt caggtgaaag tacatttttt    3660
gttgaattaa gtgaaactgc cagcatactc atgcatgcaa cagcacattc tctggtgctt    3720
gtggatgaat taggaagagg tactgcaaca tttgatggga cggcaatagc aaatgcagtt    3780
gttaaagaac ttgctgagac tataaaatgt cgtacattat tttcaactca ctaccattca    3840
ttagtagaag attattctca aaatgttgct gtgcgcctag acatatggc atgcatggta    3900 gaaaatgaat gtgaagaccc cagccaggag actattacgt tcctctataa attcattaag    3960
ggagcttgtc ctaaaagcta tggctttaat gcagcaaggc ttgctaatct cccagaggaa    4020
gttattcaaa agggacatag aaaagcaaga gaatttgaga gatgaatca gtcactacga    4080 ttatttcggg aagtttgcct ggctagtgaa aggtcaactg tagatgctga agctgtccat    4140
aaattgctga ctttgattaa ggaattatag actgactaca ttggaagctt tgagttgact    4200
tctgaccaaa ggtggtaaat tcagacaaca ttatgatcta ataaacttta tttttttaaaa   4260 atga                                                                  4264
```

```
<210> SEQ ID NO 24
<211> LENGTH: 1360
<212> TYPE: PRT
<213> ORGANISM: Homo sapiens

<400> SEQUENCE: 24

Met Ser Arg Gln Ser Thr Leu Tyr Ser Phe Phe Pro Lys Ser Pro Ala
1               5                   10                  15

Leu Ser Asp Ala Asn Lys Ala Ser Ala Arg Ala Ser Arg Glu Gly Gly
                20                  25                  30

Arg Ala Ala Ala Pro Gly Ala Ser Pro Ser Pro Gly Gly Asp Ala
            35                  40                  45

Ala Trp Ser Glu Ala Gly Pro Gly Pro Arg Pro Leu Ala Arg Ser Ala
    50                  55                  60

Ser Pro Pro Lys Ala Lys Asn Leu Asn Gly Gly Leu Arg Arg Ser Val
65                  70                  75                  80

Ala Pro Ala Ala Pro Thr Ser Cys Asp Phe Ser Pro Gly Asp Leu Val
                85                  90                  95

Trp Ala Lys Met Glu Gly Tyr Pro Trp Trp Pro Cys Leu Val Tyr Asn
            100                 105                 110

His Pro Phe Asp Gly Thr Phe Ile Arg Glu Lys Gly Lys Ser Val Arg
        115                 120                 125

Val His Val Gln Phe Phe Asp Asp Ser Pro Thr Arg Gly Trp Val Ser
    130                 135                 140

Lys Arg Leu Leu Lys Pro Tyr Thr Gly Ser Lys Ser Lys Glu Ala Gln
145                 150                 155                 160

Lys Gly Gly His Phe Tyr Ser Ala Lys Pro Glu Ile Leu Arg Ala Met
                165                 170                 175

Gln Arg Ala Asp Glu Ala Leu Asn Lys Asp Lys Ile Lys Arg Leu Glu
            180                 185                 190

Leu Ala Val Cys Asp Glu Pro Ser Glu Pro Glu Glu Glu Glu Met
        195                 200                 205

Glu Val Gly Thr Thr Tyr Val Thr Asp Lys Ser Glu Glu Asp Asn Glu
    210                 215                 220

Ile Glu Ser Glu Glu Glu Val Gln Pro Lys Thr Gln Gly Ser Arg Arg
225                 230                 235                 240

Ser Ser Arg Gln Ile Lys Lys Arg Arg Val Ile Ser Asp Ser Glu Ser
                245                 250                 255

Asp Ile Gly Gly Ser Asp Val Glu Phe Lys Pro Asp Thr Lys Glu Glu
            260                 265                 270

Gly Ser Ser Asp Glu Ile Ser Ser Gly Val Gly Asp Ser Glu Ser Glu
        275                 280                 285

Gly Leu Asn Ser Pro Val Lys Val Ala Arg Lys Arg Lys Arg Met Val
    290                 295                 300

Thr Gly Asn Gly Ser Leu Lys Arg Lys Ser Arg Lys Glu Thr Pro
305                 310                 315                 320

Ser Ala Thr Lys Gln Ala Thr Ser Ile Ser Ser Glu Thr Lys Asn Thr
                325                 330                 335

Leu Arg Ala Phe Ser Ala Pro Gln Asn Ser Glu Ser Gln Ala His Val
            340                 345                 350

Ser Gly Gly Gly Asp Asp Ser Ser Arg Pro Thr Val Trp Tyr His Glu
        355                 360                 365

Thr Leu Glu Trp Leu Lys Glu Glu Lys Arg Arg Asp Glu His Arg Arg
    370                 375                 380
```

```
Arg Pro Asp His Pro Asp Phe Asp Ala Ser Thr Leu Tyr Val Pro Glu
385                 390                 395                 400

Asp Phe Leu Asn Ser Cys Thr Pro Gly Met Arg Lys Trp Trp Gln Ile
            405                 410                 415

Lys Ser Gln Asn Phe Asp Leu Val Ile Cys Tyr Lys Val Gly Lys Phe
            420                 425                 430

Tyr Glu Leu Tyr His Met Asp Ala Leu Ile Gly Val Ser Glu Leu Gly
        435                 440                 445

Leu Val Phe Met Lys Gly Asn Trp Ala His Ser Gly Phe Pro Glu Ile
        450                 455                 460

Ala Phe Gly Arg Tyr Ser Asp Ser Leu Val Gln Lys Gly Tyr Lys Val
465                 470                 475                 480

Ala Arg Val Glu Gln Thr Glu Thr Pro Glu Met Met Glu Ala Arg Cys
                485                 490                 495

Arg Lys Met Ala His Ile Ser Lys Tyr Asp Arg Val Val Arg Arg Glu
            500                 505                 510

Ile Cys Arg Ile Ile Thr Lys Gly Thr Gln Thr Tyr Ser Val Leu Glu
            515                 520                 525

Gly Asp Pro Ser Glu Asn Tyr Ser Lys Tyr Leu Leu Ser Leu Lys Glu
530                 535                 540

Lys Glu Glu Asp Ser Ser Gly His Thr Arg Ala Tyr Gly Val Cys Phe
545                 550                 555                 560

Val Asp Thr Ser Leu Gly Lys Phe Phe Ile Gly Gln Phe Ser Asp Asp
            565                 570                 575

Arg His Cys Ser Arg Phe Arg Thr Leu Val Ala His Tyr Pro Pro Val
            580                 585                 590

Gln Val Leu Phe Glu Lys Gly Asn Leu Ser Lys Glu Thr Lys Thr Ile
        595                 600                 605

Leu Lys Ser Ser Leu Ser Cys Ser Leu Gln Glu Gly Leu Ile Pro Gly
        610                 615                 620

Ser Gln Phe Trp Asp Ala Ser Lys Thr Leu Arg Thr Leu Leu Glu Glu
625                 630                 635                 640

Glu Tyr Phe Arg Glu Lys Leu Ser Asp Gly Ile Gly Val Met Leu Pro
                645                 650                 655

Gln Val Leu Lys Gly Met Thr Ser Glu Ser Asp Ser Ile Gly Leu Thr
            660                 665                 670

Pro Gly Glu Lys Ser Glu Leu Ala Leu Ser Ala Leu Gly Gly Cys Val
            675                 680                 685

Phe Tyr Leu Lys Lys Cys Leu Ile Asp Gln Glu Leu Leu Ser Met Ala
        690                 695                 700

Asn Phe Glu Glu Tyr Ile Pro Leu Asp Ser Asp Thr Val Ser Thr Thr
705                 710                 715                 720

Arg Ser Gly Ala Ile Phe Thr Lys Ala Tyr Gln Arg Met Val Leu Asp
                725                 730                 735

Ala Val Thr Leu Asn Asn Leu Glu Ile Phe Leu Asn Gly Thr Asn Gly
            740                 745                 750

Ser Thr Glu Gly Thr Leu Leu Glu Arg Val Asp Thr Cys His Thr Pro
        755                 760                 765

Phe Gly Lys Arg Leu Leu Lys Gln Trp Leu Cys Ala Pro Leu Cys Asn
        770                 775                 780

His Tyr Ala Ile Asn Asp Arg Leu Asp Ala Ile Glu Asp Leu Met Val
785                 790                 795                 800
```

```
Val Pro Asp Lys Ile Ser Glu Val Val Glu Leu Leu Lys Lys Leu Pro
            805                 810                 815

Asp Leu Glu Arg Leu Leu Ser Lys Ile His Asn Val Gly Ser Pro Leu
            820                 825                 830

Lys Ser Gln Asn His Pro Asp Ser Arg Ala Ile Met Tyr Glu Glu Thr
            835                 840                 845

Thr Tyr Ser Lys Lys Lys Ile Ile Asp Phe Leu Ser Ala Leu Glu Gly
        850                 855                 860

Phe Lys Val Met Cys Lys Ile Gly Ile Met Glu Glu Val Ala Asp
865                 870                 875                 880

Gly Phe Lys Ser Lys Ile Leu Lys Gln Val Ile Ser Leu Gln Thr Lys
                885                 890                 895

Asn Pro Glu Gly Arg Phe Pro Asp Leu Thr Val Glu Leu Asn Arg Trp
            900                 905                 910

Asp Thr Ala Phe Asp His Glu Lys Ala Arg Lys Thr Gly Leu Ile Thr
            915                 920                 925

Pro Lys Ala Gly Phe Asp Ser Asp Tyr Asp Gln Ala Leu Ala Asp Ile
        930                 935                 940

Arg Glu Asn Glu Gln Ser Leu Leu Glu Tyr Leu Glu Lys Gln Arg Asn
945                 950                 955                 960

Arg Ile Gly Cys Arg Thr Ile Val Tyr Trp Gly Ile Gly Arg Asn Arg
                965                 970                 975

Tyr Gln Leu Glu Ile Pro Glu Asn Phe Thr Thr Arg Asn Leu Pro Glu
            980                 985                 990

Glu Tyr Glu Leu Lys Ser Thr Lys  Lys Gly Cys Lys Arg  Tyr Trp Thr
            995                 1000                 1005

Lys Thr  Ile Glu Lys Lys Leu  Ala Asn Leu Ile Asn  Ala Glu Glu
     1010                 1015                 1020

Arg Arg  Asp Val Ser Leu Lys  Asp Cys Met Arg Arg  Leu Phe Tyr
     1025                 1030                 1035

Asn Phe  Asp Lys Asn Tyr Lys  Asp Trp Gln Ser Ala  Val Glu Cys
     1040                 1045                 1050

Ile Ala  Val Leu Asp Val Leu  Leu Cys Leu Ala Asn  Tyr Ser Arg
     1055                 1060                 1065

Gly Gly  Asp Gly Pro Met Cys  Arg Pro Val Ile Leu  Leu Pro Glu
     1070                 1075                 1080

Asp Thr  Pro Pro Phe Leu Glu  Leu Lys Gly Ser Arg  His Pro Cys
     1085                 1090                 1095

Ile Thr  Lys Thr Phe Phe Gly  Asp Asp Phe Ile Pro  Asn Asp Ile
     1100                 1105                 1110

Leu Ile  Gly Cys Glu Glu Glu  Glu Gln Glu Asn Gly  Lys Ala Tyr
     1115                 1120                 1125

Cys Val  Leu Val Thr Gly Pro  Asn Met Gly Gly Lys  Ser Thr Leu
     1130                 1135                 1140

Met Arg  Gln Ala Gly Leu Leu  Ala Val Met Ala Gln  Met Gly Cys
     1145                 1150                 1155

Tyr Val  Pro Ala Glu Val Cys  Arg Leu Thr Pro Ile  Asp Arg Val
     1160                 1165                 1170

Phe Thr  Arg Leu Gly Ala Ser  Asp Arg Ile Met Ser  Gly Glu Ser
     1175                 1180                 1185

Thr Phe  Phe Val Glu Leu Ser  Glu Thr Ala Ser Ile  Leu Met His
     1190                 1195                 1200

Ala Thr  Ala His Ser Leu Val  Leu Val Asp Glu Leu  Gly Arg Gly
```

| | | | | | | | | |
|---|---|---|---|---|---|---|---|---|
| | 1205 | | | 1210 | | | 1215 | |
| Thr Ala | Thr Phe | Asp Gly | Thr Ala | Ile Ala | Asn Ala | Val Val Lys | | |
| | 1220 | | | 1225 | | | 1230 | |
| Glu Leu | Ala Glu | Thr Ile | Lys Cys | Arg Thr | Leu Phe | Ser Thr His | | |
| | 1235 | | | 1240 | | | 1245 | |
| Tyr His | Ser Leu | Val Glu | Asp Tyr | Ser Gln | Asn Val | Ala Val Arg | | |
| | 1250 | | | 1255 | | | 1260 | |
| Leu Gly | His Met | Ala Cys | Met Val | Glu Asn | Glu Cys | Glu Asp Pro | | |
| | 1265 | | | 1270 | | | 1275 | |
| Ser Gln | Glu Thr | Ile Thr | Phe Leu | Tyr Lys | Phe Ile | Lys Gly Ala | | |
| | 1280 | | | 1285 | | | 1290 | |
| Cys Pro | Lys Ser | Tyr Gly | Phe Asn | Ala Ala | Arg Leu | Ala Asn Leu | | |
| | 1295 | | | 1300 | | | 1305 | |
| Pro Glu | Glu Val | Ile Gln | Lys Gly | His Arg | Lys Ala | Arg Glu Phe | | |
| | 1310 | | | 1315 | | | 1320 | |
| Glu Lys | Met Asn | Gln Ser | Leu Arg | Leu Phe | Arg Glu | Val Cys Leu | | |
| | 1325 | | | 1330 | | | 1335 | |
| Ala Ser | Glu Arg | Ser Thr | Val Asp | Ala Glu | Ala Val | His Lys Leu | | |
| | 1340 | | | 1345 | | | 1350 | |
| Leu Thr | Leu Ile | Lys Glu | Leu | | | | | |
| | 1355 | | | 1360 | | | | |

<210> SEQ ID NO 25
<211> LENGTH: 1445
<212> TYPE: DNA
<213> ORGANISM: Homo sapiens

<400> SEQUENCE: 25

```
ttttttttt tgatgttctc cagtgcctca gtggcagcag aactggccct gtatcaggcc      60
gctaccgcca ctccatgacc aacctccctg catacccccc cccccagcac ccctcccaca    120
ggaccgcttc tgtgtttggg acccaccagg cctttgcacc atacaacaaa ccctcactct    180
ccggggcccg gtctgcgccc aggctgaaca ccacgaacgc ctgggacgca gctcctcctt    240
ccctggggag ccagcccctc taccgctcca gcctctccca cctgggaccg cagcacctgc    300
ccccaggatc ctccacctcc ggtgcagtca gtgcctccct ccccagcggt ccctcaagca    360
gcccaggcga gcgtccctgc cactgtgccc atgcagatgc caagccagca gagtcagcag    420
gcgctcgctg gagcgacccg aagccagagc agagcagagc aggtcataaa actacacgga    480
agagctgaaa gtgccccccag atgaggactg catcatctgc atggagaagc tgtccgcagc    540
gtctggatac agcgatgtga ctgacagcaa ggcaatgggg ccctggctg tgggctgcct    600
caccaagtgc agccacgcct tccacctgct gtgcctcctg gccatgtact gcaacggcaa    660
taagggccct gagcacccca atcccggaaa gccgttcact gccagagggt ttcccgccag    720
tgctaccttc cagacaacgc cagggccgca agcctccagg ggcttccaga acccggagac    780
actggctgac attccggcct ccccacagct gctgaccgat ggccactaca tgacgctgcc    840
cgtgtctccg gaccagctgc cctgtgacga ccccatggcg ggcagcggag cgccccgt    900
gctgcgggtg ggccatgacc acggctgcca ccagcagcca cgtatctgca acgcgcccct    960
ccctggcccct ggaccctatc gtacagaacc tgctaaggcc atcaaaccta ttgatcggaa   1020
gtcagtccat cagatttgct ctgggccagt ggtactgagt ctaagcactg cagtgaagga   1080
gttagtagaa aacagtctgg atgctggtgc cactaatatt gatctaaagc ttaaggacta   1140
tggaatggat ctcattgaag tttcaggcaa tggatgtggg gtagaagaag aaaacttcga   1200
```

-continued

```
aggcttaatg atgtcaccat ttctacctgc cacgtctcgg cgaaggttgg gactcgactg    1260
gtgtttgatc acgatgggaa aatcatccag aagacccct accccaccc cagagggacc     1320 acagtcagcg tgaagcagtt attttctacg ctacctgtgc gccataagga atttcaaagg    1380
aatattaaga agaaacatgc tgcttcccct tcgccttctg ccgtgattgt cagttttaac    1440
cggaa                                                                1445
```

<210> SEQ ID NO 26
<211> LENGTH: 270
<212> TYPE: PRT
<213> ORGANISM: Homo sapiens

<400> SEQUENCE: 26

```
Met Glu Lys Leu Ser Ala Ala Ser Gly Tyr Ser Asp Val Thr Asp Ser
1               5                   10                  15

Lys Ala Met Gly Pro Leu Ala Val Gly Cys Leu Thr Lys Cys Ser His
            20                  25                  30

Ala Phe His Leu Leu Cys Leu Leu Ala Met Tyr Cys Asn Gly Asn Lys
        35                  40                  45

Gly Pro Glu His Pro Asn Pro Gly Lys Pro Phe Thr Ala Arg Gly Phe
    50                  55                  60

Pro Ala Ser Ala Thr Phe Gln Thr Thr Pro Gly Pro Gln Ala Ser Arg
65                  70                  75                  80

Gly Phe Gln Asn Pro Glu Thr Leu Ala Asp Ile Pro Ala Ser Pro Gln
                85                  90                  95

Leu Leu Thr Asp Gly His Tyr Met Thr Leu Pro Val Ser Pro Asp Gln
            100                 105                 110

Leu Pro Cys Asp Asp Pro Met Ala Gly Ser Gly Ala Pro Val Leu
        115                 120                 125

Arg Val Gly His Asp His Gly Cys His Gln Gln Pro Arg Ile Cys Asn
    130                 135                 140

Ala Pro Leu Pro Gly Pro Gly Pro Tyr Arg Thr Glu Pro Ala Lys Ala
145                 150                 155                 160

Ile Lys Pro Ile Asp Arg Lys Ser Val His Gln Ile Cys Ser Gly Pro
                165                 170                 175

Val Val Leu Ser Leu Ser Thr Ala Val Lys Glu Leu Val Glu Asn Ser
            180                 185                 190

Leu Asp Ala Gly Ala Thr Asn Ile Asp Leu Lys Leu Lys Asp Tyr Gly
        195                 200                 205

Met Asp Leu Ile Glu Val Ser Gly Asn Gly Cys Gly Val Glu Glu Glu
    210                 215                 220

Asn Phe Glu Gly Leu Met Met Ser Pro Phe Leu Pro Ala Thr Ser Arg
225                 230                 235                 240

Arg Arg Leu Gly Leu Asp Trp Cys Leu Ile Thr Met Gly Lys Ser Ser
                245                 250                 255

Arg Arg Pro Pro Thr Pro Thr Pro Glu Gly Pro Gln Ser Ala
            260                 265                 270
```

<210> SEQ ID NO 27
<211> LENGTH: 795
<212> TYPE: DNA
<213> ORGANISM: Homo sapiens

<400> SEQUENCE: 27

```
atgtgtcctt ggcggcctag actaggccgt cgctgtatgg tgagccccag ggaggcggat     60
```

```
ctgggccccc agaaggacac ccgcctggat tgccccgta gcccggcccg ggcccctcgg        120
gagcagaaca gccttggtga ggtggacagg aggggacctc gcgagcagac gcgcgcgcca        180
gcgacagcag ccccgccccg gcctctcggg agccggggg cagaggctgc ggagccccag        240
gagggtctat cagccacagt ctctgcatgt ttccaagagc aacaggaaat gaacacattg        300
caggggccag tgtcattcaa agatgtggct gtggatttca cccaggagga gtggcggcaa        360
ctggaccctg atgagaagat agcatacggg gatgtgatgt tggagaacta cagccatcta        420
gtttctgtgg ggtatgatta tcaccaagcc aaacatcatc atggagtgga ggtgaaggaa        480
gtggagcagg gagaggagcc gtggataatg gaaggtgaat tccatgtca acatagtcca        540 gaacctgcta aggccatcaa acctattgat cggaagtcag tccatcagat ttgctctggg        600
ccagtggtac tgagtctaag cactgcagtg aaggagttag tagaaaacag tctggatgct        660
ggtgccacta atattgatct aaagcttaag gactatggag tggatctcat tgaagtttca        720
gacaatggat gtggggtaga agaagaaaac tttgaaggct taatctcttt cagctctgaa        780
acatcacaca tgtaa                                                         795
```

```
<210> SEQ ID NO 28
<211> LENGTH: 260
<212> TYPE: PRT
<213> ORGANISM: Homo sapiens

<400> SEQUENCE: 28

Met Cys Pro Trp Arg Pro Arg Leu Gly Arg Arg Cys Met Val Ser Pro
1               5                   10                  15

Arg Glu Ala Asp Leu Gly Pro Gln Lys Asp Thr Arg Leu Asp Leu Pro
            20                  25                  30

Arg Ser Pro Ala Arg Ala Pro Arg Glu Gln Asn Ser Leu Gly Glu Val
        35                  40                  45

Asp Arg Arg Gly Pro Arg Glu Gln Thr Arg Ala Pro Ala Thr Ala Ala
    50                  55                  60

Pro Pro Arg Pro Leu Gly Ser Arg Gly Ala Glu Ala Ala Glu Pro Gln
65                  70                  75                  80

Glu Gly Leu Ser Ala Thr Val Ser Ala Cys Phe Gln Glu Gln Gln Glu
                85                  90                  95

Met Asn Thr Leu Gln Gly Pro Val Ser Phe Lys Asp Val Ala Val Asp
            100                 105                 110

Phe Thr Gln Glu Glu Trp Arg Gln Leu Asp Pro Asp Glu Lys Ile Ala
        115                 120                 125

Tyr Gly Asp Val Met Leu Glu Asn Tyr Ser His Leu Val Ser Val Gly
    130                 135                 140

Tyr Asp Tyr His Gln Ala Lys His His His Gly Val Glu Val Lys Glu
145                 150                 155                 160

Val Glu Gln Gly Glu Glu Pro Trp Ile Met Glu Gly Glu Phe Pro Cys
                165                 170                 175

Gln His Ser Pro Glu Pro Ala Lys Ala Ile Lys Pro Ile Asp Arg Lys
            180                 185                 190

Ser Val His Gln Ile Cys Ser Gly Pro Val Val Leu Ser Leu Ser Thr
        195                 200                 205

Ala Val Lys Glu Leu Val Glu Asn Ser Leu Asp Ala Gly Ala Thr Asn
    210                 215                 220

Ile Asp Leu Lys Leu Lys Asp Tyr Gly Val Asp Leu Ile Glu Val Ser
225                 230                 235                 240
```

Asp Asn Gly Cys Gly Val Glu Glu Glu Asn Phe Glu Gly Leu Ile Ser
            245                 250                 255

Phe Ser Ser Glu
        260

<210> SEQ ID NO 29
<211> LENGTH: 3218
<212> TYPE: DNA
<213> ORGANISM: Saccharomyces cerevisiae

<400> SEQUENCE: 29

| | | | | | |
|---|---|---|---|---|---|
| aaataggaat | gtgatacctt | ctattgcatg | caaagatagt | gtaggaggcg | ctgctattgc | 60 |
| caaagacttt | tgagaccgct | tgctgtttca | ttatagttga | ggagttctcg | aagacgagaa | 120 |
| attagcagtt | ttcggtgttt | agtaatcgcg | ctagcatgct | aggacaattt | aactgcaaaa | 180 |
| ttttgatacg | atagtgatag | taaatggaag | gtaaaaataa | catagaccta | tcaataagca | 240 |
| atgtctctca | gaataaaagc | acttgatgca | tcagtggtta | acaaaattgc | tgcaggtgag | 300 |
| atcataatat | cccccgtaaa | tgctctcaaa | gaaatgatgg | agaattccat | cgatgcgaat | 360 |
| gctacaatga | ttgatattct | agtcaaggaa | ggaggaatta | aggtacttca | aataacagat | 420 |
| aacggatctg | gaattaataa | agcagacctg | ccaatcttat | gtgagcgatt | cacgacgtcc | 480 |
| aaattacaaa | aattcgaaga | tttgagtcag | attcaaacgt | atggattccg | aggagaagct | 540 |
| ttagccagta | tctcacatgt | ggcaagagtc | acagtaacga | caaaagttaa | agaagacaga | 600 |
| tgtgcatgga | gagtttcata | tgcagaaggt | aagatgttgg | aaagccccaa | acctgttgct | 660 |
| ggaaaagacg | gtaccacgat | cctagttgaa | gacctttttt | tcaatattcc | ttctagatta | 720 |
| agggccttga | ggtcccataa | tgatgaatac | tctaaaatat | tagatgttgt | cgggcgatac | 780 |
| gccattcatt | ccaaggacat | tggctttttct | tgtaaaaagt | tcggagactc | taattattct | 840 |
| ttatcagtta | aaccttcata | tacagtccag | gataggatta | ggactgtgtt | caataaatct | 900 |
| gtggcttcga | atttaattac | ttttcatatc | agcaaagtag | aagatttaaa | cctggaaagc | 960 |
| gttgatggaa | aggtgtgtaa | tttgaatttc | atatccaaaa | agtccatttc | attaattttt | 1020 |
| ttcattaata | atagactagt | gacatgtgat | cttctaagaa | gagctttgaa | cagcgtttac | 1080 |
| tccaattatc | tgccaaaggg | cttcagacct | tttatttatt | tgggaattgt | tatagatccg | 1140 |
| gcggctgttg | atgttaacgt | tcacccgaca | agagagagg | ttcgtttcct | gagccaagat | 1200 |
| gagatcatag | agaaaatcgc | caatcaattg | cacgccgaat | tatctgccat | tgatacttca | 1260 |
| cgtactttca | aggcttcttc | aatttcaaca | aacaagccag | agtcattgat | accatttaat | 1320 |
| gacaccatag | aaagtgatag | gaataggaag | agtctccgac | aagcccaagt | ggtagagaat | 1380 |
| tcatatacga | cagccaatag | tcaactaagg | aaagcgaaaa | gacaagagaa | taaactagtc | 1440 |
| agaatagatg | cttcacaagc | taaaattacg | tcatttttat | cctcaagtca | acagttcaac | 1500 |
| tttgaaggat | cgtctacaaa | gcgacaactg | agtgaaccca | aggtaacaaa | tgtaagccac | 1560 |
| tcccaagagg | cagaaaagct | gacactaaat | gaaagcgaac | aaccgcgtga | tgccaataca | 1620 |
| atcaatgata | atgacttgaa | ggatcaacct | aagaagaaac | aaaagttggg | ggattataaa | 1680 |
| gttccaagca | ttgccgatga | cgaaaagaat | gcactcccga | tttcaaaaga | cgggtatatt | 1740 |
| agagtaccta | aggagcgagt | taatgttaat | cttcgagta | tcaagaaatt | gcgtgaaaaa | 1800 |
| gtagatgatt | cgatacatcg | agaactaaca | gacattttg | caaatttgaa | ttacgttggg | 1860 |
| gttgtagatg | aggaaagaag | attagccgct | attcagcatg | acttaaagct | tttttaata | 1920 |

```
gattacggat ctgtgtgcta tgagctattc tatcagattg gtttgacaga cttcgcaaac    1980
tttggtaaga taaacctaca gagtacaaat gtgtcagatg atatagtttt gtataatctc    2040
ctatcagaat ttgacgagtt aaatgacgat gcttccaaag aaaaaataat tagtaaaata    2100
tgggacatga gcagtatgct aaatgagtac tattccatag aattggtgaa tgatggtcta    2160
gataatgact aaagtctgt gaagctaaaa tctctaccac tacttttaaa aggctacatt     2220
ccatctctgg tcaagttacc attttttata tatcgcctgg gtaaagaagt tgattgggag    2280
gatgaacaag agtgtctaga tggtatttta agagagattg cattactcta tatacctgat    2340
atggttccga aagtcgatac actcgatgca tcgttgtcag aagacgaaaa agcccagttt    2400
ataaatagaa aggaacacat atcctcatta ctagaacacg ttctcttccc ttgtatcaaa    2460
cgaaggttcc tggcccctag acacattctc aaggatgtcg tggaaatagc caacttcca    2520 gatctataca aagttttga gaggtgttaa ctttaaaacg ttttggctgt aataccaaag     2580 ttttgttta tttcctgagt gtgattgtgt ttcatttgaa agtgtatgcc ctttccttta     2640
acgattcatc cgcgagattt caaggatat gaaatatggt tgcagttagg aaagtatgtc     2700
agaaatgtat attcggattg aaactcttct aatagttctg aagtcacttg gttccgtatt    2760
gttttcgtcc tcttcctcaa gcaacgattc ttgtctaagc ttattcaacg gtaccaaaga    2820
cccgagtcct tttatgagag aaaacatttc atcattttc aactcaatta tcttaatatc     2880
attttgtagt attttgaaaa caggatggta aaacgaatca cctgaatcta gaagctgtac    2940
cttgtcccat aaaagttta atttactgag cctttcggtc aagtaaacta gtttatctag     3000
ttttgaaccg aatattgtgg gcagatttgc agtaagttca gttagatcta ctaaaagttg    3060
tttgacagca gccgattcca caaaatttg gtaaaaggag atgaaagaga cctcgcgcgt     3120
aatggtttgc atcaccatcg gatgtctgtt gaaaaactca cttttttgcat ggaagttatt    3180 aacaataaga ctaatgatta ccttagaata atgtataa                             3218
```

<210> SEQ ID NO 30
<211> LENGTH: 769
<212> TYPE: PRT
<213> ORGANISM: Saccharomyces cerevisiae

<400> SEQUENCE: 30

```
Met Ser Leu Arg Ile Lys Ala Leu Asp Ala Ser Val Val Asn Lys Ile
1               5                   10                  15

Ala Ala Gly Glu Ile Ile Ile Ser Pro Val Asn Ala Leu Lys Glu Met
            20                  25                  30

Met Glu Asn Ser Ile Asp Ala Asn Ala Thr Met Ile Asp Ile Leu Val
        35                  40                  45

Lys Glu Gly Gly Ile Lys Val Leu Gln Ile Thr Asp Asn Gly Ser Gly
    50                  55                  60

Ile Asn Lys Ala Asp Leu Pro Ile Leu Cys Glu Arg Phe Thr Thr Ser
65                  70                  75                  80

Lys Leu Gln Lys Phe Glu Asp Leu Ser Gln Ile Gln Thr Tyr Gly Phe
                85                  90                  95

Arg Gly Glu Ala Leu Ala Ser Ile Ser His Val Ala Arg Val Thr Val
            100                 105                 110

Thr Thr Lys Val Lys Glu Asp Arg Cys Ala Trp Arg Val Ser Tyr Ala
        115                 120                 125

Glu Gly Lys Met Leu Glu Ser Pro Lys Pro Val Ala Gly Lys Asp Gly
    130                 135                 140
```

```
Thr Thr Ile Leu Val Glu Asp Leu Phe Phe Asn Ile Pro Ser Arg Leu
145                 150                 155                 160

Arg Ala Leu Arg Ser His Asn Asp Glu Tyr Ser Lys Ile Leu Asp Val
            165                 170                 175

Val Gly Arg Tyr Ala Ile His Ser Lys Asp Ile Gly Phe Ser Cys Lys
        180                 185                 190

Lys Phe Gly Asp Ser Asn Tyr Ser Leu Ser Val Lys Pro Ser Tyr Thr
    195                 200                 205

Val Gln Asp Arg Ile Arg Thr Val Phe Asn Lys Ser Val Ala Ser Asn
210                 215                 220

Leu Ile Thr Phe His Ile Ser Lys Val Glu Asp Leu Asn Leu Glu Ser
225                 230                 235                 240

Val Asp Gly Lys Val Cys Asn Leu Asn Phe Ile Ser Lys Lys Ser Ile
            245                 250                 255

Ser Leu Ile Phe Phe Ile Asn Asn Arg Leu Val Thr Cys Asp Leu Leu
        260                 265                 270

Arg Arg Ala Leu Asn Ser Val Tyr Ser Asn Tyr Leu Pro Lys Gly Phe
    275                 280                 285

Arg Pro Phe Ile Tyr Leu Gly Ile Val Ile Asp Pro Ala Ala Val Asp
290                 295                 300

Val Asn Val His Pro Thr Lys Arg Glu Val Arg Phe Leu Ser Gln Asp
305                 310                 315                 320

Glu Ile Ile Glu Lys Ile Ala Asn Gln Leu His Ala Glu Leu Ser Ala
            325                 330                 335

Ile Asp Thr Ser Arg Thr Phe Lys Ala Ser Ser Ile Ser Thr Asn Lys
        340                 345                 350

Pro Glu Ser Leu Ile Pro Phe Asn Asp Thr Ile Glu Ser Asp Arg Asn
    355                 360                 365

Arg Lys Ser Leu Arg Gln Ala Gln Val Val Glu Asn Ser Tyr Thr Thr
370                 375                 380

Ala Asn Ser Gln Leu Arg Lys Ala Lys Arg Gln Glu Asn Lys Leu Val
385                 390                 395                 400

Arg Ile Asp Ala Ser Gln Ala Lys Ile Thr Ser Phe Leu Ser Ser Ser
            405                 410                 415

Gln Gln Phe Asn Phe Glu Gly Ser Ser Thr Lys Arg Gln Leu Ser Glu
        420                 425                 430

Pro Lys Val Thr Asn Val Ser His Ser Gln Glu Ala Glu Lys Leu Thr
    435                 440                 445

Leu Asn Glu Ser Glu Gln Pro Arg Asp Ala Asn Thr Ile Asn Asp Asn
450                 455                 460

Asp Leu Lys Asp Gln Pro Lys Lys Gln Lys Leu Gly Asp Tyr Lys
465                 470                 475                 480

Val Pro Ser Ile Ala Asp Asp Glu Lys Asn Ala Leu Pro Ile Ser Lys
            485                 490                 495

Asp Gly Tyr Ile Arg Val Pro Lys Glu Arg Val Asn Val Asn Leu Thr
        500                 505                 510

Ser Ile Lys Lys Leu Arg Glu Lys Val Asp Asp Ser Ile His Arg Glu
    515                 520                 525

Leu Thr Asp Ile Phe Ala Asn Leu Asn Tyr Val Gly Val Val Asp Glu
530                 535                 540

Glu Arg Arg Leu Ala Ala Ile Gln His Asp Leu Lys Leu Phe Leu Ile
545                 550                 555                 560

Asp Tyr Gly Ser Val Cys Tyr Glu Leu Phe Tyr Gln Ile Gly Leu Thr
```

Asp Phe Ala Asn Phe Gly Lys Ile Asn Leu Gln Ser Thr Asn Val Ser
            580                 585                 590

Asp Asp Ile Val Leu Tyr Asn Leu Leu Ser Glu Phe Asp Glu Leu Asn
        595                 600                 605

Asp Asp Ala Ser Lys Glu Lys Ile Ile Ser Lys Ile Trp Asp Met Ser
    610                 615                 620

Ser Met Leu Asn Glu Tyr Tyr Ser Ile Glu Leu Val Asn Asp Gly Leu
625                 630                 635                 640

Asp Asn Asp Leu Lys Ser Val Lys Leu Lys Ser Leu Pro Leu Leu
                645                 650                 655

Lys Gly Tyr Ile Pro Ser Leu Val Lys Leu Pro Phe Phe Ile Tyr Arg
                660                 665                 670

Leu Gly Lys Glu Val Asp Trp Glu Asp Glu Gln Glu Cys Leu Asp Gly
            675                 680                 685

Ile Leu Arg Glu Ile Ala Leu Leu Tyr Ile Pro Asp Met Val Pro Lys
        690                 695                 700

Val Asp Thr Leu Asp Ala Ser Leu Ser Glu Asp Glu Lys Ala Gln Phe
705                 710                 715                 720

Ile Asn Arg Lys Glu His Ile Ser Ser Leu Leu Glu His Val Leu Phe
                725                 730                 735

Pro Cys Ile Lys Arg Arg Phe Leu Ala Pro Arg His Ile Leu Lys Asp
            740                 745                 750

Val Val Glu Ile Ala Asn Leu Pro Asp Leu Tyr Lys Val Phe Glu Arg
        755                 760                 765

Cys

<210> SEQ ID NO 31
<211> LENGTH: 3056
<212> TYPE: DNA
<213> ORGANISM: Mus musculus

<400> SEQUENCE: 31

```
gaattccggt gaaggtcctg aagaatttcc agattcctga gtatcattgg aggagacaga      60
taacctgtcg tcaggtaacg atggtgtata tgcaacagaa atgggtgttc ctggagacgc     120
gtcttttccc gagagcggca ccgcaactct cccgcggtga ctgtgactgg aggagtcctg     180
catccatgga gcaaaccgaa ggcgtgagta cagaatgtgc taaggccatc aagcctattg     240
atgggaagtc agtccatcaa atttgttctg ggcaggtgat actcagttta agcaccgctg     300
tgaaggagtt gatagaaaat agtgtagatg ctggtgctac tactattgat ctaaggctta     360
aagactatgg ggtggacctc attgaagttt cagacaatgg atgtggggta gaagaagaaa     420
actttgaagg tctagctctg aaacatcaca catctaagat tcaagagttt gccgacctca     480
cgcaggttga aactttcggc tttcggggga agctctgag ctctctgtgt gcactaagtg     540
atgtcactat atctacctgc acgggtctg caagcgttgg gactcgactg gtgtttgacc     600
ataatgggaa aatcacccag aaaactccct accccgacc taaggaacc acagtcagtg     660
tgcagcactt attttataca ctacccgtgc gttacaaaga gtttcagagg aacattaaaa     720
aggagtattc caaatggtg caggtcttac aggcgtactg tatcatctca gcaggcgtcc     780
gtgtaagctg cactaatcag ctcggacagg ggaagcggca cgctgtggtg tgcacaagcg     840
gcacgtctgg catgaaggaa aatatcgggt ctgtgtttgg ccagaagcag ttgcaaagcc     900
tcattccttt tgttcagctg ccccctagtg acgctgtgtg tgaagagtac ggcctgagca     960
```

```
cttcaggacg ccacaaaacc tttctacgt tcgggcttc atttcacagt gcacgcacgg    1020
cgccgggagg agtgcaacag acaggcagtt tttcttcatc aatcagaggc cctgtgaccc    1080
agcaaaggtc tctaagcttg tcaatgaggt tttatcacat gtataaccgg catcagtacc    1140
catttgtcgt ccttaacgtt tccgttgact cagaatgtgt ggatattaat gtaactccag    1200
ataaaaggca aattctacta caagaagaga agctattgct ggccgttta aagacctcct    1260 tgataggaat gtttgacagt gatgcaaaca agcttaatgt caaccagcag ccactgctag    1320
atgttgaagg taacttagta aagctgcata ctgcagaact agaaaagcct gtgccaggaa    1380
agcaagataa ctctccttca ctgaagagca cagcagacga gaaagggta gcatccatct    1440 ccaggctgag agaggccttt tctcttcatc tactaaaga gatcaagtct agggtccag    1500 agactgctga actgacacgg agttttccaa gtgagaaaag gggcgtgtta tcctcttatc    1560
cttcagacgt catctcttac agaggcctcc gtggctcgca ggacaaattg gtgagtccca    1620
cggacagccc tggtgactgt atggacagag agaaaataga aaaagactca gggctcagca    1680
gcacctcagc tggctctgag gaagagttca gcaccccaga agtggccagt agctttagca    1740
gtgactataa cgtgagctcc ctagaagaca gaccttctca ggaaaccata aactgtggtg    1800
acctggactg ccgtcctcca ggtacaggac agtccttgaa gccagaagac catggatatc    1860
aatgcaaagc tctacctcta gctcgtctgt cacccacaaa tgccaagcgc ttcaagacag    1920
aggaaagacc ctcaaatgtc aacatttctc aaagattgcc tggtcctcag agcacctcag    1980
cagctgaggt cgatgtagcc ataaaaatga ataagagaat cgtgctcctc gagttctctc    2040
tgagttctct agctaagcga atgaagcagt tacagcacct aaaggcgcag aacaaacatg    2100
aactgagtta cagaaaattt agggccaaga tttgccctgg agaaaaccaa gcagcagaag    2160
atgaactcag aaaagagatt agtaaatcga tgtttgcaga gatggagatc ttgggtcagt    2220
ttaacctggg atttatagta accaaactga agaggacct cttcctggtg gaccagcatg    2280
ctgcggatga gaagtacaac tttgagatgc tgcagcagca cacggtgctc caggcgcaga    2340
ggctcatcac acccccagact ctgaacttaa ctgctgtcaa tgaagctgta ctgatagaaa    2400
atctggaaat attcagaaag aatggctttg actttgtcat tgatgaggat gctccagtca    2460
ctgaaagggc taaattgatt tccttaccaa ctagtaaaaa ctggacccttt ggaccccaag    2520 atatagatga actgatcttt atgttaagtg acagccctgg ggtcatgtgc cggccctcac    2580
gagtcagaca gatgtttgct tccagagcct gtcggaagtc agtgatgatt ggaacggcgc    2640
tcaatgcgag cgagatgaag aagctcatca cccacatggg tgagatggac caccctgga    2700 actgccccca cggcaggcca accatgaggc acgttgccaa tctggatgtc atctctcaga    2760
actgacacac cccttgtagc atagagttta ttacagattg ttcggtttgc aaagagaagg    2820 tttttaagtaa tctgattatc gttgtacaaa aattagcatg ctgctttaat gtactggatc    2880
catttaaaag cagtgttaag gcaggcatga tggagtgttc ctctagctca gctacttggg    2940
tgatccggtg ggagctcatg tgagcccagg actttgagac cactccgagc cacattcatg    3000
agactcaatt caaggacaaa aaaaaaaaga tatttttgaa gccttttaaa aaaaa    3056
```

<210> SEQ ID NO 32
<211> LENGTH: 859
<212> TYPE: PRT
<213> ORGANISM: Mus musculus

<400> SEQUENCE: 32

-continued

```
Met Glu Gln Thr Glu Gly Val Ser Thr Glu Cys Ala Lys Ala Ile Lys
1               5                   10                  15

Pro Ile Asp Gly Lys Ser Val His Gln Ile Cys Ser Gly Gln Val Ile
            20                  25                  30

Leu Ser Leu Ser Thr Ala Val Lys Glu Leu Ile Glu Asn Ser Val Asp
        35                  40                  45

Ala Gly Ala Thr Thr Ile Asp Leu Arg Leu Lys Asp Tyr Gly Val Asp
50                  55                  60

Leu Ile Glu Val Ser Asp Asn Gly Cys Gly Val Glu Glu Asn Phe
65                  70                  75                  80

Glu Gly Leu Ala Leu Lys His His Thr Ser Lys Ile Gln Glu Phe Ala
                85                  90                  95

Asp Leu Thr Gln Val Glu Thr Phe Gly Phe Arg Gly Glu Ala Leu Ser
            100                 105                 110

Ser Leu Cys Ala Leu Ser Asp Val Thr Ile Ser Thr Cys His Gly Ser
        115                 120                 125

Ala Ser Val Gly Thr Arg Leu Val Phe Asp His Asn Gly Lys Ile Thr
    130                 135                 140

Gln Lys Thr Pro Tyr Pro Arg Pro Lys Gly Thr Thr Val Ser Val Gln
145                 150                 155                 160

His Leu Phe Tyr Thr Leu Pro Val Arg Tyr Lys Glu Phe Gln Arg Asn
                165                 170                 175

Ile Lys Lys Glu Tyr Ser Lys Met Val Gln Val Leu Gln Ala Tyr Cys
            180                 185                 190

Ile Ile Ser Ala Gly Val Arg Val Ser Cys Thr Asn Gln Leu Gly Gln
        195                 200                 205

Gly Lys Arg His Ala Val Val Cys Thr Ser Gly Thr Ser Gly Met Lys
    210                 215                 220

Glu Asn Ile Gly Ser Val Phe Gly Gln Lys Gln Leu Gln Ser Leu Ile
225                 230                 235                 240

Pro Phe Val Gln Leu Pro Ser Asp Ala Val Cys Glu Glu Tyr Gly
                245                 250                 255

Leu Ser Thr Ser Gly Arg His Lys Thr Phe Ser Thr Phe Arg Ala Ser
            260                 265                 270

Phe His Ser Ala Arg Thr Ala Pro Gly Gly Val Gln Gln Thr Gly Ser
        275                 280                 285

Phe Ser Ser Ser Ile Arg Gly Pro Val Thr Gln Gln Arg Ser Leu Ser
    290                 295                 300

Leu Ser Met Arg Phe Tyr His Met Tyr Asn Arg His Gln Tyr Pro Phe
305                 310                 315                 320

Val Val Leu Asn Val Ser Val Asp Ser Glu Cys Val Asp Ile Asn Val
                325                 330                 335

Thr Pro Asp Lys Arg Gln Ile Leu Leu Gln Glu Glu Lys Leu Leu Leu
            340                 345                 350

Ala Val Leu Lys Thr Ser Leu Ile Gly Met Phe Asp Ser Asp Ala Asn
        355                 360                 365

Lys Leu Asn Val Asn Gln Gln Pro Leu Leu Asp Val Glu Gly Asn Leu
    370                 375                 380

Val Lys Leu His Thr Ala Glu Leu Glu Lys Pro Val Pro Gly Lys Gln
385                 390                 395                 400

Asp Asn Ser Pro Ser Leu Lys Ser Thr Ala Asp Glu Lys Arg Val Ala
                405                 410                 415

Ser Ile Ser Arg Leu Arg Glu Ala Phe Ser Leu His Pro Thr Lys Glu
```

-continued

```
                420             425             430
Ile Lys Ser Arg Gly Pro Glu Thr Ala Glu Leu Thr Arg Ser Phe Pro
            435             440             445
Ser Glu Lys Arg Gly Val Leu Ser Ser Tyr Pro Ser Asp Val Ile Ser
            450             455             460
Tyr Arg Gly Leu Arg Gly Ser Gln Asp Lys Leu Val Ser Pro Thr Asp
465             470             475             480
Ser Pro Gly Asp Cys Met Asp Arg Glu Lys Ile Glu Lys Asp Ser Gly
                485             490             495
Leu Ser Ser Thr Ser Ala Gly Ser Glu Glu Phe Ser Thr Pro Glu
            500             505             510
Val Ala Ser Ser Phe Ser Ser Asp Tyr Asn Val Ser Ser Leu Glu Asp
            515             520             525
Arg Pro Ser Gln Glu Thr Ile Asn Cys Gly Asp Leu Asp Cys Arg Pro
            530             535             540
Pro Gly Thr Gly Gln Ser Leu Lys Pro Glu Asp His Gly Tyr Gln Cys
545             550             555             560
Lys Ala Leu Pro Leu Ala Arg Leu Ser Pro Thr Asn Ala Lys Arg Phe
            565             570             575
Lys Thr Glu Glu Arg Pro Ser Asn Val Asn Ile Ser Gln Arg Leu Pro
            580             585             590
Gly Pro Gln Ser Thr Ser Ala Ala Glu Val Asp Val Ala Ile Lys Met
            595             600             605
Asn Lys Arg Ile Val Leu Leu Glu Phe Ser Leu Ser Ser Leu Ala Lys
            610             615             620
Arg Met Lys Gln Leu Gln His Leu Lys Ala Gln Asn Lys His Glu Leu
625             630             635             640
Ser Tyr Arg Lys Phe Arg Ala Lys Ile Cys Pro Gly Glu Asn Gln Ala
            645             650             655
Ala Glu Asp Glu Leu Arg Lys Glu Ile Ser Lys Ser Met Phe Ala Glu
            660             665             670
Met Glu Ile Leu Gly Gln Phe Asn Leu Gly Phe Ile Val Thr Lys Leu
            675             680             685
Lys Glu Asp Leu Phe Leu Val Asp Gln His Ala Ala Asp Glu Lys Tyr
            690             695             700
Asn Phe Glu Met Leu Gln Gln His Thr Val Leu Gln Ala Gln Arg Leu
705             710             715             720
Ile Thr Pro Gln Thr Leu Asn Leu Thr Ala Val Asn Glu Ala Val Leu
            725             730             735
Ile Glu Asn Leu Glu Ile Phe Arg Lys Asn Gly Phe Asp Phe Val Ile
            740             745             750
Asp Glu Asp Ala Pro Val Thr Glu Arg Ala Lys Leu Ile Ser Leu Pro
            755             760             765
Thr Ser Lys Asn Trp Thr Phe Gly Pro Gln Asp Ile Asp Glu Leu Ile
            770             775             780
Phe Met Leu Ser Asp Ser Pro Gly Val Met Cys Arg Pro Ser Arg Val
785             790             795             800
Arg Gln Met Phe Ala Ser Arg Ala Cys Arg Lys Ser Val Met Ile Gly
            805             810             815
Thr Ala Leu Asn Ala Ser Glu Met Lys Lys Leu Ile Thr His Met Gly
            820             825             830
Glu Met Asp His Pro Trp Asn Cys Pro His Gly Arg Pro Thr Met Arg
            835             840             845
```

His Val Ala Asn Leu Asp Val Ile Ser Gln Asn
        850                 855

<210> SEQ ID NO 33
<211> LENGTH: 399
<212> TYPE: DNA
<213> ORGANISM: Mus musculus

<400> SEQUENCE: 33

```
atggagcaaa ccgaaggcgt gagtacagaa tgtgctaagg ccatcaagcc tattgatggg      60
aagtcagtcc atcaaatttg ttctgggcag gtgatactca gtttaagcac cgctgtgaag     120
gagttgatag aaatagtgt agatgctggt gctactacta ttgatctaag gcttaaagac      180
tatggggtgg acctcattga agtttcagac aatggatgtg gggtagaaga agaaaacttt     240
gaaggtctag ctctgaaaca tcacacatct aagattcaag agtttgccga cctcacgcag     300
gttgaaactt tcggctttcg ggggaagct ctgagctctc tgtgtgcact aagtgatgtc      360
actatatcta cctgccacgg gtctgcaagc gttgggact                             399
```

<210> SEQ ID NO 34
<211> LENGTH: 133
<212> TYPE: PRT
<213> ORGANISM: Mus musculus

<400> SEQUENCE: 34

Met Glu Gln Thr Glu Gly Val Ser Thr Glu Cys Ala Lys Ala Ile Lys
1               5                   10                  15

Pro Ile Asp Gly Lys Ser Val His Gln Ile Cys Ser Gly Gln Val Ile
            20                  25                  30

Leu Ser Leu Ser Thr Ala Val Lys Glu Leu Ile Glu Asn Ser Val Asp
        35                  40                  45

Ala Gly Ala Thr Thr Ile Asp Leu Arg Leu Lys Asp Tyr Gly Val Asp
    50                  55                  60

Leu Ile Glu Val Ser Asp Asn Gly Cys Gly Val Glu Glu Glu Asn Phe
65                  70                  75                  80

Glu Gly Leu Ala Leu Lys His His Thr Ser Lys Ile Gln Glu Phe Ala
                85                  90                  95

Asp Leu Thr Gln Val Glu Thr Phe Gly Phe Arg Gly Glu Ala Leu Ser
            100                 105                 110

Ser Leu Cys Ala Leu Ser Asp Val Thr Ile Ser Thr Cys His Gly Ser
        115                 120                 125

Ala Ser Val Gly Thr
    130

<210> SEQ ID NO 35
<211> LENGTH: 3099
<212> TYPE: DNA
<213> ORGANISM: Arabidopsis thaliana

<400> SEQUENCE: 35

```
gtcttcttct tcatccttgt ctcaccttcg attttggcgg caaaacataa accctaaggg      60
ttttctcact ctctctctct cttctcacac acacagtccc agagtacggt ggtgttgatt     120
cgattgagga gattcatctg tttataggt ttagcaaatg caaggagatt cttctccgtc      180
tccgacgact actagctctc ctttgataag acctataaac agaaacgtaa ttcacagaat     240
ctgttccggt caagtcatct tagacctctc ttcggccgtc aaggagcttg tcgagaatag     300
```

```
tctcgacgcc ggcgccacca gtatagagat taacctccga gactacgcg aagactattt      360 tcaggtcatt gacaatggtt gtggcatttc cccaaccaat ttcaaggttc ttgcacttaa      420
gcatcatact tctaaattag aggatttcac agatcttttg aatttgacta cttatggttt      480
tagaggagaa gccttgagct ctctctgtgc attgggaaat ctcactgtgg aaacaagaac      540
aaagaatgag ccagttgcta cgctcttgac gtttgatcat tctggtttgc ttactgctga      600
aaagaagact gctcgccaaa ttggtaccac tgtcactgtt aggaagttgt tctctaattt      660
acctgtacga agcaaagagt ttaagcggaa tatacgcaaa gaatatggga agcttgtatc      720
tttattgaac gcatatgcgc ttattgcgaa aggagtgcgg tttgtctgct ctaacacgac      780
tgggaaaaac ccaaagtctg ttgtgctgaa cacacaaggg aggggttcac ttaaagataa      840
tatcataaca gttttcggca ttagtacctt tacaagtcta cagcctgtaa gtatatgtgt      900
atcagaagat tgtagagttg aagggtttct ttccaagcct ggacaggta ctggacgcaa       960 tttagcagat cgacagtatt tctttataaa tggtcggcct gtagatatgc aaaagtcag     1020 caagttggtg aatgagttat ataaagatac aagttctcgg aaatatccag ttaccattct     1080 ggatttatt gtgcctggtg gagcatgtga tttgaatgtc acgccgata aaagaaaggt       1140 gttcttttct gacgagactt ctgttatcgg ttctttgagg gaaggtctga acgagatata     1200
ttcctccagt aatgcgtctt atattgttaa taggttcgag gagaattcgg agcaaccaga     1260
taaggctgga gtttcgtcgt ttcagaagaa atcaaatctt ttgtcagaag ggatagttct     1320
ggatgtcagt tctaaaacaa gactagggga agctattgag aaagaaaatc catccttaag     1380
ggaggttgaa attgataata gttcgccaat ggagaagttt aagtttgaga tcaaggcatg     1440
tgggacgaag aaaggggaag ttctcttatc agtccatgat gtaactcacc ttgacaagac     1500
acctagcaaa ggtttgcctc agttaaatgt gactgagaaa gttactgatg caagtaaaga     1560
cttgagcagc cgctctagct ttgcccagtc aactttgaat acttttgtta ccatgggaaa     1620
aagaaaacat gaaaacataa gcaccatcct ctctgaaaca cctgtcctca gaaaccaaac     1680
ttctagttat cgtgtggaga aaagcaaatt tgaagttcgt gccttagctt caaggtgtct     1740
cgtggaaggc gatcaacttg atgatatggt catctcaaag gaagatatga caccaagcga     1800
aagagattct gaactaggca atcggatttc tcctggaaca caagctgata atgttgaaag     1860
acatgagaga gaacatgaaa agcctataag gtttgaagaa ccaacatcag ataacacact     1920
caccaagggg gatgtggaaa gggtttcaga ggacaatcca cggtgcagtc agccactgcg     1980
atctgtggcc acagtgctgg attccccagc tcagtcaacc ggtcctaaaa tgttttccac     2040
attagaattt agtttccaaa acctcaggac aaggaggtta gagaggctgt cgagattgca     2100
gtccacaggt tatgtatcta aatgtatgaa tacgccacag cctaaaaagt gctttgccgc     2160
tgcaacatta gagttatctc aaccggatga tgaagagcga aaagcaaggg ctttagctgc     2220
agctacttct gagctggaaa ggcttttttcg aaaagaggat ttcaggagaa tgcaggtact     2280
cgggcaattc aatctggggt tcatcattgc aaaattggag cgagatctgt tcattgtgga     2340
tcagcatgca gctgatgaga aattcaactt cgaacattta gcaaggtcaa ctgtcctgaa     2400
ccagcaaccc ttactccagc ctttgaactt ggaactctct ccagaagaag aagtaactgt     2460
gttaatgcac atgatatta tcagggaaaa tggctttctt ctagaggaga tccaagtgc      2520 tcctcccgga aaacacttta gactacgagc cattccttat agcaagaata tcacctttgg    2580
agtcgaagat cttaaagacc tgatctcaac tctaggagat aaccatgggg aatgttcggt     2640
tgctagtagc tacaaaaacca gcaaaacaga ttcgatttgt ccatcacgag tccgtgcaat    2700
```

```
gctagcatcc cgagcatgca gatcatctgt gatgatcgga gatccactca gaaaaaacga    2760
aatgcagaag atagtagaac acttggcaga tctcgaatct ccttggaatt gcccacacgg    2820
acgaccaaca atgcgtcatc ttgtggactt gacaacttta ctcacattac ctgatgacga    2880
caatgtcaat gatgatgatg atgatgatgc aaccatctca ttggcatgaa cactcaaaag    2940
tcttaacgta tttagatgtg agaatcctta agattaacat tgaggaacac tcggttataa    3000
ctacaatcgt aaatgtaaat tgtcttagtc tatatgatct ttttggtcac aacaggtaat    3060
ttcattttcc tttgattact tctcgtgaaa aaacaaatt                           3099
```

<210> SEQ ID NO 36
<211> LENGTH: 923
<212> TYPE: PRT
<213> ORGANISM: Arabidopsis thaliana

<400> SEQUENCE: 36

```
Met Gln Gly Asp Ser Ser Pro Ser Pro Thr Thr Thr Ser Ser Pro Leu
1               5                   10                  15

Ile Arg Pro Ile Asn Arg Asn Val Ile His Arg Ile Cys Ser Gly Gln
            20                  25                  30

Val Ile Leu Asp Leu Ser Ser Ala Val Lys Glu Leu Val Glu Asn Ser
        35                  40                  45

Leu Asp Ala Gly Ala Thr Ser Ile Glu Ile Asn Leu Arg Asp Tyr Gly
    50                  55                  60

Glu Asp Tyr Phe Gln Val Ile Asp Asn Gly Cys Gly Ile Ser Pro Thr
65                  70                  75                  80

Asn Phe Lys Val Leu Ala Leu Lys His His Thr Ser Lys Leu Glu Asp
                85                  90                  95

Phe Thr Asp Leu Leu Asn Leu Thr Thr Tyr Gly Phe Arg Gly Glu Ala
            100                 105                 110

Leu Ser Ser Leu Cys Ala Leu Gly Asn Leu Thr Val Glu Thr Arg Thr
        115                 120                 125

Lys Asn Glu Pro Val Ala Thr Leu Leu Thr Phe Asp His Ser Gly Leu
    130                 135                 140

Leu Thr Ala Glu Lys Lys Thr Ala Arg Gln Ile Gly Thr Thr Val Thr
145                 150                 155                 160

Val Arg Lys Leu Phe Ser Asn Leu Pro Val Arg Ser Lys Glu Phe Lys
                165                 170                 175

Arg Asn Ile Arg Lys Glu Tyr Gly Lys Leu Val Ser Leu Leu Asn Ala
            180                 185                 190

Tyr Ala Leu Ile Ala Lys Gly Val Arg Phe Val Cys Ser Asn Thr Thr
        195                 200                 205

Gly Lys Asn Pro Lys Ser Val Val Leu Asn Thr Gln Gly Arg Gly Ser
    210                 215                 220

Leu Lys Asp Asn Ile Ile Thr Val Phe Gly Ile Ser Thr Phe Thr Ser
225                 230                 235                 240

Leu Gln Pro Val Ser Ile Cys Val Ser Glu Asp Cys Arg Val Glu Gly
                245                 250                 255

Phe Leu Ser Lys Pro Gly Gln Gly Thr Gly Arg Asn Leu Ala Asp Arg
            260                 265                 270

Gln Tyr Phe Phe Ile Asn Gly Arg Pro Val Asp Met Pro Lys Val Ser
        275                 280                 285

Lys Leu Val Asn Glu Leu Tyr Lys Asp Thr Ser Ser Arg Lys Tyr Pro
    290                 295                 300
```

-continued

```
Val Thr Ile Leu Asp Phe Ile Val Pro Gly Gly Ala Cys Asp Leu Asn
305                 310                 315                 320

Val Thr Pro Asp Lys Arg Lys Val Phe Phe Ser Asp Glu Thr Ser Val
            325                 330                 335

Ile Gly Ser Leu Arg Glu Gly Leu Asn Glu Ile Tyr Ser Ser Ser Asn
            340                 345                 350

Ala Ser Tyr Ile Val Asn Arg Phe Glu Glu Asn Ser Glu Gln Pro Asp
            355                 360                 365

Lys Ala Gly Val Ser Ser Phe Gln Lys Lys Ser Asn Leu Leu Ser Glu
            370                 375                 380

Gly Ile Val Leu Asp Val Ser Ser Lys Thr Arg Leu Gly Glu Ala Ile
385                 390                 395                 400

Glu Lys Glu Asn Pro Ser Leu Arg Glu Val Glu Ile Asp Asn Ser Ser
            405                 410                 415

Pro Met Glu Lys Phe Lys Phe Glu Ile Lys Ala Cys Gly Thr Lys Lys
            420                 425                 430

Gly Glu Gly Ser Leu Ser Val His Asp Val Thr His Leu Asp Lys Thr
            435                 440                 445

Pro Ser Lys Gly Leu Pro Gln Leu Asn Val Thr Glu Lys Val Thr Asp
            450                 455                 460

Ala Ser Lys Asp Leu Ser Ser Arg Ser Ser Phe Ala Gln Ser Thr Leu
465                 470                 475                 480

Asn Thr Phe Val Thr Met Gly Lys Arg Lys His Glu Asn Ile Ser Thr
            485                 490                 495

Ile Leu Ser Glu Thr Pro Val Leu Arg Asn Gln Thr Ser Ser Tyr Arg
            500                 505                 510

Val Glu Lys Ser Lys Phe Glu Val Arg Ala Leu Ala Ser Arg Cys Leu
            515                 520                 525

Val Glu Gly Asp Gln Leu Asp Asp Met Val Ile Ser Lys Glu Asp Met
            530                 535                 540

Thr Pro Ser Glu Arg Asp Ser Glu Leu Gly Asn Arg Ile Ser Pro Gly
545                 550                 555                 560

Thr Gln Ala Asp Asn Val Glu Arg His Glu Arg Glu His Glu Lys Pro
            565                 570                 575

Ile Arg Phe Glu Glu Pro Thr Ser Asp Asn Thr Leu Thr Lys Gly Asp
            580                 585                 590

Val Glu Arg Val Ser Glu Asp Asn Pro Arg Cys Ser Gln Pro Leu Arg
            595                 600                 605

Ser Val Ala Thr Val Leu Asp Ser Pro Ala Gln Ser Thr Gly Pro Lys
            610                 615                 620

Met Phe Ser Thr Leu Glu Phe Ser Phe Gln Asn Leu Arg Thr Arg Arg
625                 630                 635                 640

Leu Glu Arg Leu Ser Arg Leu Gln Ser Thr Gly Tyr Val Ser Lys Cys
            645                 650                 655

Met Asn Thr Pro Gln Pro Lys Lys Cys Phe Ala Ala Ala Thr Leu Glu
            660                 665                 670

Leu Ser Gln Pro Asp Asp Glu Glu Arg Lys Ala Arg Ala Leu Ala Ala
            675                 680                 685

Ala Thr Ser Glu Leu Glu Arg Leu Phe Arg Lys Glu Asp Phe Arg Arg
            690                 695                 700

Met Gln Val Leu Gly Gln Phe Asn Leu Gly Phe Ile Ile Ala Lys Leu
705                 710                 715                 720
```

```
Glu Arg Asp Leu Phe Ile Val Asp Gln His Ala Ala Asp Glu Lys Phe
                725                 730                 735

Asn Phe Glu His Leu Ala Arg Ser Thr Val Leu Asn Gln Gln Pro Leu
            740                 745                 750

Leu Gln Pro Leu Asn Leu Glu Leu Ser Pro Glu Glu Val Thr Val
        755                 760                 765

Leu Met His Met Asp Ile Ile Arg Glu Asn Gly Phe Leu Leu Glu Glu
        770                 775                 780

Asn Pro Ser Ala Pro Pro Gly Lys His Phe Arg Leu Arg Ala Ile Pro
785                 790                 795                 800

Tyr Ser Lys Asn Ile Thr Phe Gly Val Glu Asp Leu Lys Asp Leu Ile
                805                 810                 815

Ser Thr Leu Gly Asp Asn His Gly Glu Cys Ser Val Ala Ser Ser Tyr
            820                 825                 830

Lys Thr Ser Lys Thr Asp Ser Ile Cys Pro Ser Arg Val Arg Ala Met
        835                 840                 845

Leu Ala Ser Arg Ala Cys Arg Ser Ser Val Met Ile Gly Asp Pro Leu
    850                 855                 860

Arg Lys Asn Glu Met Gln Lys Ile Val Glu His Leu Ala Asp Leu Glu
865                 870                 875                 880

Ser Pro Trp Asn Cys Pro His Gly Arg Pro Thr Met Arg His Leu Val
                885                 890                 895

Asp Leu Thr Thr Leu Leu Thr Leu Pro Asp Asp Asn Val Asn Asp
            900                 905                 910

Asp Asp Asp Asp Ala Thr Ile Ser Leu Ala
        915                 920

<210> SEQ ID NO 37
<211> LENGTH: 399
<212> TYPE: DNA
<213> ORGANISM: Arabidopsis thaliana

<400> SEQUENCE: 37
atgcaaggag attcttctcc gtctccgacg actactagct ctcctttgat aagacctata      60
aacagaaacg taattcacag aatctgttcc ggtcaagtca tcttagacct ctcttcggcc     120
gtcaaggagc ttgtcgagaa tagtctcgac gccggcgcca ccagtataga gattaacctc     180
cgagactacg gcgaagacta ttttcaggtc attgacaatg ttgtggcat tccccaacc      240 aatttcaagg ttcttgcact taagcatcat acttctaaat tagaggattt cacagatctt     300
ttgaatttga ctacttatgg ttttagagga gaagccttga gctctctctg tgcattggga     360
aatctcactg tggaaacaag aacaaagaat gagccagtt                             399

<210> SEQ ID NO 38
<211> LENGTH: 133
<212> TYPE: PRT
<213> ORGANISM: Arabidopsis thaliana

<400> SEQUENCE: 38

Met Gln Gly Asp Ser Ser Pro Ser Pro Thr Thr Thr Ser Ser Pro Leu
1               5                   10                  15

Ile Arg Pro Ile Asn Arg Asn Val Ile His Arg Ile Cys Ser Gly Gln
            20                  25                  30

Val Ile Leu Asp Leu Ser Ser Ala Val Lys Glu Leu Val Glu Asn Ser
        35                  40                  45

Leu Asp Ala Gly Ala Thr Ser Ile Glu Ile Asn Leu Arg Asp Tyr Gly
```

-continued

```
                    50                  55                  60
Glu Asp Tyr Phe Gln Val Ile Asp Asn Gly Cys Gly Ile Ser Pro Thr
 65                  70                  75                  80

Asn Phe Lys Val Leu Ala Leu Lys His His Thr Ser Lys Leu Glu Asp
                 85                  90                  95

Phe Thr Asp Leu Leu Asn Leu Thr Thr Tyr Gly Phe Arg Gly Glu Ala
            100                 105                 110

Leu Ser Ser Leu Cys Ala Leu Gly Asn Leu Thr Val Glu Thr Arg Thr
        115                 120                 125

Lys Asn Glu Pro Val
        130

<210> SEQ ID NO 39
<211> LENGTH: 2791
<212> TYPE: DNA
<213> ORGANISM: Homo sapiens
<220> FEATURE:
<221> NAME/KEY: CDS
<222> LOCATION: (77)..(673)
<300> PUBLICATION INFORMATION:
<308> DATABASE ACCESSION NUMBER: NM_02661
<309> DATABASE ENTRY DATE: 2003-12-13
<313> RELEVANT RESIDUES: (1)..(2791)

<400> SEQUENCE: 39
gaaccatcat taattgaagt gagattttc tggcctgaga cttgcaggga ggcaagaaga     60
cactctggac accact atg gac agc ctc ttg atg aac cgg agg aag ttt ctt    112
               Met Asp Ser Leu Leu Met Asn Arg Arg Lys Phe Leu
                 1               5                  10 tac caa ttc aaa aat gtc cgc tgg gct aag ggt cgg cgt gag acc tac      160
Tyr Gln Phe Lys Asn Val Arg Trp Ala Lys Gly Arg Arg Glu Thr Tyr
             15                  20                  25 ctg tgc tac gta gtg aag agg cgt gac agt gct aca tcc ttt tca ctg      208
Leu Cys Tyr Val Val Lys Arg Arg Asp Ser Ala Thr Ser Phe Ser Leu
         30                  35                  40 gac ttt ggt tat ctt cgc aat aag aac ggc tgc cac gtg gaa ttg ctc      256
Asp Phe Gly Tyr Leu Arg Asn Lys Asn Gly Cys His Val Glu Leu Leu
 45                  50                  55                  60 ttc ctc cgc tac atc tcg gac tgg gac cta gac cct ggc cgc tgc tac      304
Phe Leu Arg Tyr Ile Ser Asp Trp Asp Leu Asp Pro Gly Arg Cys Tyr
                 65                  70                  75 cgc gtc acc tgg ttc acc tcc tgg agc ccc tgc tac gac tgt gcc cga      352
Arg Val Thr Trp Phe Thr Ser Trp Ser Pro Cys Tyr Asp Cys Ala Arg
             80                  85                  90 cat gtg gcc gac ttt ctg cga ggg aac ccc aac ctc agt ctg agg atc      400
His Val Ala Asp Phe Leu Arg Gly Asn Pro Asn Leu Ser Leu Arg Ile
         95                 100                 105 ttc acc gcg cgc ctc tac ttc tgt gag gac cgc aag gct gag ccc gag      448
Phe Thr Ala Arg Leu Tyr Phe Cys Glu Asp Arg Lys Ala Glu Pro Glu
    110                 115                 120 ggg ctg cgg cgg ctg cac cgc gcc ggg gtg caa ata gcc atc atg acc      496
Gly Leu Arg Arg Leu His Arg Ala Gly Val Gln Ile Ala Ile Met Thr
125                 130                 135                 140 ttc aaa gat tat ttt tac tgc tgg aat act ttt gta gaa aac cat gaa      544
Phe Lys Asp Tyr Phe Tyr Cys Trp Asn Thr Phe Val Glu Asn His Glu
                145                 150                 155 aga act ttc aaa gcc tgg gaa ggg ctg cat gaa aat tca gtt cgt ctc      592
Arg Thr Phe Lys Ala Trp Glu Gly Leu His Glu Asn Ser Val Arg Leu
            160                 165                 170 tcc aga cag ctt cgg cgc atc ctt ttg ccc ctg tat gag gtt gat gac      640
```

-continued

```
Ser Arg Gln Leu Arg Arg Ile Leu Leu Pro Leu Tyr Glu Val Asp Asp
        175                 180                 185 tta cga gac gca ttt cgt act ttg gga ctt tga tagcaacttc caggaatgtc     693
Leu Arg Asp Ala Phe Arg Thr Leu Gly Leu
        190                 195 acacacgatg aaatatctct gctgaagaca gtggataaaa acagtcctt  caagtcttct     753 ctgtttttat tcttcaactc tcactttctt agagtttaca gaaaaaatat ttatatacga     813
ctctttaaaa agatctatgt cttgaaaata gagaaggaac acaggtctgg ccagggacgt     873
gctgcaattg gtgcagtttt gaatgcaaca ttgtcccta  ctgggaataa cagaactgca     933
ggacctggga gcatcctaaa gtgtcaacgt ttttctatga cttttaggta ggatgagagc     993
agaaggtaga tcctaaaaag catggtgaga ggatcaaatg ttttatatc  aacatccttt    1053 attatttgat tcatttgagt taacagtggt gttagtgata gattttctcta ttcttttccc   1113 ttgacgttta ctttcaagta acacaaactc ttccatcagg ccatgatcta taggacctcc    1173
taatgagagt atctgggtga ttgtgacccc aaaccatctc tccaaagcat aatatccaa     1233 tcatgcgctg tatgttttaa tcagcagaag catgttttta tgtttgtaca aagaagatt     1293 gttatgggtg gggatggagg tatagaccat gcatggtcac cttcaagcta ctttaataaa    1353
ggatcttaaa atgggcagga ggactgtgaa caagacaccc taataatggg ttgatgtctg    1413
aagtagcaaa tcttctggaa acgcaaactc ttttaaggaa gtccctaatt tagaaacacc    1473
cacaaacttc acatatcata attagcaaac aattggaagg aagttgcttg aatgttgggg    1533
agaggaaaat ctattggctc tcgtgggtct cttcatctca gaaatgccaa tcaggtcaag    1593
gtttgctaca ttttgtatgt gtgtgatgct tctcccaaag gtatattaac tatataagag    1653
agttgtgaca aaacagaatg ataaagctgc gaaccgtggc acacgctcat agttctagct    1713
gcttgggagg ttgaggaggg aggatggctt gaacacaggt gttcaaggcc agcctgggca    1773
acataacaag atcctgtctc tcaaaaaaaa aaaaaaaaa  aagaaagaga gagggccggg    1833
cgtggtggct cacgcctgta atcccagcac tttgggaggc cgagccgggc ggatcacctg    1893
tggtcaggag tttgagacca gcctggccaa catggcaaaa ccccgtctgt actcaaaatg    1953
caaaaattag ccaggcgtgg tagcaggcac ctgtaatccc agctacttgg gaggctgagg    2013
caggagaatc gcttgaaccc aggaggtgga ggttgcagta agctgagatc gtgccgttgc    2073
actccagcct gggcgacaag agcaagactc tgtctcagaa aaaaaaaaa  aaaagagaga    2133 gagagagaaa gagaacaata tttgggagag aaggatgggg aagcattgca aggaaattgt    2193
gctttatcca acaaaatgta aggagccaat aagggatccc tatttgtctc ttttggtgtc    2253
tatttgtccc taacaactgt ctttgacagt gagaaaaata ttcagaataa ccatatccct    2313
gtgccgttat tacctagcaa cccttgcaat gaagatgagc agatccacag gaaaacttga    2373
atgcacaact gtcttatttt aatcttattg tacataagtt tgtaaaagag ttaaaaattg    2433
ttacttcatg tattcattta tattttatat tattttgcgt ctaatgattt tttattaaca    2493
tgatttcctt ttctgatata ttgaaatgga gtctcaaagc ttcataaatt tataacttta    2553
gaaatgattc taataacaac gtatgtaatt gtaacattgc agtaatggtg ctacgaagcc    2613
atttctcttg attttagta  aacttttatg acagcaaatt tgcttctggc tcactttcaa    2673
tcagttaaat aaatgataaa taattttgga agctgtgaag ataaaatacc aaataaaata    2733
atataaaagt gatttatatg aagttaaaat aaaaatcag  tatgatggaa taaacttg      2791

<210> SEQ ID NO 40
```

```
<211> LENGTH: 198
<212> TYPE: PRT
<213> ORGANISM: Homo sapiens

<400> SEQUENCE: 40

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 41
<211> LENGTH: 20
<212> TYPE: DNA
<213> ORGANISM: Artificial
<220> FEATURE:
<223> OTHER INFORMATION: Oligonucleotide primer sequence

<400> SEQUENCE: 41
atggacagcc tcttgatgaa                                            20

<210> SEQ ID NO 42
<211> LENGTH: 20
<212> TYPE: DNA
<213> ORGANISM: Artificial
<220> FEATURE:
<223> OTHER INFORMATION: Oligonucleotide primer sequence

<400> SEQUENCE: 42
caggctttga aagttctttc                                            20

<210> SEQ ID NO 43
<211> LENGTH: 2440
<212> TYPE: DNA
<213> ORGANISM: Mus musculus
<220> FEATURE:
<221> NAME/KEY: misc_feature
<222> LOCATION: (2413)..(2413)
<223> OTHER INFORMATION: n is a, c, g, or t
```

<400> SEQUENCE: 43

```
ggcacgagca gcactgaagc agccttgctt gaagcaagct tcctttggcc taagactttg      60
agggagtcaa gaaagtcacg ctggagaccg atatggacag ccttctgatg aagcaaaaga     120
agtttcttta ccatttcaaa aatgtccgct gggccaaggg acggcatgag acctacctct     180
gctacgtggt gaagaggaga gatagtgcca cctcctgctc actggacttc ggccaccttc     240
gcaacaagtc tggctgccac gtggaattgt tgttcctacg ctacatctca gactgggacc     300
tggacccggg ccggtgttac cgcgtcacct ggttcacctc ctggagcccg tgctatgact     360
gtgcccgca cgtggctgag tttctgagat ggaaccctaa cctcagcctg aggattttca     420
ccgcgcgcct ctacttctgt gaagaccgca aggctgagcc tgaggggctg cggagactgc     480
accgcgctgg ggtccagatc gggatcatga ccttcaaaga ctattttac tgctggaata     540
catttgtaga aaatcgtgaa agaactttca aagcctggga agggctacat gaaaattctg     600
tccggctaac cagacaactt cggcgcatcc ttttgcccct tgtacgaagtc gatgacttgc     660
gagatgcatt tcgtatgttg ggattttgaa agcaacctcc tggaatgtca cacgtgatga     720
aatttctctg aagagactgg atagaaaaac aacccttcaa ctacatgttt ttcttcttaa     780
gtactcactt ttataagtgt aggggaaat tatatgactt tttaaaaaat acttgagctg     840
cacaggaccg ccagagcaat gatgtaactg agcttgctgt gcaacatcgc catctactgg     900
ggaacagcat aacttccaga ctttgggtcg tgaatgatgc tcttttttt caacagcatg     960
gaaaagcata tggagacgac cacacagttt gttacaccca ccctgtgttc cttgattcat    1020
ttgaattctc aggggtatca gtgacggatt cttctattct ttccctctaa ggctcacttt    1080
caggggtcct tttctgacaa ggtcacgggg ctgtcctaca gtctctgtct gagcaatcac    1140
aagccattct ctcaaaaaca ttaatactca ggcacatgct gtatgttttc actgtccgtc    1200
gtgtttttca catttgtatg tgaaagggct tggggtggga tttgaagaat gcacgatcgc    1260
ctctgggtga tttcaataaa ggatcttaaa atgcagatga ggactacgaa gaaatcactc    1320
tgaaaatgag ttcacgcctc aagaagcaaa tcccctggaa acacagactc ttttcatttt   1380
taatgtcat tagtttactc acagtcttat caagaagaag agttcaaggg ttcaacccaa     1440
ttttcagatc gcgtcccta aacatcagta attctgttaa agggatcaaa catccttatt    1500
tcttaactaa ctggtgcctt gctgtagaga aaggagcaaa gcgcccagat ccaaagtata    1560
tagttatcat agccaggaac cgctactcgt tttccattac aaatggcaaa ttcttccccg    1620
ggctctcctc atagtgcctg agacggacca cggaggtgat gaacctccgg attctctggc    1680
ccaacacggt ggaagctctg caagggcgca gagacagaat gcggcagaaa ttgccccga    1740
gtcccaactc tcctttcctt gcgaccttgg gaacaagact taaaggagcc tgtgacttag    1800
aaacttctag taatgggtac ctgggagtcg tttgagtatg gggcagtgat ttattctctg    1860
tgatggatgc caacacggtt aaacagaatt tttagttttt atatgtgtgt gatgctgctc    1920
ccccaaattg ttaactgtgt aagagggtgg caaatagggg aaagtggcat tcacctatag    1980
ttccagcatt caggaagctg aggcaggagg attgtaaatt tgaggccagt ctgagctgta    2040
aggtgagacc ctatttcaaa caacacagcc agaattgggt tctggtaaat catacttaac    2100
aagggaaaaa tgcaagacgc aagaccgtgg caaggaaatg acgctttgcc caacgaaatg    2160
taggaaacca acatagactc ccagtttgtc cctctttatg tctggtctcc ctaacaacga    2220
tctttgctaa tgagaaaaat attagaaaaa aatatccctg tgcaattatc acccagtcgc    2280
cattataatg caattaaaag gcccacaaga aatcctgtat acacgaccgt tatttattgt    2340
```

-continued

```
atgtaagttg ctgaggaaga ggagaaaaaa ataaagatca tccattcctt cctgcaaaaa      2400
aaaaaaaaaa aanaaaaaaa aaaaaaaaaa aaaaaaaaaa                            2440

<210> SEQ ID NO 44
<211> LENGTH: 198
<212> TYPE: PRT
<213> ORGANISM: Mus musculus

<400> SEQUENCE: 44
```

Met Asp Ser Leu Leu Met Lys Gln Lys Lys Phe Leu Tyr His Phe Lys
1               5                   10                  15

Asn Val Arg Trp Ala Lys Gly Arg His Glu Thr Tyr Leu Cys Tyr Val
            20                  25                  30

Val Lys Arg Arg Asp Ser Ala Thr Ser Cys Ser Leu Asp Phe Gly His
        35                  40                  45

Leu Arg Asn Lys Ser Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Glu
                85                  90                  95

Phe Leu Arg Trp Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Gly Ile Met Thr Phe Lys Asp Tyr
    130                 135                 140

Phe Tyr Cys Trp Asn Thr Phe Val Glu Asn Arg Glu Arg Thr Phe Lys
145                 150                 155                 160

Ala Trp Glu Gly Leu His Glu Asn Ser Val Arg Leu Thr Arg Gln Leu
                165                 170                 175

Arg Arg Ile Leu Leu Pro Leu Tyr Glu Val Asp Asp Leu Arg Asp Ala
            180                 185                 190

Phe Arg Met Leu Gly Phe
        195

```
<210> SEQ ID NO 45
<211> LENGTH: 24
<212> TYPE: DNA
<213> ORGANISM: Artificial Sequence
<220> FEATURE:
<223> OTHER INFORMATION: Oligonucleotide primer sequence

<400> SEQUENCE: 45
ggattttcag gtgcagattt tcag                                               24

<210> SEQ ID NO 46
<211> LENGTH: 21
<212> TYPE: DNA
<213> ORGANISM: Artificial Sequence
<220> FEATURE:
<223> OTHER INFORMATION: Oligonucleotide primer sequence

<400> SEQUENCE: 46
actggatggt gggaagatgg a                                                  21

<210> SEQ ID NO 47
<211> LENGTH: 19
```

```
<212> TYPE: DNA
<213> ORGANISM: Artificial Sequence
<220> FEATURE:
<223> OTHER INFORMATION: Oligonucleotide primer sequence
<220> FEATURE:
<221> NAME/KEY: misc_feature
<222> LOCATION: (2)..(2)
<223> OTHER INFORMATION: n = g or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (6)..(6)
<223> OTHER INFORMATION: n = a or c
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (15)..(15)
<223> OTHER INFORMATION: n = c or g

<400> SEQUENCE: 47
angtnnagct ncagnagtc                                              19

<210> SEQ ID NO 48
<211> LENGTH: 19
<212> TYPE: DNA
<213> ORGANISM: Artificial Sequence
<220> FEATURE:
<223> OTHER INFORMATION: Oligonucleotide primer sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (8)..(8)
<223> OTHER INFORMATION: n = a or g
<220> FEATURE:
<221> NAME/KEY: misc_feature
<222> LOCATION: (17)..(17)
<223> OTHER INFORMATION: n = g or a
<220> FEATURE:
<221> NAME/KEY: misc_feature
<222> LOCATION: (18)..(18)
<223> OTHER INFORMATION: n = a or t

<400> SEQUENCE: 48
tnccttgncc ccagtannc                                              19

<210> SEQ ID NO 49
<211> LENGTH: 19
<212> TYPE: DNA
<213> ORGANISM: Artificial Sequence
<220> FEATURE:
<223> OTHER INFORMATION: Oligonucleotide primer sequence

<400> SEQUENCE: 49
tttcgcaacg ggtttgccg                                              19

<210> SEQ ID NO 50
<211> LENGTH: 20
<212> TYPE: DNA
<213> ORGANISM: Artificial Sequence
<220> FEATURE:
<223> OTHER INFORMATION: Oligonucleotide primer sequence

<400> SEQUENCE: 50
```

```
gtttcagagt taagccttcg                                                    20

<210> SEQ ID NO 51
<211> LENGTH: 13
<212> TYPE: DNA
<213> ORGANISM: Human immunoglobulin E light chain (HB134)
<220> FEATURE:
<221> NAME/KEY: misc_feature
<222> LOCATION: (6)..(6)
<223> OTHER INFORMATION: n is a, c, g, or t

<400> SEQUENCE: 51
tacgtngaat aat                                                           13

<210> SEQ ID NO 52
<211> LENGTH: 13
<212> TYPE: DNA
<213> ORGANISM: Human immunoglobulin E light chain (H36)

<400> SEQUENCE: 52
tacgttgaat aat                                                           13

<210> SEQ ID NO 53
<211> LENGTH: 63
<212> TYPE: DNA
<213> ORGANISM: Human immunoglobulin E light chain (HB134)

<400> SEQUENCE: 53
gttggatgtc ctatgaatca agggtttgag ggaagcgcct gacttctgct ggtaccagtg        60
caa                                                                      63

<210> SEQ ID NO 54
<211> LENGTH: 63
<212> TYPE: DNA
<213> ORGANISM: Human immunoglobulin E light chain (H36)

<400> SEQUENCE: 54
gttggatgtc ctatgaatca agggtttggg ggaagcgcct gacttctgct ggtaccagtg        60
caa                                                                      63

<210> SEQ ID NO 55
<211> LENGTH: 63
<212> TYPE: DNA
<213> ORGANISM: Artificial Sequence
<220> FEATURE:
<223> OTHER INFORMATION: Consensus Sequence

<400> SEQUENCE: 55
gttggatgtc ctatgaatca agggtttgrg ggaagcgcct gacttctgct ggtaccagtg        60
caa                                                                      63
```

GENETICALLY ALTERED ANTIBODY-PRODUCING CELL LINES WITH IMPROVED ANTIBODY CHARACTERISTICS

CROSS REFERENCE TO RELATED APPLICATIONS

This claims benefit of U.S. Provisional Application 60/500,071, filed Sep. 3, 2003, which is incorporated herein by reference in its entirety.

TECHNICAL FIELD OF THE INVENTION

The invention is related to the area of antibody maturation and cellular production. In particular, it is related to the field of mutagenesis.

BACKGROUND OF THE INVENTION

The use of antibodies to block the activity of foreign and/or endogenous polypeptides provides an effective and selective strategy for treating the underlying cause of disease. In particular is the use of monoclonal antibodies (MAb) as effective therapeutics such as the FDA approved ReoPro (Glaser, V. (1996) Can ReoPro repolish tarnished monoclonal therapeutics? *Nat. Biotechnol.* 14:1216-1217), an anti-platelet MAb from Centocor; Herceptin (Weiner, L. M. (1999) Monoclonal antibody therapy of cancer. *Semin. Oncol.* 26:43-51), an anti-Her2/neu MAb from Genentech; and Synagis (Saez-Llorens, X. E., et al. (1998) Safety and pharmacokinetics of an intramuscular humanized monoclonal antibody to respiratory syncytial virus in premature infants and infants with bronchopulmonary dysplasia. *Pediat. Infect. Dis. J.* 17:787-791), an anti-respiratory syncytial virus MAb produced by Medimmune.

Standard methods for generating MAbs against candidate protein targets are known by those skilled in the art. Briefly, rodents such as mice or rats are injected with a purified antigen in the presence of adjuvant to generate an immune response (Shield, C. F., et al. (1996) A cost-effective analysis of OKT3 induction therapy in cadaveric kidney transplantation. *Am. J. Kidney Dis.* 27:855-864). Rodents with positive immune sera are sacrificed and splenocytes are isolated. Isolated splenocytes are fused to melanomas to produce immortalized cell lines that are then screened for antibody production. Positive lines are isolated and characterized for antibody production. The direct use of rodent MAbs as human therapeutic agents were confounded by the fact that human anti-rodent antibody (HARA) responses occurred in a significant number of patients treated with the rodent-derived antibody (Khazaeli, M. B., et al., (1994) Human immune response to monoclonal antibodies. *J. Immunother.* 15:42-52). In order to circumvent the problem of HARA, the grafting of the complementarity determining regions (CDRs), which are the critical motifs found within the heavy and light chain variable regions of the immunoglobulin (Ig) subunits making up the antigen-binding domain, onto a human antibody backbone found these chimeric molecules are able to retain their binding activity to antigen while lacking the HARA response (Emery, S.C., and Harris, W. J. "Strategies for humanizing antibodies" In: ANTIBODY ENGINEERING C. A. K. Borrebaeck (Ed.) Oxford University Press, N.Y. 1995. pp. 159-183. A common problem that exists during the "humanization" of rodent-derived MAbs (referred to hereon as HAb) is the loss of binding affinity due to conformational changes in the three-dimensional structure of the CDR domain upon grafting onto the human Ig backbone (U.S. Pat. No. 5,530,101 to Queen et al.). To overcome this problem, additional HAb vectors are usually needed to be engineered by inserting or deleting additional amino acid residues within the framework region and/or within the CDR coding region itself in order to recreate high affinity HAbs (U.S. Pat. No. 5,530,101 to Queen et al.). This process is a very time-consuming procedure that involves the use of expensive computer modeling programs to predict changes that may lead to a high affinity HAb. In some instances the affinity of the HAb is never restored to that of the MAb, rendering them of little therapeutic use.

Another problem that exists in antibody engineering is the generation of stable, high-yielding producer cell lines that is required for manufacturing of the molecule for clinical materials. Several strategies have been adopted in standard practice by those skilled in the art to circumvent this problem. One method is the use of Chinese Hamster Ovary (CHO) cells transfected with exogenous Ig fusion genes containing the grafted human light and heavy chains to produce whole antibodies or single chain antibodies, which are a chimeric molecule containing both light and heavy chains that form an antigen-binding polypeptide (Reff, M. E. (1993) High-level production of recombinant immunoglobulins in mammalian cells. *Curr. Opin. Biotechnol.* 4:573-576). Another method employs the use of human lymphocytes derived from transgenic mice containing a human grafted immune system or transgenic mice containing a human Ig gene repertoire. Yet another method employs the use of monkeys to produce primate MAbs, which have been reported to lack a human anti-monkey response (Neuberger, M., and Gruggermann, M. (1997) Monoclonal antibodies. Mice perform a human repertoire. *Nature* 386:25-26). In all cases, the generation of a cell line that is capable of generating sufficient amounts of high affinity antibody poses a major limitation for producing sufficient materials for clinical studies. Because of these limitations, the utility of other recombinant systems such as plants are currently being explored as systems that will lead to the stable, high-level production of humanized antibodies (Fiedler, U., and Conrad, U. (1995) High-level production and long-term storage of engineered antibodies in transgenic tobacco seeds. *Bio/Technology* 13:1090-1093).

Other factors that naturally contribute to antibody diversity are the phenomena of class switch recombination (CSR) and somatic hypermutation. Class switch recombination is a region-specific recombination at the DNA level that results in the substitution of one immunoglobulin heavy chain region for another. Somatic hypermutation is the name of the phenomenon in which fully assembled immunoglobulin genes nevertheless undergo mutation in the variable regions only. Somatic hypermutation is thought to promote affinity maturation in antibodies.

An enzyme that has been found to play a critical role in both CSR and somatic hypermutation is activation-induced cytidine deaminase ("AID" or "AICDA"). Muramatsu et al. cloned the murine AID (SEQ ID NOs:43 and 44) (Muramatsu et al. (1999) *J. Biol. Chem.* 274(26):18470-18476), while the human AID (SEQ ID NOs:39 and 40) was cloned by Muto et al. (2000) *Genomics* 68:85-88). The mouse and human AID share 92% identity at the amino acid level, both containing 198 amino acids with a conserved cytidine deaminase motif. It is believed that AID acts to induce lesions in the DNA (i.e., deamination of deoxycytidines leading to dU/dG pairs) (Petersen-Mahrt et al. (2002) *Nature* 418:99-104). AID appears to be expressed only in stimulated B cells in germinal centers (Okazaki et al. (2002) *Nature* 416:340-345), and appears to be responsible for both CSR (Petersen et al. (2001) *Nature* 414:660-665) and somatic hypermutation (Yoshikawa et al. (2002) *Science* 296:2033-2036).

Revy et al. showed that human patients with a defect in the AID gene (hyper IgM syndrome, or HIGM2) lacked both CSR and somatic hypermutation activity (Revy et al. (2000) *Cell* 102:565-575). Similarly, spleen cells from AID$^{-/-}$ mice failed to undergo somatic hypermutation or CSR when stimulated in vitro (Muramatsu et al. (2000) *Cell* 102:553-563).

A method for generating diverse antibody sequences within the variable domain that results in HAbs and MAbs with high binding affinities to antigens would be useful for the creation of more potent therapeutic and diagnostic reagents respectively. Moreover, the generation of randomly altered nucleotide and polypeptide residues throughout an entire antibody molecule will result in new reagents that are less antigenic and/or have beneficial pharmacokinetic properties.

SUMMARY OF THE INVENTION

The invention described herein is directed to the use of random genetic mutation throughout an antibody structure in vivo and in vitro by blocking the endogenous mismatch repair (MMR) activity of a host cell and stimulating the activity of AID, producing immunoglobulins that encode biochemically active antibodies. The invention also relates to methods for repeated in vivo and in vitro genetic alterations and selection for antibodies with enhanced binding and pharmacokinetic profiles.

In addition, the ability to develop genetically altered host cells that are capable of secreting increased amounts of antibody will also provide a valuable method for creating cell hosts for product development. The invention described herein is directed to the creation of genetically altered cell hosts with increased antibody production via the blockade of MMR and stimulation of AID.

The invention facilitates the generation of high affinity antibodies and the production of cell lines with elevated levels of antibody production. Other advantages of the present invention are described in the examples and figures described herein.

The invention provides methods for generating genetically altered antibodies (including single chain molecules) and antibody-producing cell hosts in vitro and in vivo, whereby the antibody possesses a desired biochemical property(ies), such as, but not limited to, increased antigen binding, increased gene expression, and/or enhanced extracellular secretion by the cell host. One method for identifying antibodies with increased binding activity or cells with increased antibody production is through the screening of MMR-defective antibody-producing cell clones that produce molecules with enhanced binding properties or clones that have been genetically altered to produce enhanced amounts of antibody product.

The antibody-producing cells suitable for use in the invention include, but are not limited to, rodent, primate, or human hybridomas or lymphoblastoids; mammalian cells transfected and expressing exogenous Ig subunits or chimeric single chain molecules; plant cells, yeast, or bacteria transfected and expressing exogenous Ig subunits or chimeric single chain molecules.

Thus, the invention provides methods for making hypermutable antibody-producing cells by introducing a polynucleotide comprising a dominant negative allele of a mismatch repair gene into cells that are capable of producing antibodies. The cells that are capable of producing antibodies include cells that naturally produce antibodies, and cells that are engineered to produce antibodies through the introduction of immunoglobulin encoding sequences. Conveniently, the introduction of polynucleotide sequences into cells is accomplished by transfection.

The invention also provides methods for producing hybridoma cells producing high-affinity antibodies from in vitro immunized immunoglobulin-producing cells comprising: (a) combining peripheral blood cells comprising immunoglobulin-producing cells with an immunogenic antigen in vitro; (b) fusing the immunoglobulin-producing cells with myeloma cells to form parental hybridoma cells, wherein the hybridoma cells express a dominant negative allele of a mismatch repair gene; (c) performing a screen for expression of activation-induced cytidine deaminase; (d) incubating the hybridoma cells to allow for mutagenesis, thereby forming hypermutated hybridoma cells. The cells may be further screened for cells that produce antibody that specifically binds the immunizing antigen. The selected cells may also be manipulated to inactivate the dominant negative allele of the mismatch repair gene to restabilize the genome of the cell. The selected cells may also be manipulated to inactivate the expression of AID.

In certain emboiments of the in vitro immunization method, the immunoglobulin-producing cell and/or the myeloma cell is naturally deficient in mismatch repair such that, upon fusion, the resulting hybridoma cell is naturally deficient in mismatch repair. In such a case, when restabilizing the genome, the cells must be manipulated to genetically complement the deficiency by any method known in the art. For example, but not by way of limitation, if the MMR deficiency is due to loss of an essential gene for mismatch repair, the gene may be reintroduced into the cell operably linked to expression control sequences such that the normal MMR gene is replaced and MMR activity is restored. The expression of the MMR gene may be under the control of a constituitive or an inducible promoter. In other cases in which the MMR defect is the expression of a dominant negative allele of the MMR gene, the genome may be complemented by inactivation of the MMR gene. For example, but not by way of limitation, the defective MMR allele may be knocked out in whole or in part by any means known to the skilled artisan, such that the allele no longer asserts a dominant negative effect on mismatch repair.

In other embodiments of the in vitro immunization method, the hybridoma cells are manipulated to be MMR deficient. In certain embodiments, a dominant negative allele of a mismatch repair gene is introduced into the antibody-producing cell. In other embodiments, the dominant negative allele of a mismatch repair gene is introduced into the myeloma cell. In other embodiments, the dominant negative allele of a mismatch repair gene is introduced into the hybridoma cell. The introduction of the dominant negative allele of a mismatch repair gene may be by any means known in the art such as, but not limited to, transfection.

The invention also provides methods for producing hybridoma cells producing high-affinity antibodies from in vitro immunized immunoglobulin-producing cells comprising: (a) combining peripheral blood cells comprising immunoglobulin-producing cells with an immunogenic antigen in vitro; (b) fusing the immunoglobulin-producing cells with myeloma cells to form parental hybridoma cells; (c) performing a screen for expression of activation-induced cytidine deaminase; (d) incubating the hybridoma cells to allow for mutagenesis, thereby forming hypermutated hybridoma cells. The cells may be further screened for cells that produce antibody that specifically binds the immunizing antigen. The selected cells may also be manipulated to inactivate the expression of AID.

The invention also provides methods for producing hybridoma cells producing high affinity antibodies from in vitro immunized immunoglobulin-producing cells comprising: (a) combining peripheral blood cells comprising immunoglobulin-producing cells with an immunogenic antigen in vitro; (b) fusing the immunoglobulin-producing cells with myeloma cells to form parental hybridoma cells, wherein the hybridoma cells express a dominant negative allele of a mismatch repair gene; (c) inducing expression of activation-induced cytidine deaminase; (d) incubating the hybridoma cells to allow for mutagenesis, thereby forming hypermutated hybridoma cells. The cells may be further screened for cells that produce antibody that specifically binds the immunizing antigen. The selected cells may also be manipulated to inactivate the dominant negative allele of the mismatch repair gene to restabilize the genome of the cell. The selected cells may also be manipulated to inactivate the expression of AID.

In some embodiments the AID gene is introduced into the antibody-producing cell, myeloma cell or hybridoma cell operably linked to expression control sequences such that AID is expressed in the cells. In certain embodiments, AID is operably linked to an inducible promoter. In some embodiments, once cells are selected for the desired phenotype, AID expression is turned off, by any means known in the art such as by inactivation of the AID by partially or completely knocking out the gene, by withdrawing the inducer of the inducible promoter, and the like. In some embodiments, the antibody-producing cells, myeloma cells, and/or hybridoma cells may be further manipulated to be defective in mismatch repair. In some embodiments, this is accomplished by introducing into the cell a dominant negative allele of a mismatch repair gene. In other embodiments, this is accomplished by incubating the cell in a chemical inhibitor of mismatch repair as described in WO 02/054856 (Nicolaides et al., filed Jan. 15, 2001). To restabilize the genome of the cell, the dominant negative allele may be inactivated, or, in the case of chemical inhibition of MMR, the chemical inhibitor may be withdrawn or diluted out, for example.

The invention also provides methods of making hypermutable antibody-producing cells by introducing a dominant negative mismatch repair (MMR) gene such as PMS2 (preferably human PMS2), MLH1, PMS1, MSH2, or MSH2 into cells that are capable of producing antibodies. The dominant negative allele of a mismatch repair gene may be a truncation mutation of a mismatch repair gene (preferably a truncation mutation at codon 134, or a thymidine at nucleotide 424 of wild-type PMS2). The invention also provides methods in which mismatch repair gene activity is suppressed. This may be accomplished, for example, using antisense molecules directed against the mismatch repair gene or transcripts.

Other embodiments of the invention provide methods for making a hypermutable antibody-producing cell by introducing a polynucleotide comprising a dominant negative allele of a mismatch repair gene into a fertilized egg of an animal. These methods may also include subsequently implanting the eggs into pseudo-pregnant females whereby the fertilized eggs develop into a mature transgenic animal. The mismatch repair genes may include, for example, PMS2 (preferably human PMS2), MLH1, PMS1, MSH2, or MSH2. The dominant negative allele of a mismatch repair gene may be a truncation mutation of a mismatch repair gene (preferably a truncation mutation at codon 134, or a thymidine at nucleotide 424 of wild-type PMS2).

The invention further provides homogeneous compositions of cultured, hypermutable, mammalian cells that are capable of producing antibodies and contain a dominant negative allele of a mismatch repair gene. The mismatch repair genes may include, for example, PMS2 (preferably human PMS2), MLH1, PMS1, MSH2, or MSH2. The dominant negative allele of a mismatch repair gene may be a truncation mutation of a mismatch repair gene (preferably a truncation mutation at codon 134, or a thymidine at nucleotide 424 of wild-type PMS2). The cells of the culture may contain PMS2, (preferably human PMS2), MLH1, or PMS1; or express a human mutL homolog, or the first 133 amino acids of hPMS2.

The invention further provides methods for generating a mutation in an immunoglobulin gene of interest by culturing an immunoglobulin-producing cell selected for an immunoglobulin of interest wherein the cell contains a dominant negative allele of a mismatch repair gene. The properties of the immunoglobulin produced from the cells can be assayed to ascertain whether the immunoglobulin gene harbors a mutation. The assay may be directed to analyzing a polynucleotide encoding the immunoglobulin, or may be directed to the immunoglobulin polypeptide itself.

The invention also provides methods for generating a mutation in a gene affecting antibody production in an antibody-producing cell by culturing the cell expressing a dominant negative allele of a mismatch repair gene, and testing the cell to determine whether the cell harbors mutations within the gene of interest, such that a new biochemical feature (e.g., over-expression and/or secretion of immunoglobulin products) is generated. The testing may include analysis of the steady state expression of the immunoglobulin gene of interest, and/or analysis of the amount of secreted protein encoded by the immunoglobulin gene of interest. The invention also embraces prokaryotic and eukaryotic transgenic cells made by this process, including cells from rodents, non-human primates, and humans.

Other aspects of the invention encompass methods of reversibly altering the hypermutability of an antibody-producing cell, in which an inducible vector containing a dominant negative allele of a mismatch repair gene operably linked to an inducible promoter is introduced into an antibody-producing cell. The cell is treated with an inducing agent to express the dominant negative mismatch repair gene (which can be PMS2 (preferably human PMS2), MLH1, or PMS1). Alternatively, the cell may be induced to express a human mutL homolog or the first 133 amino acids of hPMS2. In another embodiment, the cells may be rendered capable of producing antibodies by co-transfecting a preselected immunoglobulin gene of interest. The immunoglobulin genes of the hypermutable cells, or the proteins produced by these methods may be analyzed for desired properties, and induction may be stopped such that the genetic stability of the host cell is restored.

The invention also embraces methods of producing genetically altered antibodies by transfecting a polynucleotide encoding an immunoglobulin protein into a cell containing a dominant negative mismatch repair gene (either naturally or in which the dominant negative mismatch repair gene was introduced into the cell), culturing the cell to allow the immunoglobulin gene to become mutated and produce a mutant immunoglobulin, screening for a desirable property of the mutant immunoglobulin protein, isolating the polynucleotide molecule encoding the selected mutant immunoglobulin possessing the desired property, and transfecting said mutant polynucleotide into a genetically stable cell, such that the mutant antibody is consistently produced without further genetic alteration. The dominant negative mismatch repair gene may be PMS2 (preferably human PMS2), MLH1, or PMS1. Alternatively, the cell may express a human mutL homolog or the first 133 amino acids of hPMS2.

The invention further provides methods for generating genetically altered cell lines that express enhanced amounts of an antigen-binding polypeptide. These antigen-binding polypeptides may be, for example, immunoglobulins. The methods of the invention also include methods for generating genetically altered cell lines that secrete enhanced amounts of an antigen-binding polypeptide. The cell lines are rendered hypermutable by dominant negative mismatch repair genes that provide an enhanced rate of genetic hypermutation in a cell producing antigen-binding polypeptides such as antibodies. Such cells include, but are not limited to, hybridomas. Expression of enhanced amounts of antigen-binding polypeptides may be through enhanced transcription or translation of the polynucleotides encoding the antigen-binding polypeptides, or through the enhanced secretion of the antigen-binding polypeptides, for example.

Methods are also provided for creating genetically altered antibodies in vivo by blocking the MMR activity of the cell host, or by transfecting genes encoding for immunoglobulin in a MMR-defective cell host.

Antibodies with increased binding properties to an antigen due to genetic changes within the variable domain are provided in methods of the invention that block endogenous MMR of the cell host. Antibodies with increased binding properties to an antigen due to genetic changes within the CDR regions within the light and/or heavy chains are also provided in methods of the invention that block endogenous MMR of the cell host.

The invention provides methods of creating genetically altered antibodies in MMR defective Ab-producer cell lines with enhanced pharmacokinetic properties in host organisms including but not limited to rodents, primates, and man.

These and other aspects of the invention are provided by one or more of the embodiments described below. In one embodiment of the invention, a method for making an antibody-producing cell line hypermutable is provided. A polynucleotide encoding a dominant negative allele of a MMR gene is introduced into an antibody-producing cell. The cell becomes hypermutable as a result of the introduction of the gene.

In another embodiment of the invention, a method is provided for introducing a mutation into an endogenous gene encoding for an immunoglobulin polypeptide or a single chain antibody. A polynucleotide encoding a dominant negative allele of a MMR gene is introduced into a cell. The cell becomes hypermutable as a result of the introduction and expression of the MMR gene allele. The cell further comprises an immunoglobulin gene of interest. The cell is grown and tested to determine whether the gene encoding for an immunoglobulin or a single chain antibody of interest harbors a mutation. In another aspect of the invention, the gene encoding the mutated immunoglobulin polypeptide or single chain antibody may be isolated and expressed in a genetically stable cell. In a preferred embodiment, the mutated antibody is screened for at least one desirable property such as, but not limited to, enhanced binding characteristics.

In another embodiment of the invention, a gene or set of genes encoding for Ig light and heavy chains or a combination thereof are introduced into a mammalian cell host that is MMR-defective. The cell is grown, and clones are analyzed for antibodies with enhanced binding characteristics.

In another embodiment of the invention, methods are provided for producing new phenotypes of a cell. A polynucleotide encoding a dominant negative allele of a MMR gene is introduced into a cell. The cell becomes hypermutable as a result of the introduction of the gene. The cell is grown and tested for the expression of new phenotypes, such as enhanced secretion of a polypeptide.

These and other embodiments of the invention provide the art with methods that can generate enhanced mutability in cells and animals as well as providing cells and animals harboring potentially useful mutations for the large-scale production of high affinity antibodies with beneficial pharmacokinetic profiles.

DETAILED DESCRIPTION OF THE INVENTION

Figure 1:
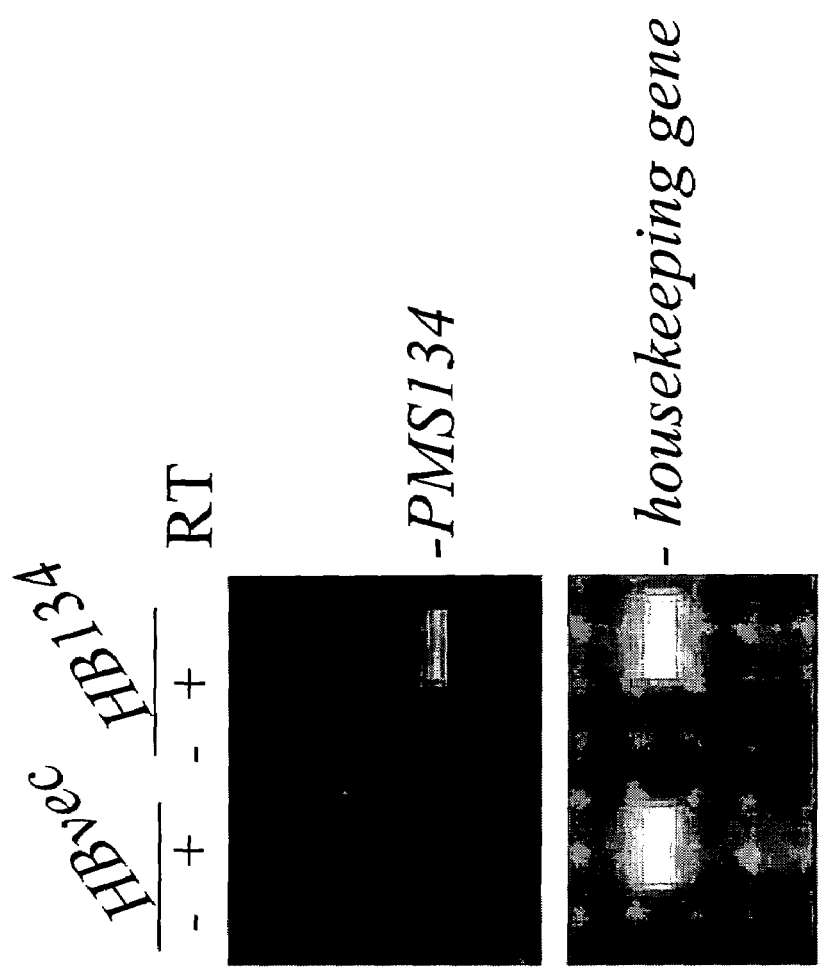
FIG. 1 illustrates hybridoma cells stably expressing PMS2 and PMS134 MMR genes. Shown is steady state mRNA expression of MMR genes transfected into a murine hybridoma cell line. Stable expression was found after 3 months of continuous growth. The (−) lanes represent negative controls where no reverse transcriptase was added, and the (+) lanes represent samples reverse-transcribed and PCR-amplified for the MMR genes and an internal housekeeping gene as a control.

The reference works, patents, patent applications, and scientific literature, including accession numbers to GenBank database sequences that are referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Standard reference works setting forth the general principles of recombinant DNA technology known to those of skill in the art include Ausubel et al. CURRENT PROTOCOLS IN MOLECULAR BIOLOGY, John Wiley & Sons, New York (1998); Sambrook et al. MOLECULAR CLONING: A LABORATORY MANUAL, 2D ED., Cold Spring Harbor Laboratory Press, Plainview, N.Y. (1989); Kaufman et al., Eds., HANDBOOK OF MOLECULAR AND CELLULAR METHODS IN BIOLOGY AND MEDICINE, CRC Press, Boca Raton (1995); McPherson, Ed., DIRECTED MUTAGENESIS: A PRACTICAL APPROACH, IRL Press, Oxford (1991).

As used herein "activating cytokine" means a soluble molecule that stimulates cells to express a new protein, differentiate or proliferate.

As used herein, the term "epitope" refers to the portion of an antigen to which a monoclonal antibody specifically binds.

As used herein, the term "conformational epitope" refers to a discontinuous epitope formed by a spatial relationship between amino acids of an antigen other than an unbroken series of amino acids.

As used herein, the term "isoform" refers to a specific form of a given polypeptide.

As used herein, the term "immunobased" refers to protein-based therapies to generate immunological responses that can specifically or preferentially kill target bearing cells.

The term "preventing" refers to decreasing the probability that an organism contracts or develops an abnormal condition.

The term "treating" refers to having a therapeutic effect and at least partially alleviating or abrogating an abnormal condition in the organism.

The term "therapeutic effect" refers to the inhibition of an abnormal condition. A therapeutic effect relieves to some extent one or more of the symptoms of the abnormal condition. In reference to the treatment of abnormal conditions, a therapeutic effect can refer to one or more of the following: (a) an increase or decrease in the proliferation, growth, and/or differentiation of cells; (b) inhibition (i.e., slowing or stopping) of growth of tumor cells in vivo (c) promotion of cell death; (d) inhibition of degeneration; (e) relieving to some extent one or more of the symptoms associated with the abnormal condition; and (f) enhancing the function of a population of cells. The monoclonal antibodies and derivatives thereof described herein effectuate the therapeutic effect alone or in combination with conjugates or additional components of the compositions of the invention.

As used herein, the term "about" refers to an approximation of a stated value within an acceptable range. Preferably the range is +/−5% of the stated value.

As used herein "dominant negative effect" refers to the ability of an allele of a mismatch repair gene to inhibit normal mismatch repair in cells, which may be assessed by the cells exhibiting microsatellite instability.

Stimulation of expression includes any means of increasing the expression of a nucleic acid sequence or a peptide and includes but is not limited to stimulation of endogenous expression; inducible expression; inserting a constitutively active promoter, etc.

As used herein, "mitogenic polypeptide" refers to a polypeptide that may be conjugated to an immunogen to enhance stimulation of the immune system to the antigen.

As used herein "cells capable of producing antibodies" refers to cells that are naturally capable of producing immunoglobulins. Sources for such cells are, for example, lymph node cells, spleen cells, peripheral blood cells, and antibody-producing cell lines.

Methods have been discovered for developing hypermutable antibody-producing cells by taking advantage of the conserved mismatch repair (MMR) process of host cells. Dominant negative alleles of such genes, when introduced into cells or transgenic animals, increase the rate of spontaneous mutations by reducing the effectiveness of DNA repair and thereby render the cells or animals hypermutable. Hypermutable cells or animals can then be utilized to develop new mutations in a gene of interest. Blocking MMR in antibody-producing cells (such as but not limited to: hybridomas; mammalian cells transfected with genes encoding for Ig light and heavy chains; mammalian cells transfected with genes encoding for single chain antibodies; eukaryotic cells transfected with Ig genes) can enhance the rate of mutation within these cells leading to clones that have enhanced antibody production and/or cells containing genetically altered antibodies with enhanced biochemical properties such as increased antigen binding. The process of MMR, also called mismatch proofreading, is carried out by protein complexes in cells ranging from bacteria to mammalian cells. A MMR gene is a gene that encodes for one of the proteins of such a mismatch repair complex. Although not wanting to be bound by any particular theory of mechanism of action, a MMR complex is believed to detect distortions of the DNA helix resulting from non-complementary pairing of nucleotide bases. The non-complementary base on the newer DNA strand is excised, and the excised base is replaced with the appropriate base, which is complementary to the older DNA strand. In this way, cells eliminate many mutations that occur as a result of mistakes in DNA replication.

Dominant negative alleles cause a MMR defective phenotype even in the presence of a wild-type allele in the same cell. An example of a dominant negative allele of a MMR gene is the human gene hPMS2-134, which carries a truncating mutation at codon 134 (SEQ ID NO:5). The mutation causes the product of this gene to abnormally terminate at the position of the 134th amino acid, resulting in a shortened polypeptide containing the N-terminal 133 amino acids. Such a mutation causes an increase in the rate of mutations, which accumulate in cells after DNA replication. Expression of a dominant negative allele of a mismatch repair gene results in impairment of mismatch repair activity, even in the presence of the wild-type allele. Any allele which produces such effect can be used in this invention. Dominant negative alleles of a MMR gene can be obtained from the cells of humans, animals, yeast, bacteria, or other organisms. Such alleles can be identified by screening cells for defective MMR activity. Cells from animals or humans with cancer can be screened for defective mismatch repair. Cells from colon cancer patients may be particularly useful. Genomic DNA, cDNA, or mRNA from any cell encoding a MMR protein can be analyzed for variations from the wild type sequence. Dominant negative alleles of a MMR gene can also be created artificially, for example, by producing variants of the hPMS2-134 allele or other MMR genes. Various techniques of site-directed mutagenesis can be used. The suitability of such alleles, whether natural or artificial, for use in generating hypermutable cells or animals can be evaluated by testing the mismatch repair activity caused by the allele in the presence of one or more wild-type alleles, to determine if it is a dominant negative allele.

A cell or an animal into which a dominant negative allele of a mismatch repair gene has been introduced will become hypermutable. This means that the spontaneous mutation rate of such cells or animals is elevated compared to cells or animals without such alleles. The degree of elevation of the spontaneous mutation rate can be at least 2-fold, 5-fold, 10-fold, 20-fold, 50-fold, 100-fold, 200-fold, 500-fold, or 1000-fold that of the normal cell or animal. The use of chemical mutagens such as but limited to methane sulfonate, dimethyl sulfonate, O6-methyl benzadine, MNU, ENU, etc. can be used in MMR defective cells to increase the rates an additional 10 to 100 fold that of the MMR deficiency itself.

According to one aspect of the invention, a polynucleotide encoding for a dominant negative form of a MMR protein is introduced into a cell. The gene can be any dominant negative allele encoding a protein, which is part of a MMR complex, for example, PMS2, PMS1, MLH1, or MSH2. The dominant negative allele can be naturally occurring or made in the laboratory. The polynucleotide can be in the form of genomic DNA, cDNA, RNA, or a chemically synthesized polynucleotide.

The polynucleotide can be cloned into an expression vector containing a constitutively active promoter segment (such as but not limited to CMV, SV40, Elongation Factor or LTR sequences) or to inducible promoter sequences such as the steroid inducible pIND vector (Invitrogen), where the expression of the dominant negative MMR gene can be regulated. The polynucleotide can be introduced into the cell by transfection.

According to another aspect of the invention, an immunoglobulin (Ig) gene, a set of Ig genes or a chimeric gene containing whole or parts of an Ig gene can be transfected into MMR deficient cell hosts, the cell is grown and screened for clones containing genetically altered Ig genes with new biochemical features. MMR defective cells may be of human, primates, mammals, rodent, plant, yeast or of the prokaryotic kingdom. The mutated gene encoding the Ig with new biochemical features may be isolated from the respective clones and introduced into genetically stable cells (i.e., cells with normal MMR) to provide clones that consistently produce Ig with the new biochemical features. The method of isolating the Ig gene encoding Ig with new biochemical features may be any method known in the art. Introduction of the isolated polynucleotide encoding the Ig with new biochemical features may also be performed using any method known in the art, including, but not limited to transfection of an expression vector containing the polynucleotide encoding the Ig with new biochemical features. As an alternative to transfecting an Ig gene, a set of Ig genes or a chimeric gene containing whole or parts of an Ig gene into an MMR-deficient host cell, such Ig genes may be transfected simultaneously with a gene encoding a dominant negative mismatch repair gene into a genetically stable cell to render the cell hypermutable.

Transfection is any process whereby a polynucleotide is introduced into a cell. The process of transfection can be carried out in a living animal, e.g., using a vector for gene therapy, or it can be carried out in vitro, e.g., using a suspension of one or more isolated cells in culture. The cell can be any type of eukaryotic cell, including, for example, cells isolated from humans or other primates, mammals or other vertebrates, invertebrates, and single-celled organisms such as protozoa, yeast, or bacteria.

In general, transfection will be carried out using a suspension of cells, or a single cell, but other methods can also be applied as long as a sufficient fraction of the treated cells or tissue incorporates the polynucleotide so as to allow transfected cells to be grown and utilized. The protein product of the polynucleotide may be transiently or stably expressed in the cell. Techniques for transfection are well known. Available techniques for introducing polynucleotides include but are not limited to electroporation, transduction, cell fusion, the use of calcium chloride, and packaging of the polynucleotide together with lipid for fusion with the cells of interest. Once a cell has been transfected with the MMR gene, the cell can be grown and reproduced in culture. If the transfection is stable, such that the gene is expressed at a consistent level for many cell generations, then a cell line results.

An isolated cell is a cell obtained from a tissue of humans or animals by mechanically separating out individual cells and transferring them to a suitable cell culture medium, either with or without pretreatment of the tissue with enzymes, e.g., collagenase or trypsin. Such isolated cells are typically cultured in the absence of other types of cells. Cells selected for the introduction of a dominant negative allele of a mismatch repair gene may be derived from a eukaryotic organism in the form of a primary cell culture or an immortalized cell line, or may be derived from suspensions of single-celled organisms.

A polynucleotide encoding for a dominant negative form of a MMR protein can be introduced into the genome of an animal by producing a transgenic animal. The animal can be any species for which suitable techniques are available to produce transgenic animals. For example, transgenic animals can be prepared from domestic livestock, e.g., bovine, swine, sheep, goats, horses, etc.; from animals used for the production of recombinant proteins, e.g., bovine, swine, or goats that express a recombinant polypeptide in their milk; or experimental animals for research or product testing, e.g., mice, rats, guinea pigs, hamsters, rabbits, etc. Cell lines that are determined to be MMR-defective can then be used as a source for producing genetically altered immunoglobulin genes in vitro by introducing whole, intact immunoglobulin genes and/or chimeric genes encoding for single chain antibodies into MMR-defective cells from any tissue of the MMR-defective animal.

Once a transfected cell line or a colony of transgenic animals has been produced, it can be used to generate new mutations in one or more gene(s) of interest. A gene of interest can be any gene naturally possessed by the cell line or transgenic animal or introduced into the cell line or transgenic animal. An advantage of using such cells or animals to induce mutations is that the cell or animal need not be exposed to mutagenic chemicals or radiation, which may have secondary harmful effects, both on the object of the exposure and on the workers. However, chemical mutagens may be used in combination with MMR deficiency, which renders such mutagens less toxic due to an undetermined mechanism. Hypermutable animals can then be bred and selected for those producing genetically variable B-cells that may be isolated and cloned to identify new cell lines that are useful for producing genetically variable cells. Once a new trait is identified, the dominant negative MMR gene allele can be removed by directly knocking out the allele by technologies used by those skilled in the art or by breeding to mates lacking the dominant negative allele to select for offspring with a desired trait and a stable genome. Another alternative is to use a CRE-LOX expression system, whereby the dominant negative allele is spliced from the animal genome once an animal containing a genetically diverse immunoglobulin profile has been established. Yet another alternative is the use of inducible vectors such as the steroid induced pIND (Invitrogen) or pMAM (Clonetech) vectors which express exogenous genes in the presence of corticosteroids.

Mutations can be detected by analyzing for alterations in the genotype of the cells or animals, for example by examining the sequence of genomic DNA, cDNA, messenger RNA, or amino acids associated with the gene of interest. Mutations can also be detected by screening for the production of antibody titers. A mutant polypeptide can be detected by identifying alterations in electrophoretic mobility, spectroscopic properties, or other physical or structural characteristics of a protein encoded by a mutant gene. One can also screen for altered function of the protein in situ, in isolated form, or in model systems. One can screen for alteration of any property of the cell or animal associated with the function of the gene of interest, such as but not limited to Ig secretion.

Examples of nucleic acid sequences encoding mismatch repair proteins useful in the method of the invention include, but are not limited to the following: PMS1 (SEQ ID NO:1); PMS2 (SEQ ID NO:3); PMS2-134 (SEQ ID NO:5); PMSR2 (SEQ ID NO:7); PMSR3 (SEQ ID NO:9); MLH1 (SEQ ID NO:11); MLH3 (SEQ ID NO:13); MSH2 (SEQ ID NO:15); MSH3 (SEQ ID NO:17); MSH4 (SEQ ID NO:19); MSH5 (SEQ ID NO:21); MSH6 (SEQ ID NO:23); PMSR6 (SEQ ID NO:25); PMSL9 (SEQ ID NO:27); yeast MLH1 (SEQ ID NO:29); mouse PMS2 (SEQ ID NO:31); mouse PMS2-134 (SEQ ID NO:33); *Arabidopsis thaliana* PMS2 (SEQ ID NO:35); and *Arabidopsis thaliana* PMS2-134 (SEQ ID NO:37). The corresponding amino acid sequences for the listed nucleic acid sequences are: PMS1 (SEQ ID NO:2); PMS2 (SEQ ID NO:4); PMS2-134 (SEQ ID NO:6); PMSR2 (SEQ ID NO:8); PMSR3 (SEQ ID NO:10); MLH1 (SEQ ID NO:12); MLH3 (SEQ ID NO:14); MSH2 (SEQ ID NO:16); MSH3 (SEQ ID NO:18); MSH4 (SEQ ID NO:20); MSH5 (SEQ ID NO:22); MSH6 (SEQ ID NO:24); PMSR6 (SEQ ID NO:26); PMSL9 (SEQ ID NO:28); yeast MLH1 (SEQ ID NO:30); mouse PMS2 (SEQ ID NO:32); mouse PMS2-134 (SEQ ID NO:34); *Arabidopsis thaliana* PMS2 (SEQ ID NO:36); and *Arabidopsis thaliana* PMS2-134 (SEQ ID NO:38).

The invention also embraces in vitro immunization of cells that are capable of producing antibodies such that the cells produce antigen-specific antibodies. The cells that are capable of producing antibodies are cells derived from sources containing lymphocytes such as the peripheral blood, lymph nodes and spleen. Immunogens may include purified antigens, denatured protein, solubilized cells, protein mixtures, membrane preparations, whole cells, minced tissues and tumors, organisms, viruses, and the like. In the methods of the invention, the immunogens may be conjugated with a mitogenic polypeptide, including, but not limited to at least a portion of tetanus toxoid, ovalbumin, bovine serum albumin, thyroglobulin, diptheria toxoid, BCG, keyhole limpet hemocyanin (KLH), and cholera toxin.

Antigens may be conjugated to mitogenic polypeptides in any way known in the art. For example, fusion proteins may be generated by expressing a polypeptide in a recombinant expression system comprising the polynucleotide encoding at least a portion of the antigen joined in-frame to a polynucleotide encoding at least a portion of the mitogenic polypeptide. The fusion protein may have the mitogenic polypeptide joined at either the amino- or carboxy-terminus of the antigen. In some embodiments, more that one antigen may be expressed as a fusion protein in combination with a mitogenic polypeptide. In other embodiments, more that one mitogenic polypeptide may be expressed as a fusion protein with the antigen or antigens. In other embodiments, more than one mitogenic polypeptide and more than one antigen may be expressed together as a single fusion protein.

In an alternative embodiment, at least a portion of the mitogenic polypeptide is conjugated to at least a portion of the antigen using chemical cross-linkers. Examples of chemical cross-linkers include, but are not limited to gluteraldehyde, formaldehyde, 1,1-bis (diazoacetyl)-2-phenylethane, N-hydroxysuccinimide esters (e.g., esters with 4-azidosalicylic acid, homobifunctional imidoesters including disuccinimidyl esters such as 3,3'-dithiobis (succinimidyl-propionate), and bifunctional maleimides such as bis-N-maleimido-1,8-octane). Derivatizing agents such as methyl-3-[(p-azido-phenyl)dithio]propioimidate yield photoactivatable intermediates which are capable of forming cross-links in the presence of light. Alternatively, for example, a lysine residue in the mitogenic polypeptide or antigen may be coupled to a C-terminal or other cysteine residue in the antigen or mitogenic polypeptide, respectively, by treatment with N-γ-maleimidobutyryloxy-succinimide (Kitagawa and Aikawa (1976) *J. Biochem.* 79, 233-236).

Alternatively, a lysine residue in the mitogenic polypeptide or antigen may be conjugated to a glutamic or aspartic acid residue in the antigen or mitogenic polypeptide, respectively, using isobutylchloroformate (Thorell and De Larson (1978) RADIOIMMUNOASSAY AND RELATED TECHNIQUES: METHODOLOGY AND CLINICAL APPLICATIONS, p. 288). Other coupling reactions and reagents have been described in the literature The conditions for the in vitro immunization procedure comprise incubating the cells at about 25-37° C., (preferably 37° C.) supplied with about 5-10% $CO_2$, in some embodiments, the incubation is performed with between about 6-9% $CO_2$, in other embodiments the incubation is performed in about 8% $CO_2$. The cell density is between about 2.5 to $5\times10^6$ cells/ml in culture medium. In some embodiments, the culture medium is supplemented with about 2-20% FBS. In other embodiments, the culture medium is supplemented with about 5-15% FBS. In other embodiments, the culture medium is supplemented with about 7-12% FBS. In other embodiments, the culture medium is supplemented with about 10% FBS.

The in vitro stimulation culture medium is supplemented with cytokines to stimulate the cells and increase the immune response. In general IL-2 is supplied in the culture medium. However, other cytokines and additives may also be included to increase the immune response. Such cytokines and factors may include, for example, IL-4 and anti-CD40 antibodies.

The immunogen-stimulated cells are fused to immortalized cells to create hybridoma cells. Typically, the immortalized cell is a myeloma cell. The fusion of myeloma cells with the immunoglobulin-producing cells may be by any method known in the art for the creation of hybridoma cells. These methods include, but are not limited to, the hybridoma technique of Kohler and Milstein, (1975, *Nature* 256:495-497; and U.S. Pat. No. 4,376,110) (see also, Brown et al. (1981) *J. Immunol.* 127:539-546; Brown et al. (1980) *J. Biol. Chem.* 255 (11):4980-4983; Yeh et al. (1976) *Proc. Natl. Acad. Sci. USA* 76:2927-2931; and Yeh et al. (1982) *Int. J. Cancer* 29:269-275), the human B-cell hybridoma technique (Kosbor et al., 1983, *Immunology Today* 4:72; Cole et al., 1983, *Proc. Natl. Acad. Sci. USA* 80:2026-2030), and the EBV-hybridoma technique (Cole et al., 1985, Monoclonal Antibodies and Cancer Therapy, Alan R. Liss, Inc., pp. 77-96). The hybridoma-producing the MAb of this invention may be cultivated in vitro or in vivo.

The technology for producing monoclonal antibody hybridomas is well-known to those of skill in the art and is described, for example in Kenneth, in Monoclonal Antibodies: A New Dimension In Biological Analyses, Plenum Publishing Corp., New York, N.Y. (1980); Lerner (1981) *Yale J. Biol. Med.,* 54:387-402; Galfre et al. (1977) *Nature* 266: 55052; and Gefter et al. (1977) *Somatic Cell Genet.* 3:231-236. However, many variations of such methods are possible and would be appreciated by one of skill in the art. Thus, the techniques for generation of hybridomas is not limited to the disclosures of these references.

Any myeloma cell may be used in the method of the invention. Preferably, the myeloma cells are human cells, but the invention is not limited thereto or thereby. In some embodiments, the cells are sensitive to medium containing hypoxanthine, aminopterin, and thymidine (HAT medium). In some embodiments, the myeloma cells do not express immunoglobulin genes. In some embodiments the myeloma cells are negative for Epstein-Barr virus (EBV) infection. In preferred embodiments, the myeloma cells are HAT-sensitive, EBV negative and Ig expression negative. Any suitable myeloma may be used. An example of such a myeloma is that described in U.S. Pat. No. 4,720,459 to Winkelhake, and deposited with the American Type Culture Collection (ATCC) as CRL 8644. Murine hybridomas may be generated using mouse myeloma cell lines (e.g., the P3-NS 1/1-Ag4-1, P3-x63-Ag8.653 or Sp2/O-Ag14 myeloma lines). These murine myeloma lines are available from the ATCC.

The in vitro immunization procedure involves incubating the cells which are capable of producing antibodies with an immunogen under conditions that promotes stimulation of the cells capable of producing antibodies. In some embodiments, the cells may be incubated in L-leucyl-L-lysine methyl ester hydrobromide (LLOMe). While not wishing to be bound by any particular theory of operation, LLOme is believed to lysosomotropic and specifically kills cytotoxic cells in the cell pool (such as NK cells, cytotoxic T cells, and CD8+ suppressor T cells) while not having an effect on B cells, T helper cells accessory cells and fibroblasts (Borrebaeck (1988) *Immunol. Today* 9(11):355-359). Generally, the cells may be incubated with LLOMe for a period of 1-30 minutes. In some embodiments, the incubation is performed for 10-20 minutes. In other embodiments, the incubation is performed for 15 minutes. The LLOMe is generally a component of culture medium, such as, for example, RPMI 1640, and is provided in a concentration of about 0.10 to 1 mM. In some embodiments, LLOMe is provided in an amount of about 0.10 to 0.50 mM. In other embodiments, LLOMe is provided in an amount of about 0.25 mM.

In some embodiments of the method of the invention, the hybridoma cells may be rendered hypermutable by the introduction of a dominant negative allele of a mismatch repair gene. The dominant negative allele of the mismatch repair gene may be introduced into the hybridoma cell (i.e., after the fusion of immunoglobulin-producing cells with the myeloma cells) or may be introduced into the myeloma cell prior to the fusions.

The dominant negative allele of the mismatch repair gene is in the form of a polynucleotide which may be in the form of genomic DNA, cDNA, RNA, or a chemically synthesized polynucleotide. The polynucleotide can be cloned into an expression vector containing a constitutively active promoter segment (such as, but not limited to, CMV, SV40, EF-1 D or LTR sequences) or to inducible promoter sequences such as those from tetracycline, or ecdysone/glucocorticoid inducible vectors, where the expression of the dominant negative mismatch repair gene can be regulated. The polynucleotide can be introduced into the cell by transfection.

The hybridoma cells are screened for antibodies that specifically bind the antigen used in the immunization procedure. In one embodiment, the cells are also screened for clones that express AID. These clones are expected to have a higher rate of somatic hypermutation and class switch recombination. These clones are selected and isolated to generate antibodies that specifically bind antigen and which perform CSR and somatic hypermutation. Once a desired phenotype is achieved, one may also inactivate AID by any means known in the art, including but not limited to knocking out all or part of the AID gene, by introducing a frameshift in the AID gene, by interrupting the AID gene with another sequence by homologous recombination, and the like.

In other embodiments of the invention, the hybridoma cells are induced to express AID by stimulating the hybridoma cells with activating cytokines. The activating cytokines may be lipopolysaccharide (LPS), TGFβ, CD40L, IL-4 and combinations thereof.

In other embodiments of the invention, the hybridoma cells are induced to express AID by transfecting the hybridoma cells with polynucleotides comprising a sequence encoding AID operably linked to expression control sequences. The hybridoma cells may constituitively express AID or be induced to express AID. Once a desired phenotype is achieved, one can inactivate the AID by any means known in the art.

In other embodiments of the invention, in addition to selecting cells that express AID (either naturally or induced to express AID), the cells may be naturally defective in mismatch repair or be induced to be defective in mismatch repair. The hybridoma cells may be defective in mismatch repair due to the fact that the cells that are capable of producing antibodies are naturally defective in mismatch repair. Alternatively, the immortalized cell may be naturally defective in mismatch repair. Alternatively, both the cells capable of producing antibodies and the immortalized cells may be naturally defective in mismatch repair. In some embodiments, the cells are manipulated to be defective in mismatch repair due to knocking out one or more genes responsible for mismatch repair, introducing a dominant negative allele of a mismatch repair gene as described above, or by chemically inhibiting mismatch repair as described in Nicolaides et al., WO02/054856, "Chemical Inhibitors of Mismatch Repair," the disclosure of which is explicitly incorporated by reference herein in its entirety.

In another embodiment of the invention, the antibody-producing cells may be hybridomas producing antibodies rather than hybridomas made de novo. In other embodiments, the antibody-producing cells may be mammalian expression cells that produce antibodies due to transformation of the cells with polynucleotides encoding immunoglobulin heavy and light chains. The expression cells may be expressing immunoglobulins or derivatives thereof. Such products include, for example, fully human antibodies, human antibody homologs, humanized antibody homologs, chimeric antibody homologs, Fab, Fab', F(ab')$_2$ and F(v) antibody fragments, single chain antibodies, and monomers or dimers of antibody heavy or light chains or mixtures thereof. The known hybridomas and mammalian expression cells (as well as transfectomas) may be further manipulated as described above by inhibiting mismatch repair with simulataneous or separate stimulation of expression of AID (or simple selection of cells naturally expressing AID).

In each case, once a desired phenotype is achieved, genomic stability may be restored as described above such that further mutation does not occur.

The invention also comprises isolated antibody-producing cells produced by any of the foregoing methods.

For further information on the background of the invention the following references may be consulted, each of which is incorporated herein by reference in its entirety:

1. Glaser, V. (1996) Can ReoPro repolish tarnished monoclonal therapeutics? *Nat. Biotechol.* 14:1216-1217.
2. Weiner, L. M. (1999) Monoclonal antibody therapy of cancer. *Semin. Oncol.* 26:43-51.
3. Saez-Llorens, X. E. et al. (1998) Safety and pharmacokinetics of an intramuscular humanized monoclonal antibody to respiratory syncytial virus in premature infants and infants with bronchopulmonary dysplasia. *Pediat. Infect. Dis. J* 17:787-791.
4. Shield, C. F. et al. (1996) A cost-effective analysis of OKT3 induction therapy in cadaveric kidney transplantation. *Am. J. Kidney Dis.* 27:855-864.
5. Khazaeli, M. B. et al. (1994) Human immune response to monoclonal antibodies. *J Immunother.* 15:42-52.
6. Emery, S. C. and W. J. Harris "Strategies for humanizing antibodies" In: ANTIBODY ENGINEERING C. A. K. Borrebaeck (Ed.) Oxford University Press, N.Y. 1995, pp. 159-183.
7. U.S. Pat. No. 5,530,101 to Queen and Selick.
8. Reff, M. E. (1993) High-level production of recombinant immunoglobulins in mammalian cells. *Curr. Opin. Biotechnol.* 4:573-576.
9. Neuberger, M. and M. Gruggermann, (1997) Monoclonal antibodies. Mice perform a human repertoire. *Nature* 386:25-26.
10. Fiedler, U. and U. Conrad (1995) High-level production and long-term storage of engineered antibodies in transgenic tobacco seeds. *Bio/Technology* 13:1090-1093.
11. Baker S. M. et al. (1995) Male defective in the DNA mismatch repair gene PMS2 exhibit abnormal chromosome synapsis in meiosis. *Cell* 82:309-319.
12. Bronner, C. E. et al. (1994) Mutation in the DNA mismatch repair gene homologue hMLH1 is associated with hereditary non-polyposis colon cancer. *Nature* 368:258-261.
13. de Wind N. et al. (1995) Inactivation of the mouse Msh2 gene results in mismatch repair deficiency, methylation tolerance, hyperrecombination, and predisposition to cancer. *Cell* 82:321-300.
14. Drummond, J. T. et al. (1995) Isolation of an hMSH2-p160 heterodimer that restores mismatch repair to tumor cells. *Science* 268:1909-1912.
15. Modrich, P. (1994) Mismatch repair, genetic stability, and cancer. *Science* 266:1959-1960.
16. Nicolaides, N. C. et al. (1998) A Naturally Occurring hPMS2 Mutation Can Confer a Dominant Negative Mutator Phenotype. *Mol. Cell. Biol.* 18:1635-1641.
17. Prolla, T. A. et al. (1994) MLH1, PMS1, and MSH2 Interaction during the initiation of DNA mismatch repair in yeast. *Science* 264:1091-1093.
18. Strand, M. et al. (1993) Destabilization of tracts of simple repetitive DNA in yeast by mutations affecting DNA mismatch repair. *Nature* 365:274-276.
19. Su, S. S., R. S. Lahue, K. G. Au, and P. Modrich (1988) Mispair specificity of methyl directed DNA mismatch corrections in vitro. *J. Biol. Chem.* 263:6829-6835.
20. Parsons, R. et al. (1993) Hypermutability and mismatch repair deficiency in RER+ tumor cells. *Cell* 75:1227-1236.
21. Papadopoulos, N. et al. (1993) Mutation of a mutL homolog is associated with hereditary colon cancer. *Science* 263:1625-1629.
22. Perucho, M. (1996) Cancer of the microsatellite mutator phenotype. *Biol. Chem.* 377:675-684.
23. Nicolaides N. C., K. W. Kinzler, and B. Vogelstein (1995) Analysis of the 5' region of PMS2 reveals heterogenous transcripts and a novel overlapping gene. *Genomics* 29:329-334.
24. Nicolaides, N. C. et al. (1995) Genomic organization of the human PMS2 gene family. *Genomics* 30:195-206.
25. Palombo, F. et al. (1994) Mismatch repair and cancer. *Nature* 36:417.
26. Eshleman J. R. and S. D. Markowitz (1996) Mismatch repair defects in human carcinogenesis. *Hum. Mol. Genet.* 5:1489-494.
27. Liu, T. et al. (2000) Microsatellite instability as a predictor of a mutation in a DNA mismatch repair gene in familial colorectal cancer. *Genes Chromosomes Cancer* 27:17-25.
28. Nicolaides, N. C. et al. (1992) The Jun family members, c-JUN and JUND, transactivate the human c-myb promoter via an Ap1 like element. *J. Biol. Chem.* 267:19665-19672.
29. Shields, R. L. et al. (1995) Anti-IgE monoclonal antibodies that inhibit allergen-specific histamine release. *Int. Arch. Allergy Immunol.* 107:412-413.
30. Frigerio L. et al. (2000) Assembly, secretion, and vacuolar delivery of a hybrid immunoglobulin in plants. *Plant Physiol.* 123:1483-1494.
31. Bignami M, (2000) Unmasking a killer: DNA O(6)-methylguanine and the cytotoxicity of methylating agents. *Mutat. Res.* 462:71-82.
32. Drummond, J. T. et al. (1996) Cisplatin and adriamycin resistance are associated with MutLα and mismatch repair deficiency in an ovarian tumor cell line. *J. Biol. Chem.* 271:9645-19648.
33. Galio, L. et al. (1999) ATP hydrolysis-dependent formation of a dynamic ternary nucleoprotein complex with MutS and MutL. *Nucl. Acids Res.* 27:2325-23231.

The above disclosure generally describes the present invention. A more complete understanding can be obtained by reference to the following specific examples which are provided herein for purposes of illustration only, and are not intended to limit the scope of the invention.

EXAMPLES

Example 1

Stable Expression of Dominant Negative MMR Genes in Hybridoma Cells

It has been previously shown by Nicolaides et al. (Nicolaides et al. (1998) A Naturally Occurring hPMS2 Mutation Can Confer a Dominant Negative Mutator Phenotype *Mol. Cell. Biol.* 18:1635-1641) that the expression of a dominant negative allele in an otherwise MMR-proficient cell could render these host cells MMR deficient. The creation of MMR-deficient cells can lead to the generation of genetic alterations throughout the entire genome of a host organisms offspring, yielding a population of genetically altered offspring or siblings that may produce biochemicals with altered properties. This patent application teaches of the use of dominant negative MMR genes in antibody-producing cells, including but not limited to rodent hybridomas, human hybridomas, chimeric rodent cells producing human immunoglobulin gene products, human cells expressing immunoglobulin genes, mammalian cells producing single chain antibodies, and prokaryotic cells producing mammalian immunoglobulin genes or chimeric immunoglobulin molecules such as those contained within single-chain antibodies. The cell expression systems described above that are used to produce antibodies are well known by those skilled in the art of antibody therapeutics.

To demonstrate the ability to create MMR defective hybridomas using dominant negative alleles of MMR genes, we first transfected a mouse hybridoma cell line that is known to produce and antibody directed against the human IgE protein with an expression vector containing the human PMS2 (cell line referred to as HBPMS2), the previously published dominant negative PMS2 mutant referred herein as PMS134 (cell line referred to as HB134), or with no insert (cell line referred to as HBvec). The results showed that the PMS134 mutant could indeed exert a robust dominant negative effect, resulting in biochemical and genetic manifestations of MMR deficiency. Unexpectedly it was found that the full length PMS2 also resulted in a lower MMR activity while no effect was seen in cells containing the empty vector. A brief description of the methods is provided below.

The MMR-proficient mouse H36 hybridoma cell line was transfected with various hPMS2 expression plasmids plus reporter constructs for assessing MMR activity. The MMR genes were cloned into the pEF expression vector, which contains the elongation factor promoter upstream of the cloning site followed by a mammalian polyadenylation signal. This vector also contains the NEOr gene that allows for selection of cells retaining this plasmid. Briefly, cells were transfected with 1 µg of each vector using polyliposomes following the manufacturer's protocol (Life Technologies). Cells were then selected in 0.5 mg/ml of G418 for 10 days and G418 resistant cells were pooled together to analyze for gene expression. The pEF construct contains an intron that separates the exon 1 of the EF gene from exon 2, which is juxtaposed to the 5' end of the polylinker cloning site. This allows for a rapid reverse transcriptase polymerase chain reaction (RT-PCR) screen for cells expressing the spliced products. At day 17, 100,000 cells were isolated and their RNA extracted using the trizol method as previously described (Nicolaides N. C., Kinzler, K. W., and Vogelstein, B. (1995) Analysis of the 5' region of PMS2 reveals heterogeneous transcripts and a novel overlapping gene. *Genomics* 29:329-334). RNAs were reverse-transcribed using Superscript II (Life Technologies) and PCR-amplified using a sense primer located in exon 1 of the EF gene (5'-ttt cgc aac ggg ttt gcc g-3')(SEQ ID NO:49) and an antisense primer (5'-gtt tca gag tta agc ctt cg-3') (SEQ ID NO:50) centered at nt 283 of the published human PMS2 cDNA, which will detect both the full length as well as the PMS134 gene expression. Reactions were carried out using buffers and conditions as previously described (Nicolaides, N. C., et al. (1995) Genomic organization of the human PMS2 gene family. *Genomics* 30:195-206), using the following amplification parameters: 94° C. for 30 sec, 52° C. for 2 min, 72° C. for 2 min, for 30 cycles. Reactions were analyzed on agarose gels. FIG. 1 shows a representative example of PMS expression in stably transduced H36 cells.

Expression of the protein encoded by these genes were confirmed via western blot using a polyclonal antibody directed to the first 20 amino acids located in the N-terminus of the protein following the procedures previously described (data not shown) (Nicolaides et al. (1998) A Naturally Occurring hPMS2 Mutation Can Confer a Dominant Negative Mutator Phenotype. *Mol. Cell. Biol.* 18:1635-1641).

Example 2 hPMS134 Causes a Defect in MMR Activity and Hypermutability in Hybridoma Cells

A hallmark of MMR deficiency is the generation of unstable microsatellite repeats in the genome of host cells. This phenotype is referred to as microsatellite instability (MI) (Modrich, P. (1994) Mismatch repair, genetic stability, and cancer *Science* 266:1959-1960; Palombo, F., et al. (1994) Mismatch repair and cancer *Nature* 36:417). MI consists of deletions and/or insertions within repetitive mono-, di- and/or tri-nucleotide repetitive sequences throughout the entire genome of a host cell. Extensive genetic analysis eukaryotic cells have found that the only biochemical defect that is capable of producing MI is defective MMR (Strand, M., et al. (1993) Destabilization of tracts of simple repetitive DNA in yeast by mutations affecting DNA mismatch repair *Nature* 365:274-276; Perucho, M. (1996) Cancer of the microsatellite mutator phenotype. *Biol. Chem.* 377:675-684; Eshleman J. R., and Markowitz, S. D. (1996) Mismatch repair defects in human carcinogenesis. *Hum. Mol. Genet.* 5:1489-494). In light of this unique feature that defective MMR has on promoting MI, it is now used as a biochemical marker to survey for lack of MMR activity within host cells (Perucho, M. (1996) Cancer of the microsatellite mutator phenotype. *Biol. Chem.* 377:675-684; Eshleman J. R., and Markowitz, S. D. (1996) Mismatch repair defects in human carcinogenesis. *Hum. Mol. Genet.* 5:1489-494; Liu, T., et al. (2000) Microsatellite instability as a predictor of a mutation in a DNA mismatch repair gene in familial colorectal cancer *Genes Chromosomes Cancer* 27:17-25).

A method used to detect MMR deficiency in eukaryotic cells is to employ a reporter gene that has a polynucleotide repeat inserted within the coding region that disrupts its reading frame due to a frame shift. In the case where MMR is defective, the reporter gene will acquire random mutations (i.e. insertions and/or deletions) within the polynucleotide repeat yielding clones that contain a reporter with an open reading frame. We have employed the use of an MMR-sensitive reporter gene to measure for MMR activity in HBvec, HBPMS2, and HBPMS134 cells. The reporter construct used the pCAR-OF, which contains a hygromycin resistance (HYG) gene plus a β-galactosidase gene containing a 29 bp out-of-frame poly-CA tract at the 5' end of its coding region. The pCAR-OF reporter would not generate β-galactosidase activity unless a frame-restoring mutation (i.e., insertion or deletion) arose following transfection. HBvec, HBPMS2, and HB134 cells were each transfected with pCAR-OF vector in duplicate reactions following the protocol described in Example 1. Cells were selected in 0.5 mg/ml G418 and 0.5 mg/ml HYG to select for cells retaining both the MMR effector and the pCAR-OF reporter plasmids. All cultures transfected with the pCAR vector resulted in a similar number of HYG/G418 resistant cells. Cultures were then expanded and tested for β-galactosidase activity in situ as well as by biochemical analysis of cell extracts. For in situ analysis, 100,000 cells were harvested and fixed in 1% gluteraldehyde, washed in phosphate buffered saline solution and incubated in 1 ml of X-gal substrate solution [0.15 M NaCl, 1 mM MgCl$_2$, 3.3 mM K$_4$Fe(CN)$_6$, 3.3 mM K$_3$Fe(CN)$_6$, 0.2% X-Gal] in 24 well plates for 2 hours at 37° C. Reactions were stopped in 500 mM sodium bicarbonate solution and transferred to microscope slides for analysis. Three fields of 200 cells each were counted for blue (β-galactosidase positive cells) or white (β-galactosidase negative cells) to assess for MMR inactivation. Table 1 shows the results from these studies. While no β-galactosidase positive cells were observed in HBvec cells, 10% of the cells per field were β-galactosidase positive in HB134 cultures and 2% of the cells per field were β-galactosidase positive in HBPMS2 cultures.

Figure 2:
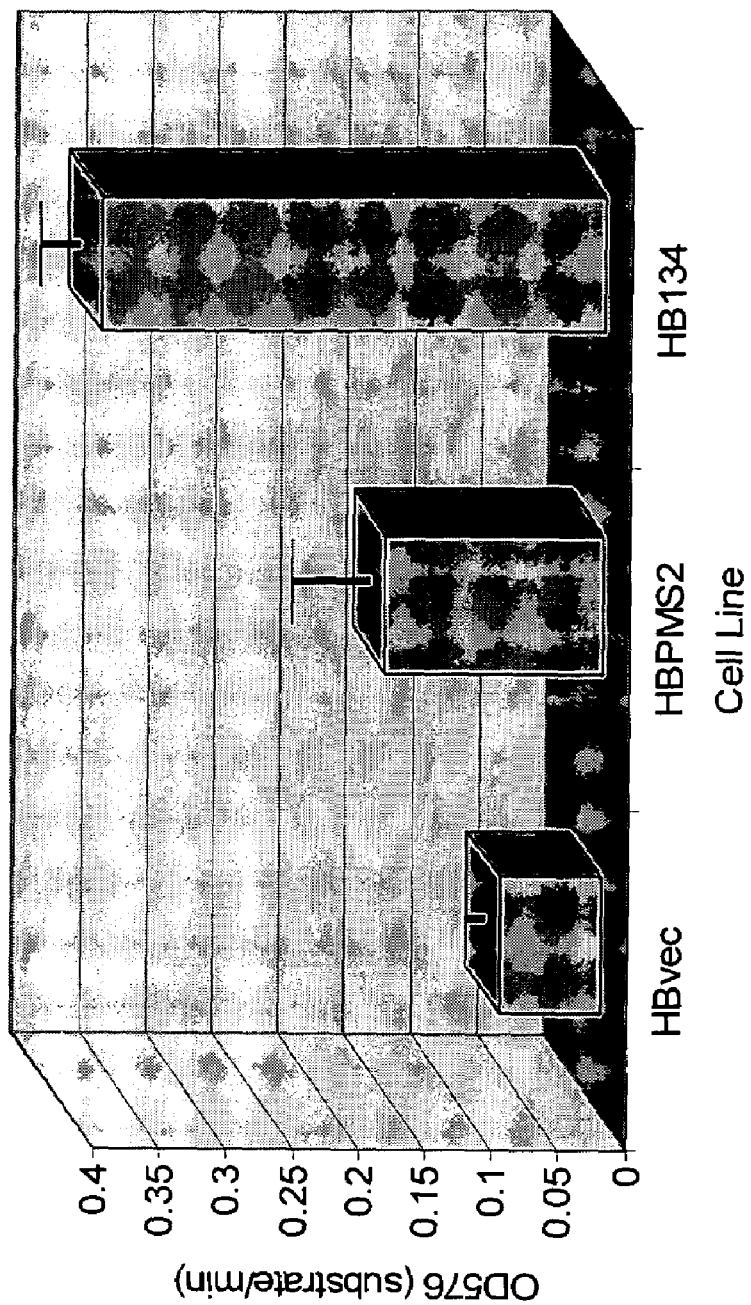
FIG. 2 shows the creation of genetically hypermutable hybridoma cells. Dominant negative MMR gene alleles were expressed in cells expressing a MMR-sensitive reporter gene. Dominant negative alleles such as PMS134 and the expression of MMR genes from other species results in antibody-producer cells with a hypermutable phenotype that can be used to produce genetically altered immunoglobulin genes with enhanced biochemical features as well as lines with increased Ig expression and/or secretion. Values shown represent the amount of converted CPRG substrate which is reflective of the amount of function β-galactosidase contained within the cell from genetic alterations within the pCAR-OF reporter gene. Higher amounts of β-galactosidase activity reflect a higher mutation rate due to defective MMR.

Cell extracts were prepared from the above cultures to measure β-galactosidase using a quantitative biochemical assay as previously described (Nicolaides et al. (1998) A Naturally Occurring hPMS2 Mutation Can Confer a Dominant Negative Mutator Phenotype *Mol. Cell. Biol.* 18:1635-1641; Nicolaides, N. C., et al. (1992) The Jun family members, c-JUN and JUND, transactivate the human c-myb promoter via an Ap1 like element. *J. Biol. Chem.* 267:19665-19672). Briefly, 100,000 cells were collected, centrifuged and resuspended in 200 μls of 0.25M Tris, pH 8.0. Cells were lysed by freeze/thawing three times and supernatants collected after microfugation at 14,000 rpms to remove cell debris. Protein content was determined by spectrophotometric analysis at OD$^{280}$. For biochemical assays, 20 μg of protein was added to buffer containing 45 mM 2-mercaptoethanol, 1 mM MgCl$_2$, 0.1 M NaPO$_4$ and 0.6 mg/ml Chlorophenol red-β-D-galactopyranoside (CPRG, Boehringer Mannheim). Reactions were incubated for 1 hour, terminated by the addition of 0.5 M Na$_2$CO$_3$, and analyzed by spectrophotometry at 576 nm. H36 cell lysates were used to subtract out background. FIG. 2 shows the β-galactosidase activity in extracts from the various cell lines. As shown, the HB134 cells produced the highest amount of β-galactosidase, while no activity was found in the HBvec cells containing the pCAR-OF. These data demonstrate the ability to generate MMR defective hybridoma cells using dominant negative MMR gene alleles.

Table 1. β-galactosidase expression of HBvec, HBPMS2 and HB134 cells transfected with pCAR-OF reporter vectors. Cells were transfected with the pCAR-OF β-galactosidase reporter plasmid. Transfected cells were selected in hygromycin and G418, expanded and stained with X-gal solution to measure for β-galactosidase activity (blue colored cells). 3 fields of 200 cells each were analyzed by microscopy. The results below represent the mean +/− standard deviation of these experiments.

TABLE 1

| CELL LINE | # BLUE CELLS |
|---|---|
| HBvec | 0 +/− 0 |
| HBPMS2 | 4 +/− 1 |
| HB134 | 20 +/− 3 |

Example 3

Figure 3:
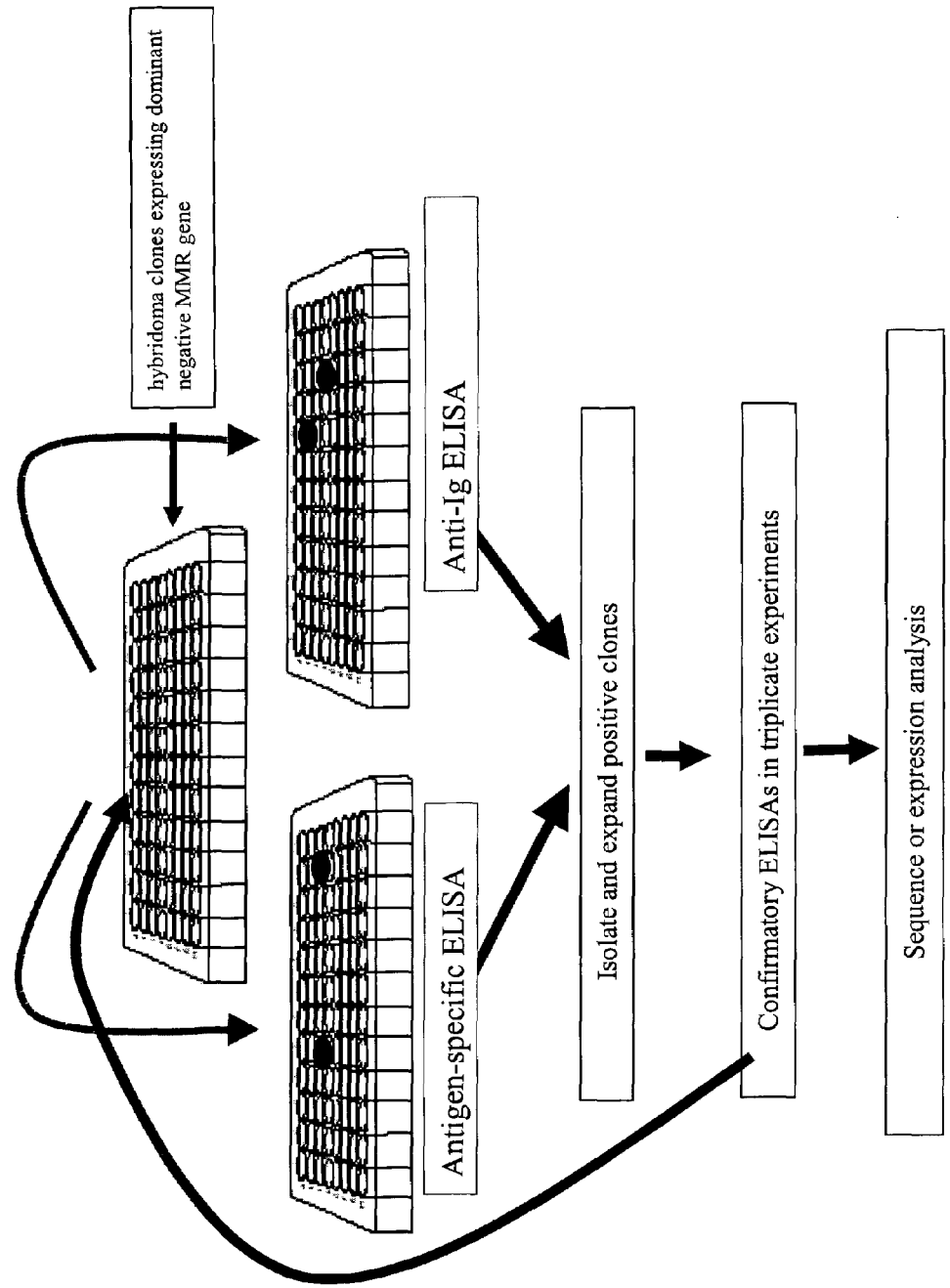
FIG. 3 illustrates a screening method for identifying antibody-producing cells containing antibodies with increased binding activity and/or increased expression/secretion
Figure 4:
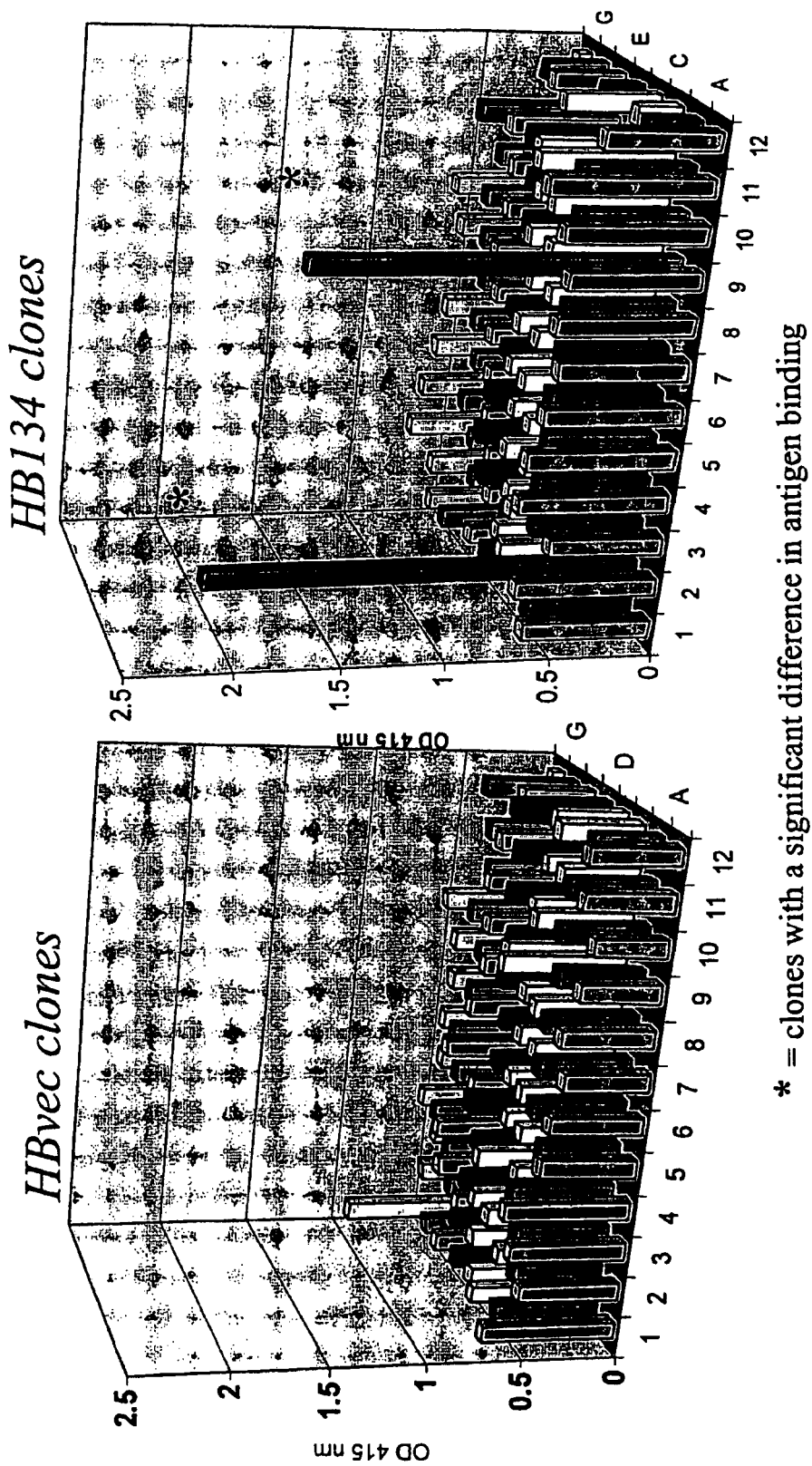
FIG. 4 illustrates the generation of a genetically altered antibody with an increased binding activity. Shown are ELISA values from 96-well plates screened for antibodies specific to hIgE. Two clones with a high binding value were found in HB134 cultures.

Screening Strategy to Identify Hybridoma Clones Producing Antibodies with Higher Binding Affinities and/or Increased Immunoglobulin Production An application of the methods presented within this document is the use of MMR deficient hybridomas or other immunoglobulin producing cells to create genetic alterations within an immunoglobulin gene that will yield antibodies with altered biochemical properties. An illustration of this application is demonstrated within this example whereby the HB134 hybridoma (see Example 1), which is a MMR-defective cell line that produces an anti-human immunoglobulin type E (hIgE) MAb, is grown for 20 generations and clones are isolated in 96-well plates and screened for hIgE binding. FIG. 3 outlines the screening procedure to identify clones that produce high affinity MAbs, which is presumed to be due to an alteration within the light or heavy chain variable region of the protein. The assay employs the use of a plate Enzyme Linked Immunosorbant Assay (ELISA) to screen for clones that produce high-affinity MAbs. 96-well plates containing single cells from HBvec or HB134 pools are grown for 9 days in growth medium (RPMI 1640 plus 10% fetal bovine serum) plus 0.5 mg/ml G418 to ensure clones retain the expression vector. After 9 days, plates are screened using an hIgE plate ELISA, whereby a 96 well plate is coated with 50 μls of a 1 μg/ml hIgE solution for 4 hours at 4° C. Plates are washed 3 times in calcium and magnesium free phosphate buffered saline solution (PBS$^{-/-}$) and blocked in 100 μls of PBS$^{-/-}$ with 5% dry milk for 1 hour at room temperature. Wells are rinsed and incubated with 100 μls of a PBS solution containing a 1:5 dilution of conditioned medium from each cell clone for 2 hours. Plates are then washed 3 times with PBS$^{-/-}$ and incubated for 1 hour at room temperature with 50 μls of a PBS$^{-/-}$ solution containing 1:3000 dilution of a sheep anti-mouse horse radish peroxidase (HRP) conjugated secondary antibody. Plates are then washed 3 times with PBS$^{-/-}$ and incubated with 50 μls of TMB-HRP substrate (BioRad) for 15 minutes at room temperature to detect amount of antibody produced by each clone. Reactions are stopped by adding 50 μls of 500 mM sodium bicarbonate and analyzed by OD at 415 nm using a BioRad plate reader. Clones exhibiting an enhanced signal over background cells (H36 control cells) are then isolated and expanded into 10 ml cultures for additional characterization and confirmation of ELISA data in triplicate experiments. ELISAs are also performed on conditioned (CM) from the same clones to measure total Ig production within the conditioned medium of each well. Clones that produce an increased ELISA signal and have increased antibody levels are then further analyzed for variants that overexpress and/or over-secrete antibodies as described in Example 4. Analysis of five 96-well plates each from HBvec or HB134 cells have found that a significant number of clones with a higher Optical Density (OD) value is observed in the MMR-defective HB134 cells as compared to the HBvec controls. FIG. 4 shows a representative example of HB134 clones producing antibodies that bind to specific antigen (in this case IgE) with a higher affinity. FIG. 4 provides raw data from the analysis of 96 wells of HBvec (left graph) or HB134 (right graph) which shows 2 clones from the HB134 plate to have a higher OD reading due to 1) genetic alteration of the antibody variable domain that leads to an increased binding to IgE antigen, or 2) genetic alteration of a cell host that leads to over-production/secretion of the antibody molecule. Anti-Ig ELISA found that the two clones shown in FIG. 4 have Ig levels within their CM similar to the surrounding wells exhibiting ower OD values. These data suggest that a genetic alteration occurred within the antigen binding domain of the antibody which in turn allows for higher binding to antigen.

Clones that produced higher OD values as determined by ELISA were further analyzed at the genetic level to confirm that mutations within the light or heavy chain variable region have occurred that lead to a higher binding affinity hence yielding to a stronger ELISA signal. Briefly, 100,000 cells are harvested and extracted for RNA using the Triazol method as described above. RNAs are reverse transcribed using Superscript II as suggested by the manufacturer (Life Technology) and PCR-amplified for the antigen binding sites contained within the variable light and heavy chains. Because of the heterogeneous nature of these genes, the following degenerate primers are used to amplify light and heavy chain alleles from the parent H36 strain.

```
Light chain sense:      5'-GGA TTT TCA GGT GCA GAT TTT CAG-3'       (SEQ ID NO: 45)

Light chain antisense:  5'-ACT GGA TGG TGG GAA GAT GGA-3'           (SEQ ID NO: 46)

Heavy chain sense:      5'-A(G/T) GTN (A/C)AG CTN CAG (C/G)AG TC-3' (SEQ ID NO: 47)

Heavy chain antisense:  5'-TNC CTT G(A/G)C CCC AGT A(G/A)(A/T)C-3'  (SEQ ID NO: 48)
```

PCR reactions using degenerate oligonucleotides are carried out at 94° C. for 30 sec, 52° C. for 1 min, and 72° C. for 1 min for 35 cycles. Products are analyzed on agarose gels. Products of the expected molecular weights are purified from the gels by Gene Clean (Bio 101), cloned into T-tailed vectors, and sequenced to identify the wild type sequence of the variable light and heavy chains. Once the wild type sequence has been determined, non-degenerate primers were made for RT-PCR amplification of positive HB134 clones. Both the light and heavy chains were amplified, gel purified and sequenced using the corresponding sense and antisense primers. The sequencing of RT-PCR products gives representative sequence data of the endogenous immunoglobulin gene and not due to PCR-induced mutations. Sequences from clones were then compared to the wild type sequence for sequence comparison. An example of the ability to create in vivo mutations within an immunoglobulin light or heavy chain is shown in FIG. 5, where HB134 clone92 was identified by ELISA to have an increased signal for hIgE. The light chain was amplified using specific sense and antisense primers. The light chain was RT-PCR amplified and the resulting product was purified and analyzed on an automated ABI377 sequencer. As shown in clone A, a residue –4 upstream of the CDR region 3 had a genetic change from ACT to TCT, which results in a Thr to Ser change within the framework region just preceding the CDR#3. In clone B, a residue –6 upstream of the CDR region had a genetic change from CCC to CTC, which reslts in a Pro to Leu change within framework region preceeding CDR#2.

The ability to generate random mutations in immunoglobulin genes or chimeric immunoglobulin genes is not limited to hybridomas. Nicolaides et al. ((1998) A Naturally Occurring hPMS2 Mutation Can Confer a Dominant Negative Mutator Phenotype *Mol. Cell. Biol.* 18:1635-1641) has previously shown the ability to generate hypermutable hamster cells and produce mutations within an endogenous gene. A common method for producing humanized antibodies is to graft CDR sequences from a MAb (produced by immunizing a rodent host) onto a human Ig backbone and transfect the chimeric genes into Chinese Hamster Ovary (CHO) cells which in turn produce a functional Ab that is secreted by the CHO cells (Shields, R. L., et al. (1995) Anti-IgE monoclonal antibodies that inhibit allergen-specific histamine release. *Int. Arch. Allergy Immunol.* 107:412-413). The methods described within this application are also useful for generating genetic alterations within Ig genes or chimeric Igs transfected within host cells such as rodent cell lines, plants, yeast and prokaryotes (Frigerio L, et al. (2000) Assembly, secretion, and vacuolar delivery of a hybrid immunoglobulin in plants. *Plant Physiol.* 123:1483-1494).

These data demonstrate the ability to generate hypermutable hybridomas, or other Ig producing host cells that can be grown and selected, to identify structurally altered immunoglobulins yielding antibodies with enhanced biochemical properties, including but not limited to increased antigen binding affinity. Moreover, hypermutable clones that contain missense mutations within the immunoglobulin gene that result in an amino acid change or changes can be then further characterized for in vivo stability, antigen clearance, on-off binding to antigens, etc. Clones can also be further expanded for subsequent rounds of in vivo mutations and can be screened using the strategy listed above.

The use of chemical mutagens to produce genetic mutations in cells or whole organisms are limited due to the toxic effects that these agents have on "normal" cells. The use of chemical mutagens such as MNU in MMR defective organisms is much more tolerable yielding to a 10 to 100 fold increase in genetic mutation over MMR deficiency alone (Bignami M, (2000) Unmasking a killer: DNA O(6)-methylguanine and the cytotoxicity of methylating agents. *Mutat. Res.* 462:71-82). This strategy allows for the use of chemical mutagens to be used in MMR-defective Ab producing cells as a method for increasing additional mutations within immunoglobulin genes or chimeras that may yield functional Abs with altered biochemical properties such as enhanced binding affinity to antigen, etc.

Example 4

Generation of Antibody Producing Cells with Enhanced Antibody Production

Analysis of clones from H36 and HB134 following the screening strategy listed above has identified a significant number of clones that produce enhanced amounts of antibody into the medium. While a subset of these clones gave higher Ig binding data as determined by ELISA as a consequence of mutations within the antigen binding domains contained in the variable regions, others were found to contain "enhanced" antibody production. A summary of the clones producing enhanced amounts of secreted MAb is shown in TABLE 2, where a significant number of clones from HB134 cells were found to produce enhanced Ab production within the conditioned medium as compared to H36 control cells.

TABLE 2. Generation of hybridoma cells producing high levels of antibody. HB134 clones were assayed by ELISA for elevated Ig levels. Analysis of 480 clones showed that a significant number of clones had elevated MAb product levels in their CM. Quantification showed that several of these clones produced greater than 500 ngs/ml of MAb due to either enhanced expression and/or secretion as compared to clones from the H36 cell line.

TABLE 2

Production of MAb in CM from H36 and HB134 clones.

| Cell Line | % clones > 400 ng/ml | % clones > 500 ng/ml |
|---|---|---|
| H36 | 1/480 = 0.2% | 0/480 = 0% |
| HB134 | 50/480 = 10% | 8/480 = 1.7% |

Figure 6:
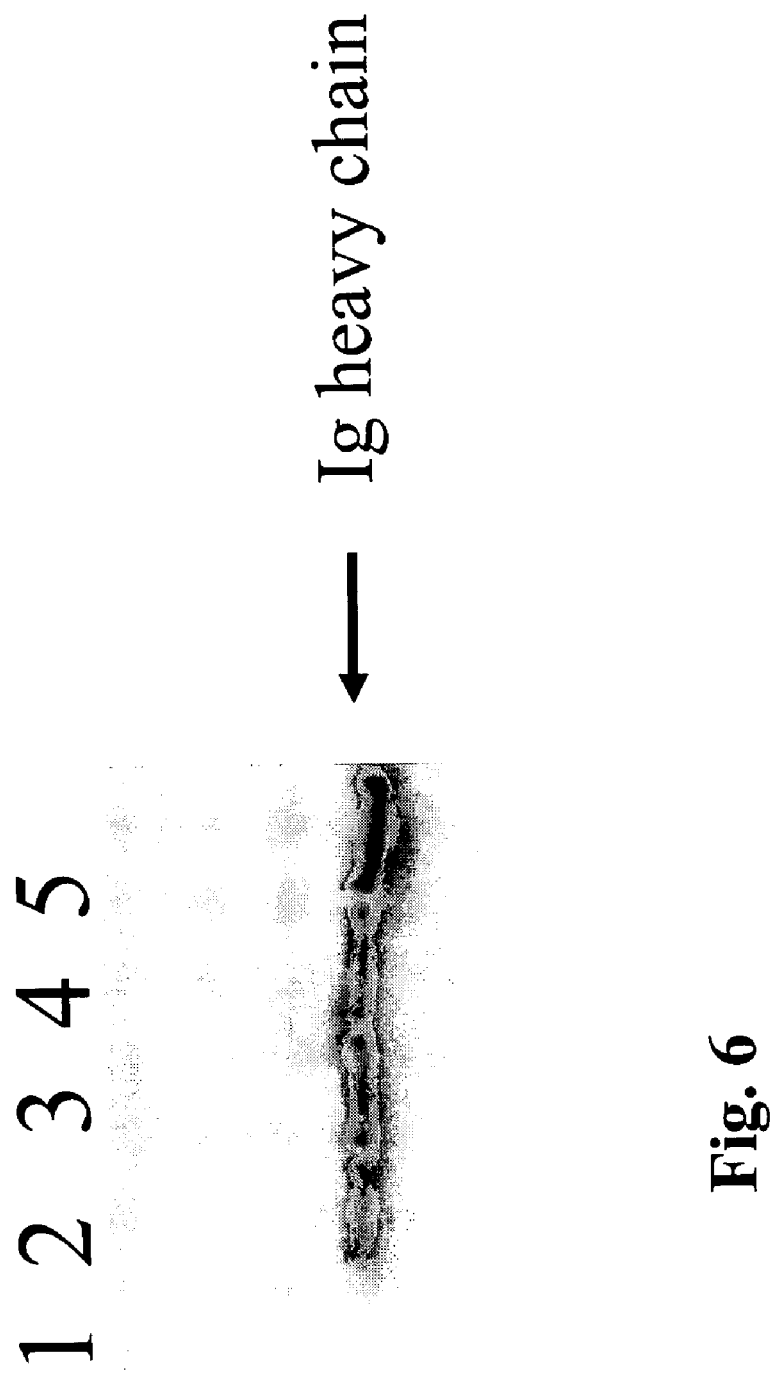
FIG. 6 illustrates the generation of MMR-defective clones with enhanced steady state Ig protein levels. A Western blot of heavy chain immunglobulins from HB134 clones with high levels of MAb (>500 ngs/ml) within the conditioned medium shows that a subset of clones express higher steady state levels of immunoglobulins (Ig). The H36 cell line was used as a control to measure steady state levels in the parental strain. Lane 1: fibroblast cells (negative control); Lane 2: H36 cell; Lane 3: HB134 clone with elevated MAb levels; Lane 4: HB134 clone with elevated MAb levels; Lane 5: HB134 clone with elevated MAb levels.

Cellular analysis of HB134 clones with higher MAb levels within the conditioned medium (CM) were analyzed to determine if the increased production was simply due to genetic alterations at the Ig locus that may lead to over-expression of the polypeptides forming the antibody, or due to enhanced secretion due to a genetic alteration affecting secretory pathway mechanisms. To address this issue, we expanded three HB134 clones that had increased levels of antibody within their CM. 10,000 cells were prepared for western blot analysis to assay for intracellular steady state Ig protein levels (FIG. 6). In addition, H36 cells were used as a standard reference (Lane 2) and a rodent fibroblast (Lane 1) was used as an Ig negative control. Briefly, cells were pelleted by centrifugation and lysed directly in 300 μl of SDS lysis buffer (60 mM Tris, pH 6.8, 2% SDS, 10% glycerol, 0.1 M 2-mercaptoethanol, 0.001% bromophenol blue) and boiled for 5 minutes. Lysate proteins were separated by electrophoresis on 4-12% NuPAGE gels for analysis of Ig heavy chain. Gels were electroblotted onto Immobilon-P (Millipore) in 48 mM Tris base, 40 mM glycine, 0.0375% SDS, 20% methanol and blocked at room temperature for 1 hour in Tris-buffered saline (TBS) plus 0.05% Tween-20 and 5% condensed milk. Filters were probed with a 1:10,000 dilution of sheep anti-mouse horseradish peroxidase conjugated monoclonal antibody in TBS buffer and detected by chemiluminescence using Supersignal substrate (Pierce). Experiments were repeated in duplicates to ensure reproducibility. FIG. 6 shows a representative analysis where a subset of clones had enhanced Ig production which accounted for increased Ab production (Lane 5) while others had a similar steady state level as the control sample, yet had higher levels of Ab within the CM. These data suggest a mechanism whereby a subset of HB134 clones contained a genetic alteration that in turn produces elevated secretion of antibody.

The use of chemical mutagens to produce genetic mutations in cells or whole organisms are limited due to the toxic effects that these agents have on "normal" cells. The use of chemical mutagens such as MNU in MMR defective organisms is much more tolerable yielding to a 10 to 100 fold increase in genetic mutation over MMR deficiency alone (Bignami M, (2000) Unmasking a killer: DNA O(6)-methylguanine and the cytotoxicity of methylating agents. *Mutat. Res.* 462:71-82). This strategy allows for the use of chemical mutagens to be used in MMR-defective Ab-producing cells as a method for increasing additional mutations within immunoglobulin genes or chimeras that may yield functional Abs with altered biochemical properties such as enhanced binding affinity to antigen, etc.

Example 5

Establishment of Genetic Stability in Hybridoma Cells with New Output Trait

The initial steps of MMR are dependent on two protein complexes, called MutSα and MutLα (Nicolaides et al. (1998) A Naturally Occurring hPMS2 Mutation Can Confer a Dominant Negative Mutator Phenotype. *Mol. Cell. Biol.* 18:1635-1641). Dominant negative MMR alleles are able to perturb the formation of these complexes with downstream biochemicals involved in the excision and polymerization of nucleotides comprising the "corrected" nucleotides. Examples from this application show the ability of a truncated MMR allele (PMS134) as well as a full length human PMS2 when expressed in a hybridoma cell line is capable of blocking MMR resulting in a hypermutable cell line that gains genetic alterations throughout its entire genome per cell division. Once a cell line is produced that contains genetic alterations within genes encoding for an antibody, a single chain antibody, over-expression of immunoglobulin genes and/or enhanced secretion of antibody, it is desirable to restore the genomic integrity of the cell host. This can be achieved by the use of inducible vectors whereby dominant negative MMR genes are cloned into such vectors, introduced into Ab-producing cells and the cells are cultured in the presence of inducer molecules and/or conditions. Inducible vectors include but are not limited to chemical regulated promoters such as the steroid inducible MMTV, tetracycline regulated promoters, temperature sensitive MMR gene alleles, and temperature sensitive promoters.

The results described above lead to several conclusions. First, expression of hPMS2 and PMS2-134 results in an increase in microsatellite instability in hybridoma cells. That this elevated microsatellite instability is due to MMR deficiency was proven by evaluation of extracts from stably transduced cells. The expression of PMS2-134 results in a polar defect in MMR, which was only observed using heteroduplexes designed to test repair from the 5' direction (no significant defect in repair from the 3' direction was observed in the same extracts) (Nicolaides et al. (1998) A Naturally Occurring hPMS2 Mutation Can Confer a Dominant Negative Mutator Phenotype. *Mol. Cell. Biol.* 18:1635-1641). Interestingly, cells deficient in hMLH1 also have a polar defect in MMR, but in this case preferentially affecting repair from the 3' direction (Drummond, J. T, et al. (1996) Cisplatin and adriamycin resistance are associated with MutLα and mismatch repair deficiency in an ovarian tumor cell line. *J. Biol. Chem.* 271:9645-19648). It is known from previous studies in both prokaryotes and eukaryotes that the separate enzymatic components mediate repair from the two different directions. Our results, in combination with those of Drummond et al. (Shields, R. L., et al. (1995) Anti-IgE monoclonal antibodies that inhibit allergen-specific histamine release. *Int. Arch Allergy Immunol.* 107:412-413), strongly suggest a model in which 5' repair is primarily dependent on hPMS2 while 3' repair is primarily dependent on hMLH1. It is easy to envision how the dimeric complex between PMS2 and MLH1 might set up this directionality. The combined results also demonstrate that a defect in directional MMR is sufficient to produce a MMR-defective phenotype and suggests that any MMR gene allele is useful to produce genetically altered hybridoma cells, or a cell line that is producing Ig gene products. Moreover, the use of such MMR alleles will be useful for generating genetically altered Ig polypeptides with altered biochemical properties as well as cell hosts that produce enhanced amounts of antibody molecules.

Another method that is taught in this application is that any method used to block MMR can be performed to generate hypermutablility in an antibody-producing cell that can lead to genetically altered antibodies with enhanced biochemical features such as but not limited to increased antigen binding, enhanced pharmacokinetic profiles, etc. These processes can also to be used to generate antibody producer cells that have increased Ig expression as shown in Example 4, FIG. 6 and/or increased antibody secretion as shown in Table 2.

Figure 5A:
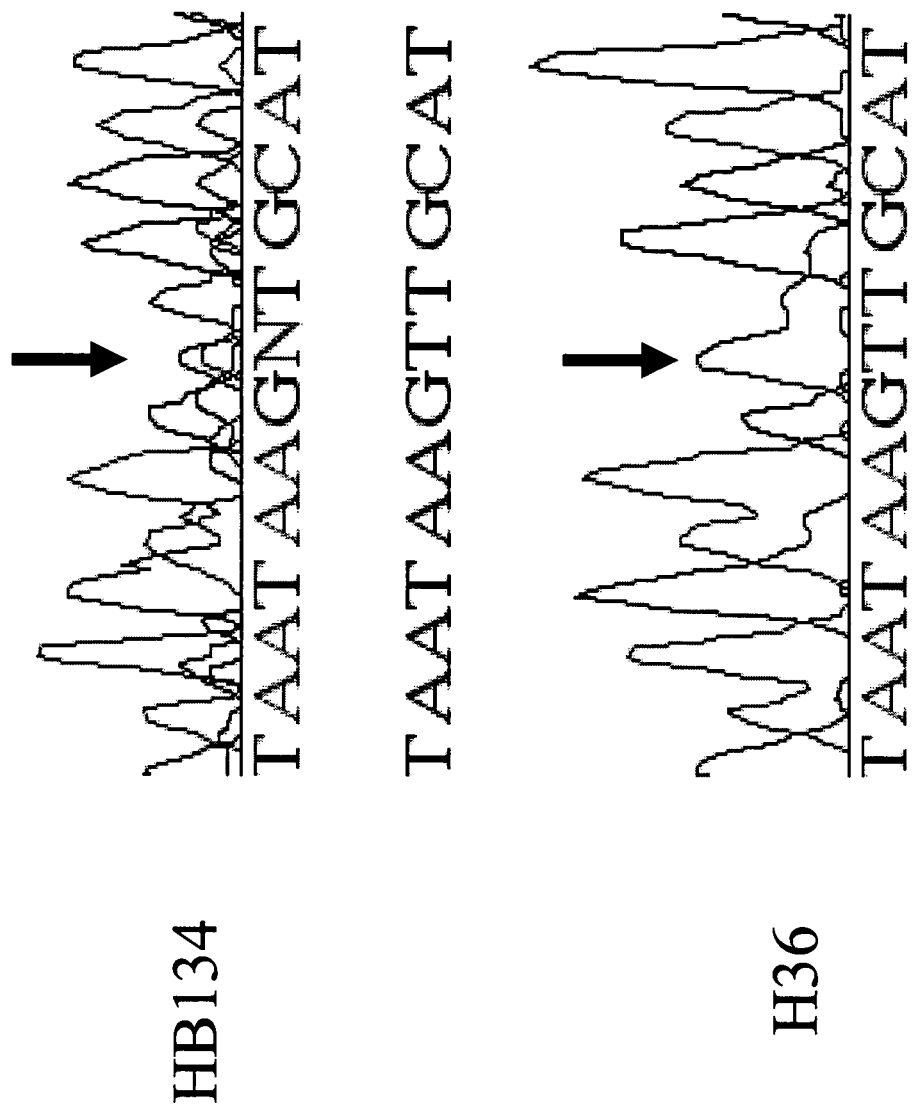
FIG. 5A illustrates sequence alteration within variable chain of an antibody (a mutation within the light chain variable region in MMR-defective HB134 antibody-producer cells). Arrows indicate the nucleotide at which a mutation occurred in a subset of cells from a clone derived from HB134 cells. The HB134 sequence (SEQ ID NO:51) is shown as the top line and the parental H36 sequence (SEQ ID NO:52) is shown above and below the sequence tracing. The change results in a Thr to Ser change within the light chain variable region. The coding sequence is in the antisense direction.
Figure 5B:
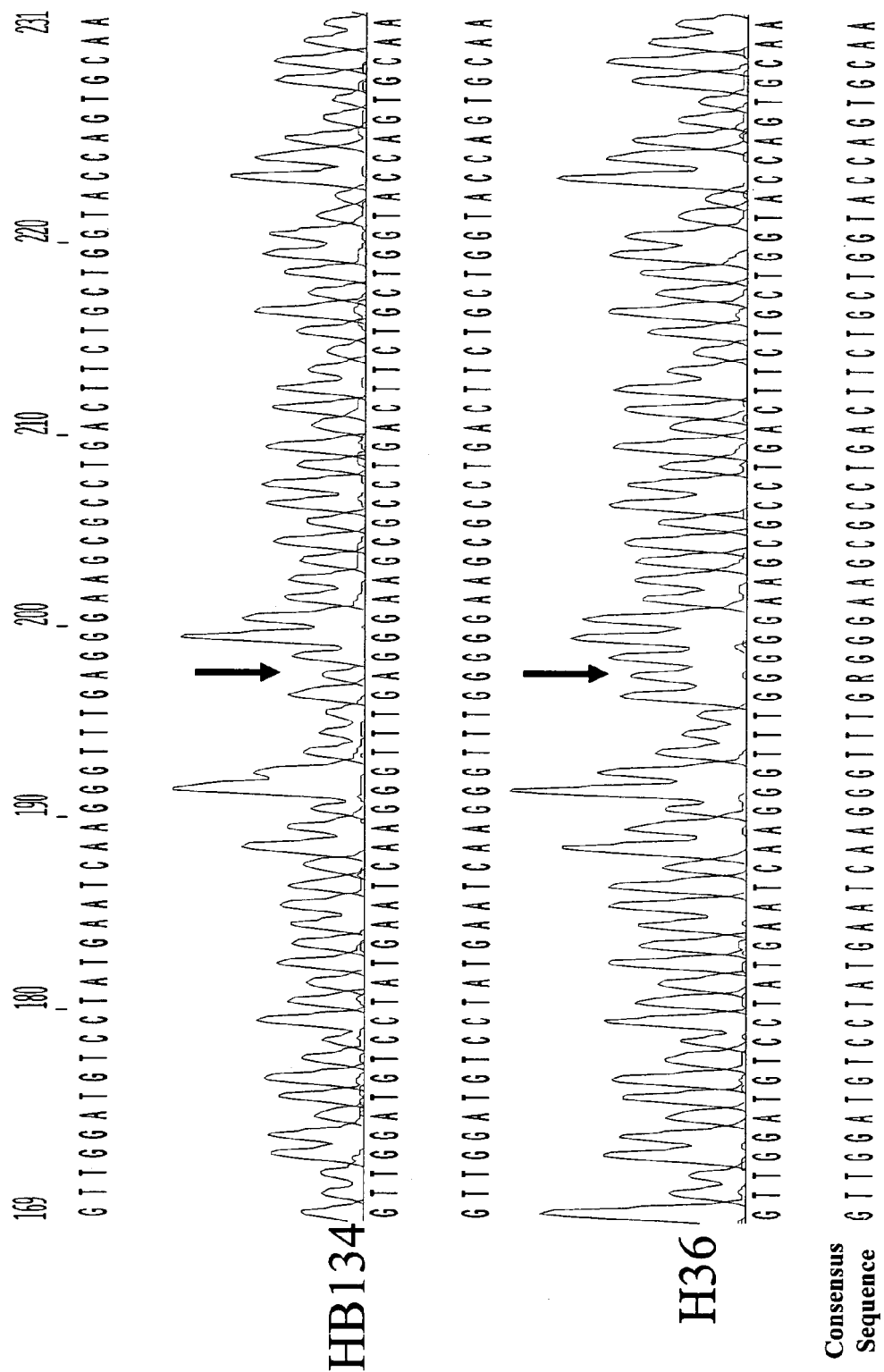
FIG. 5B illustrates sequence alteration within variable chain of an antibody (a mutation within the light chain variable region in MMR-defective HB134 antibody-producer cells). The HB134 sequence (SEQ ID NO:53) is shown above and below the tracing for the HB134 sequence, and the parental H36 sequence (SEQ ID NO:54) is shown above and below the H36 sequence tracing. A consensus sequence (SEQ ID NO:55) is shown at the bottom of the figure. Arrows indicate the nucleotide at which a mutation occurred in a subset of cells from a clone derived from HB134 cells. The change results in a Pro to Leu change within the light chain variable region.

In addition, we demonstrate the utility of blocking MMR in antibody-producing cells to increase genetic alterations within Ig genes that may lead to altered biochemical features such as, but not limited to, increased antigen-binding affinities (FIGS. 5A and 5B). The blockade of MMR in such cells can be through the use of dominant negative MMR gene alleles from any species including bacteria, yeast, protozoa, insects, rodents, primates, mammalian cells, and man. Blockade of MMR can also be generated through the use of antisense RNA or deoxynucleotides directed to any of the genes involved in the MMR biochemical pathway. Blockade of MMR can be through the use of polypeptides that interfere with subunits of the MMR complex including but not limited to antibodies. Finally, the blockade of MMR may be through the use chemicals such as but not limited to nonhydrolyzable ATP analogs, which have been shown to block MMR (Galio, L, et al. (1999) ATP hydrolysis-dependent formation of a dynamic ternary nucleoprotein complex with MutS and MutL. *Nucl. Acids Res.* 27:2325-23231).

Example 6

Figure 7:
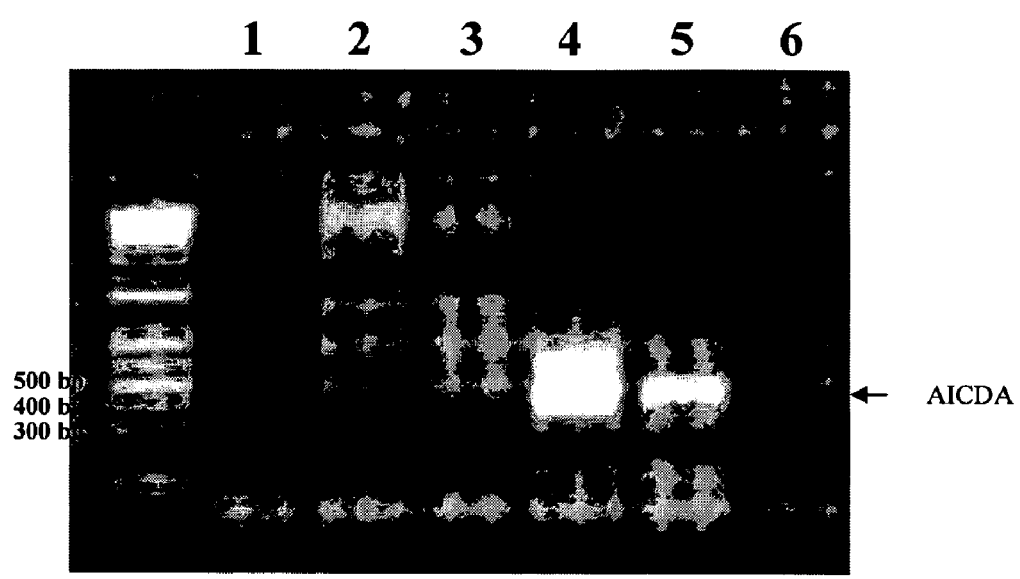
FIG. 7 demonstrates the expression by selected clones of activation-induced cytidine deaminase. Lane 1, water control; Lane 2, 5-8 RT+(SUPERSCRIPT); Lane 3, 5-8 RT−(SUPERSCRIPT); Lane 4, 7-6 (EXPRESSDIRECT); Lane 5, 8-2 (EXPRESSDIRECT); Lane 6,3-32 (EXPRESSDIRECT).

To demonstrate that cells may be selected that express AID, cDNA from hybridoma cells generated by in vitro immunization was generated using either SuperScript II (for clones 5-8) or ExpressDirect (for clones 7-6,8-2 and 3-32). AID (Genbank Accession No.: NM_020661 (SEQ ID NO:39) which encodes the AID protein (SEQ ID NO:40)) was amplified using primers AID-77-F (ATGGACAGCCTCTTGATGAA) (SEQ ID NO:41) and AID-561-R (CAGGCTTTGAAAGTTCTTTC) (SEQ ID NO:42) to generate an amplicon of 484 bp. PCR conditions: 95° C., 5 min. 1x; 94° C., 30 sec; 55° C., 30 sec; 72° C., 30 sec 35x; 72° C., 7 min. 1 x. 10% of reaction mixture was analysed on a 1% agarose gel. The results are shown in FIG. 7.

What is claimed is:

1. A method for generating a hypermutable antibody-producing cell in vitro comprising introducing into an antibody-producing cell a polynucleotide comprising a nucleic acid sequence encoding a PMS2 having an ATPase domain, wherein expression of said polynucleotide inhibits mismatch repair, wherein inhibition of mismatch repair stimulates expression of activation-induced cytidine deaminase, thereby generating a hypermutable antibody-producing cell.

2. The method of claim 1 wherein said PMS2 is a mammalian PMS2.

3. The method of claim 1 wherein said PMS2 is a rodent PMS2.

4. The method of claim 1 wherein said PMS2 is a human PMS2.

5. The method of claim 1 wherein said PMS2 is a plant PMS2.

6. The method of claim 1 further comprising the step of inactivating the polynucleotide, thereby producing a genetically stable antibody-producing cell.

7. A method for producing hybridoma cells producing antibodies from in vitro immunized immunoglobulin-producing cells comprising:
(a) combining cells capable of producing immunoglobulins with an immunogenic antigen in vitro;
(b) fusing said cells with myeloma cells to form parental hybridoma cells, wherein a polynucleotide comprising a nucleic acid sequence encoding a PMS2 having an ATPase domain is transfected into said hybridoma cells, wherein expression of said polynucleotide inhibits mismatch repair;
(c) selecting for mismatch repair-inhibited hybridoma cells exhibiting increased expression of activation-induced cytidine deaminase relative to mismatch repair-proficient parental hybridoma cells, wherein expression of activation-induced cytidine deaminase is stimulated by said inhibition of mismatch repair;
(d) incubating the selected mismatch repair-inhibited hybridoma cells to allow for mutagenesis, thereby forming hypermutated hybridoma cells; and
(e) selecting hypermutated hybridoma cells that produce antibodies that specifically bind antigen, thereby producing hybridoma cells producing antibodies from in vitro immunized immunoglobulin-producing cells.

8. The method of claim 7 wherein said activation-induced cytidine deaminase is a mammalian activation-induced cytidine deaminase.

9. The method of claim 8 wherein said activation-induced cytidine deaminase is a human activation-induced cytidine deaminase.

10. The method of claim 7 wherein said activation-induced cytidine deaminase is a mouse activation-induced cytidine deaminase.

11. The method of claim 7 wherein said polynucleotide encodes a truncated form of a PMS2 protein.

12. The method of claim 11 wherein said PMS2 is a plant PMS2.

13. The method of claim 11 wherein said PMS2 is a mammalian PMS2.

14. The method of claim 13 wherein said PMS2 is a human PMS2.

15. A method for producing hybridoma cells producing antibodies from in vitro immunized immunoglobulin-producing cells comprising:
(a) combining cells capable of producing immunoglobulins with an immunogenic antigen in vitro;
(b) fusing said cells with myeloma cells to form parental hybridoma cells, wherein a polynucleotide comprising a nucleic acid sequence encoding a PMS2 having an ATPase domain is transfected into said myeloma cells, wherein expression of said polynucleotide inhibits mismatch repair;
(c) selecting for mismatch repair-inhibited hybridoma cells exhibiting increased expression of activation-induced cytidine deaminase relative to mismatch repair-proficient cells, wherein expression of activation-induced cytidine deaminase is stimulated by said inhibition of mismatch repair;
(d) incubating the selected mismatch repair-inhibited hybridoma cells to allow for mutagenesis, thereby forming hypermutated hybridoma cells; and
(e) selecting hypermutated hybridoma cells that produce antibodies that specifically bind antigen, thereby producing hybridoma cells producing antibodies from in vitro immunized immunoglobulin-producing cells.

16. A method for producing hybridoma cells producing antibodies from in vitro immunized immunoglobulin-producing cells comprising:
(a) combining cells capable of producing immunoglobulins with an immunogenic antigen in vitro, wherein a polynucleotide comprising a nucleic acid sequence encoding a PMS2 having an ATPase domain is transfected into said cells capable of producing immunoglobulins, wherein expression of said polynucleotide inhibits mismatch repair;
(b) fusing said cells with myeloma cells to form parental hybridoma cells;
(c) selecting for mismatch repair-inhibited hybridoma cells exhibiting increased expression of activation-induced cytidine deaminase relative to mismatch repair-proficient cells, wherein expression of activation-induced cytidine deaminase is stimulated by said inhibition of mismatch repair;
(d) incubating the selected mismatch repair-inhibited hybridoma cells to allow for mutagenesis, thereby forming hypermutated hybridoma cells; and
(e) selecting hypermutated hybridoma cells that produce antibodies that specifically bind antigen, thereby producing hybridoma cells producing antibodies from in vitro immunized immunoglobulin-producing cells.

17. A method for generating a hypermutable antibody-producing cell in vitro comprising: introducing into an antibody-producing cell a polynucleotide comprising a nucleic acid sequence encoding a PMS2 having an ATPase domain, wherein expression of said polynucleotide inhibits mismatch repair, thereby generating a mismatch repair-inhibited antibody-producing cell; culturing said mismatch repair-inhibited antibody-producing cell to yield a population of mismatch repair-inhibited antibody-producing cells; and selecting a mismatch repair-inhibited antibody-producing cell from said population that exhibits increased expression of activation-induced cytidine deaminase relative to mismatch repair-proficient antibody-producing cells, wherein inhibition of mismatch repair in said mismatch repair-inhibited antibody-producing cell by said expression of said polynucleotide increases expression of activation-induced cytidine deaminase relative to mismatch repair-proficient antibody-producing cells; thereby generating a hypermutable antibody-producing cell.

18. The method of claim 17 wherein said antibody-producing cell is a hybridoma cell.

19. The method of claim 17 wherein said antibody-producing cell is a mammalian expression cell transfected with polynucleotides encoding immunoglobulin heavy and light chains.

20. The method of claim 1 wherein said PMS2 is PMS2-134.

21. The method of claim 20 wherein said PMS2-134 is encoded by the nucleic acid sequence SEQ ID NO:5, SEQ ID NO:33, or SEQ ID NO:37.

22. The method of claim 7 wherein said PMS2 is PMS2-134.

23. The method of claim 22 wherein said PMS2-134 is encoded by the nucleic acid sequence SEQ ID NO:5, SEQ ID NO:33, or SEQ ID NO:37.

24. The method of claim 15 wherein said PMS2 is PMS2-134.

25. The method of claim 24 wherein said PMS2-134 is encoded by the nucleic acid sequence SEQ ID NO:5, SEQ ID NO:33, or SEQ ID NO:37.

26. The method of claim 16 wherein said PMS2 is PMS2-134.

27. The method of claim 26 wherein said PMS2-134 is encoded by the nucleic acid sequence SEQ ID NO:5, SEQ ID NO:33, or SEQ ID NO:37.

28. The method of claim 17 wherein said PMS2 is PMS2-134.

29. The method of claim 28 wherein said PMS2-134 is encoded by the nucleic acid sequence SEQ ID NO:5, SEQ ID NO:33, or SEQ ID NO:37.

* * * * *